US 8,442,688 B2

(12) United States Patent
Loutfi

(10) Patent No.: US 8,442,688 B2
(45) Date of Patent: May 14, 2013

(54) SYSTEM FOR MONITORING PLANT EQUIPMENT

(75) Inventor: Moheb Y. Loutfi, Bloomsdale, MO (US)

(73) Assignee: Holcim (US), Inc., Dundee, MI (US)

( * ) Notice: Subject to any disclaimer, the term of this patent is extended or adjusted under 35 U.S.C. 154(b) by 419 days.

(21) Appl. No.: 12/695,667

(22) Filed: Jan. 28, 2010

(65) Prior Publication Data
US 2011/0184547 A1 Jul. 28, 2011

(51) Int. Cl.
| | |
|---|---|
| G05B 11/01 | (2006.01) |
| G05B 13/02 | (2006.01) |
| G05B 21/00 | (2006.01) |
| B28C 5/00 | (2006.01) |
| B28C 5/46 | (2006.01) |
| B28C 7/04 | (2006.01) |
| B28C 5/18 | (2006.01) |
| G06F 11/30 | (2006.01) |
| G21C 17/00 | (2006.01) |

(52) U.S. Cl.
USPC ............. 700/265; 700/19; 700/47; 700/54; 702/183; 702/185; 366/1; 366/2; 366/6; 366/8; 366/16; 366/17; 366/18; 366/19; 366/53; 366/54

(58) Field of Classification Search ........... 700/19, 700/21, 47, 79–80, 266, 275, 54, 265; 702/56, 702/182–183, 185, 188; 366/1–2, 6, 8, 16–19, 366/53–54
See application file for complete search history.

(56) References Cited

U.S. PATENT DOCUMENTS

| | | | |
|---|---|---|---|
| 3,870,465 | A | 3/1975 | Maréchal |
| 4,077,763 | A | 3/1978 | Jäger et al. |
| 4,299,560 | A | 11/1981 | Nakamura et al. |
| 4,498,930 | A | 2/1985 | Rake et al. |
| 4,561,139 | A | 12/1985 | Becka et al. |
| 4,739,714 | A | 4/1988 | LaSpisa et al. |
| 4,794,870 | A | 1/1989 | Visvesvaraya |
| 5,040,972 | A | 8/1991 | Kleinhenz et al. |
| 5,115,671 | A | 5/1992 | Hicho |
| 5,285,376 | A | 2/1994 | Struger et al. |

(Continued)

FOREIGN PATENT DOCUMENTS

| | | |
|---|---|---|
| EP | 1 186 975 | 3/2002 |
| EP | 1 382 905 | 1/2004 |
| WO | WO 02/22246 | 3/2002 |

OTHER PUBLICATIONS

DLI Engineering Corporation, DLI Watchman® SpriteMAX™, Wireless Machine Condition Assessment System, SpriteMAX Product Info Sheet, 2005; 2 pages.

(Continued)

*Primary Examiner* — Ronald Hartman, Jr.
(74) *Attorney, Agent, or Firm* — Harness, Dickey & Pierce, P.L.C.

(57) ABSTRACT

A system for monitoring plant equipment is provided. Another aspect provides an automated analysis system wherein software instructions operably compare sensor data to predefined valves and determine mechanical problems in multiple machines. In another aspect, a cement manufacturing system includes sensors for sensing movement conditions of cement making machines. A further aspect provides a central computer connected to vibration sensors associated with cement making machines, where software instructions perform real-time comparisons and machine performance determinations, based at least in part on sensed signals.

50 Claims, 66 Drawing Sheets

U.S. PATENT DOCUMENTS

| | | | |
|---|---|---|---|
| 5,852,351 | A | 12/1998 | Canada et al. |
| 5,870,699 | A | 2/1999 | Canada et al. |
| 5,882,190 | A | 3/1999 | Doumet |
| 5,895,857 | A | 4/1999 | Robinson et al. |
| 5,983,165 | A * | 11/1999 | Minnich et al. ............... 702/56 |
| 6,050,813 | A | 4/2000 | Doumet |
| 6,078,874 | A | 6/2000 | Piety et al. |
| 6,138,078 | A | 10/2000 | Canada et al. |
| 6,142,771 | A | 11/2000 | Doumet |
| 6,183,244 | B1 | 2/2001 | Doumet |
| 6,192,325 | B1 | 2/2001 | Piety et al. |
| 6,234,021 | B1 | 5/2001 | Piety et al. |
| 6,297,742 | B1 | 10/2001 | Canada et al. |
| 6,301,514 | B1 | 10/2001 | Canada et al. |
| 6,383,283 | B1 | 5/2002 | Doumet |
| 6,498,992 | B1 | 12/2002 | Toyota et al. |
| 6,529,135 | B1 | 3/2003 | Bowers et al. |
| 6,549,869 | B1 | 4/2003 | Piety et al. |
| 6,598,479 | B1 | 7/2003 | Robinson et al. |
| 6,668,201 | B1 * | 12/2003 | Bonissone et al. .............. 700/50 |
| 6,694,285 | B1 | 2/2004 | Choe et al. |
| 6,790,034 | B1 | 9/2004 | Kearns et al. |
| 6,805,478 | B2 * | 10/2004 | Aizawa et al. .................... 366/1 |
| 6,839,660 | B2 | 1/2005 | Eryurek et al. |
| 6,876,904 | B2 * | 4/2005 | Oberg et al. .................. 700/265 |
| 6,915,235 | B2 | 7/2005 | Reeves et al. |
| 7,010,445 | B2 | 3/2006 | Battenberg et al. |
| 7,142,990 | B2 | 11/2006 | Bouse et al. |
| 7,231,303 | B2 | 6/2007 | Griessler et al. |
| 7,233,830 | B1 | 6/2007 | Callaghan et al. |
| 7,308,339 | B2 * | 12/2007 | Bonissone et al. ........... 700/265 |
| 7,409,760 | B2 | 8/2008 | Mauer et al. |
| 7,536,278 | B2 | 5/2009 | Mian et al. |
| 7,539,549 | B1 | 5/2009 | Discenzo et al. |
| 7,551,982 | B2 * | 6/2009 | Hammerling ................. 700/265 |
| 7,591,440 | B2 * | 9/2009 | Morrow et al. ............... 241/171 |
| 7,924,414 | B2 * | 4/2011 | Mound ........................... 356/73 |
| 2002/0035495 | A1 * | 3/2002 | Spira et al. ......................... 705/7 |
| 2002/0191481 | A1 * | 12/2002 | Cox et al. ......................... 366/16 |
| 2003/0060993 | A1 * | 3/2003 | Russell et al. .................. 702/84 |
| 2004/0138765 | A1 * | 7/2004 | Bonissone et al. .............. 700/31 |
| 2005/0132933 | A1 * | 6/2005 | Blum ............................ 106/739 |
| 2005/0155429 | A1 * | 7/2005 | Griessler et al. ................ 73/593 |
| 2005/0159843 | A1 * | 7/2005 | Oberg et al. .................. 700/265 |
| 2007/0064762 | A1 | 3/2007 | Hammerling |
| 2007/0093926 | A1 | 4/2007 | D. Braun et al. |
| 2008/0028988 | A1 | 2/2008 | Welker |
| 2008/0249729 | A1 | 10/2008 | Martinez et al. |
| 2009/0133607 | A1 | 5/2009 | Hansen |
| 2009/0177313 | A1 * | 7/2009 | Heller et al. .................. 700/216 |
| 2009/0292572 | A1 * | 11/2009 | Alden et al. ....................... 705/7 |
| 2011/0166689 | A1 * | 7/2011 | Alden et al. .................. 700/108 |

OTHER PUBLICATIONS

DLI Engineering Corporation, DLI Online Client Software, Summary of User Software and Capabilities, SpriteMAX Client Software Product Sheet, 2006; 2 pages.

Emerson Process Management, CSI 4500 Machinery Health™ Monitor, Machinery Health™ Management, Product Data Sheet 0-4500-091306, www.assetweb.com , Sep. 2006; pp. 1-16.

Henningsen, Arne et al.; "Intelligent Alarm Handling in Cement Plants—Lessons Learned From the Nuclear Industry;" IEEE, 0-7803-0960-x/93, 1993; pp. 165-182.

Blaney, John; "Communication, Protection and Diagnostics for Cement Power Systems.;" IEEE, 0-7803-0960-x/93, 1993; pp. 85-102.

Iannello, Victor; "Slimmed-Down Magnetic-Bearing Systems Fit More Rotating Machinery Applications;" published on *Machine Design*, http://machinedesign.com, location of publication http://machinedesign.com/print/82237, Oct. 5, 2009; 5 pages.

Peshek, Clifford et al.; "Recent Developments and Future Trends in PLC Programming Languages and Programming Tools for Real-Time Control;" Prepared for the IEEE Cement Industry Technical Conference in Toronto, Canada, 0-7803-0960-X/93, May 1993; pp. 219-230.

McCarthy, Jr. et al.; "Power Monitoring Devices: Trends in Power Automation;" Prepared for the IEEE Cement Industry Technical Conference in Toronto, Canada, Record of Conference Papers, 35th IEEE, May 23-27, 1993; pp. 57-63.

Hall, Maynard; "Kiln Stabilization and Control—A COMDALE/C Expert System Approach;" Presented at the IEEE Cement Technical Conference in Toronto, Canada, May 1993; pp. 201-218.

Ehinger, Stanton et al.; "A Kiln Drive Vibration Problem & Solution;" Prepared for Presentation at the IEEE Cement Industry Technical Conference in Toronto, Canada, May 23-27, 1993; pp. 141-152.

Fenton, Dennis; "Lateral Vibrations, Causes and Some Solutions;" Presented at the 35th IEEE Cement Industry Technical Conference in Toronto, Canada, Record of Conference Papers, May 23-27, 1993; pp. 105-132.

Emerson Process Management, Machinery Health™ Management, "CSI 9420 Wireless Machinery Health Transmitter;" Product Data Sheet O-9420-121807, www.assetweb.com/mhm, Dec. 2007; 10 pages.

Holcim, Cement Production, http://www.holcim.com/holcimweb/gc/CORP/flash/EN/cementos_en.html, Sep. 1, 2009; 7 pages.

Young, Jonathan C., "Vibration Analysis Using a MEMS Accelerometer;" Presented as Thesis at Naval Postgraduate School, Monterey, California, Dec. 2006; 61 pages.

Instruction Manual, Universal Vibration Meter VM15, published by Metra Mess- und Frequenztechnik Radebeul, Radebuel, Germany, www.MMF.de, 2002, 24 pages.

Instruction Manual, Vibration Severity Meter VM12, published by Metra Mess- und Frequenztechnik Radebeul, Radebuel, Germany, www.MMF.de, 2006, 20 pages.

Jäger Von G., et al.; "Zementwerksautomation—gegenwärtiger Stand und Anwendungsspektrum, Teil 1" (English translation of title: "Cement Works Automation—current situation and range of applications, Part I;")—English translation of Summary, ZKG International, vol. 48/vol. 84, No. 10/95, ISSN 0949-0205, 1995; pp. 509-524.

Jäger Von G., et al.; English Abstract of Publication—"Cement Works Automation—Current Situation and Range of Applications.1.;" ZEMENT-KALK-GIPS, vol. 48, No. 10, ISSN: 0722-4400, 1995; pp. 509.

Häfner, Hans et al.; "Optimized Process Control of Rotary Kilns With Rotor Weightfeeders;" World Cement, vol. 24, No. 12, Dec. 1993; pp. 11-19.

Häfner, Hans et al.; English Abstract of Publication—"Optimized Process Control of Rotary Kilns With Rotor Weightfeeders;" World Cement, vol. 24, No. 12, WOCEDR ISSN: 0263-6050, Dec. 1993; 7 pages.

Barton, Von F.-J.; "Einsatz eines Prozeßleitsystems für die neue Zementmahl-anlage im Werk Neubeckum der Dyckerhoff AG;" English translation of Summary, ZEMENT-KALK-GIIPS, vol. 45, No. 12, ISSN 0722-4397/ISSN 0722-4400 (Edition B), Dec. 1992; pp. 642-647.

Barton, Von F.-J.; English Abstract of Publication—"Einsatz eines Prozeßleitsystems für die neue Zementmahl-anlage im Werk Neubeckum der Dyckerhoff AG;" (English translation of title: "The Use of a Process Control System for the New Cement Grinding Plant At Dyckerhoff AG's Neubeckum Works;") ZKG International, vol. 45, No. 12, ISSN 0722-4397, Dec. 1992; pp. 642-647.

* cited by examiner

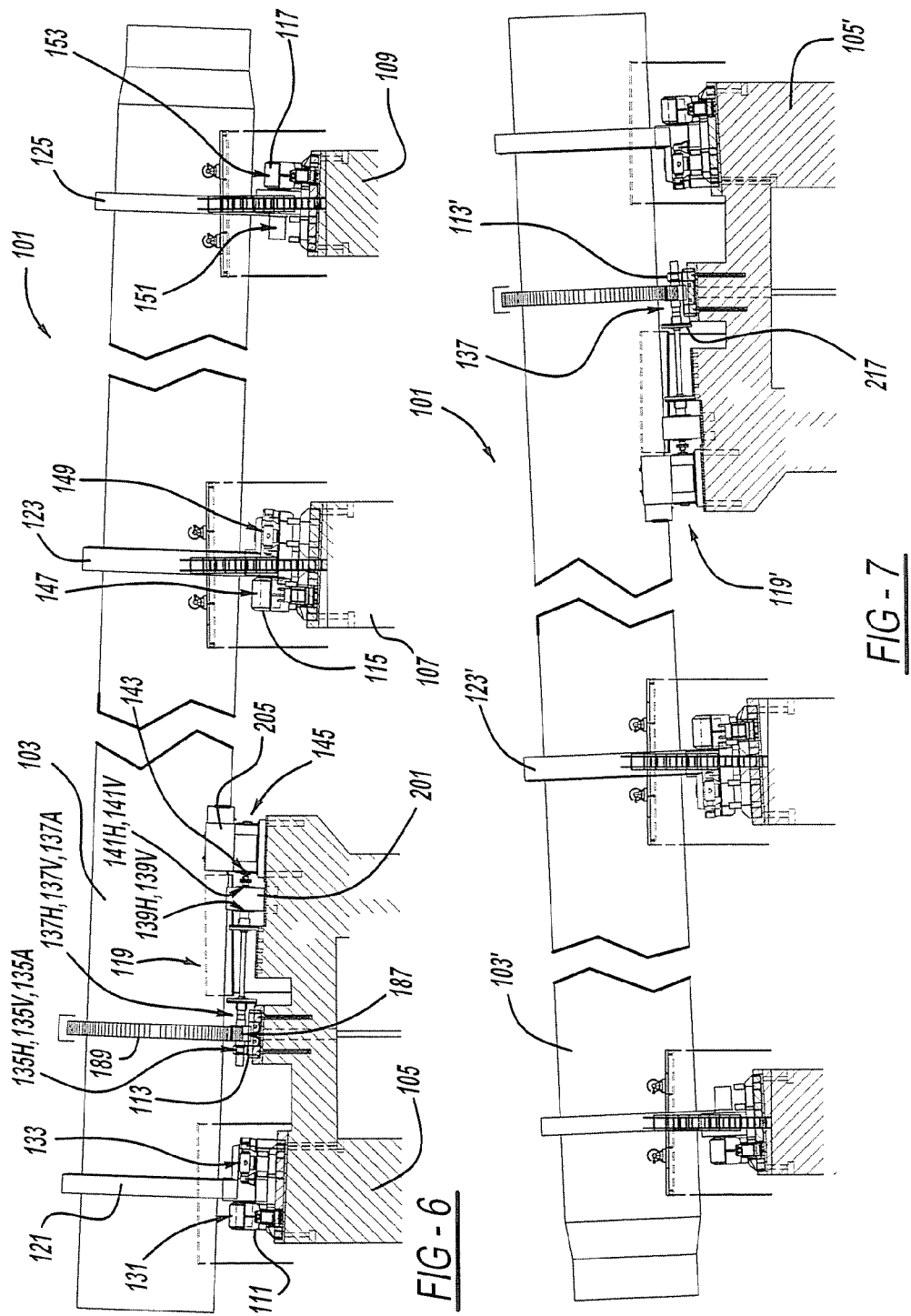

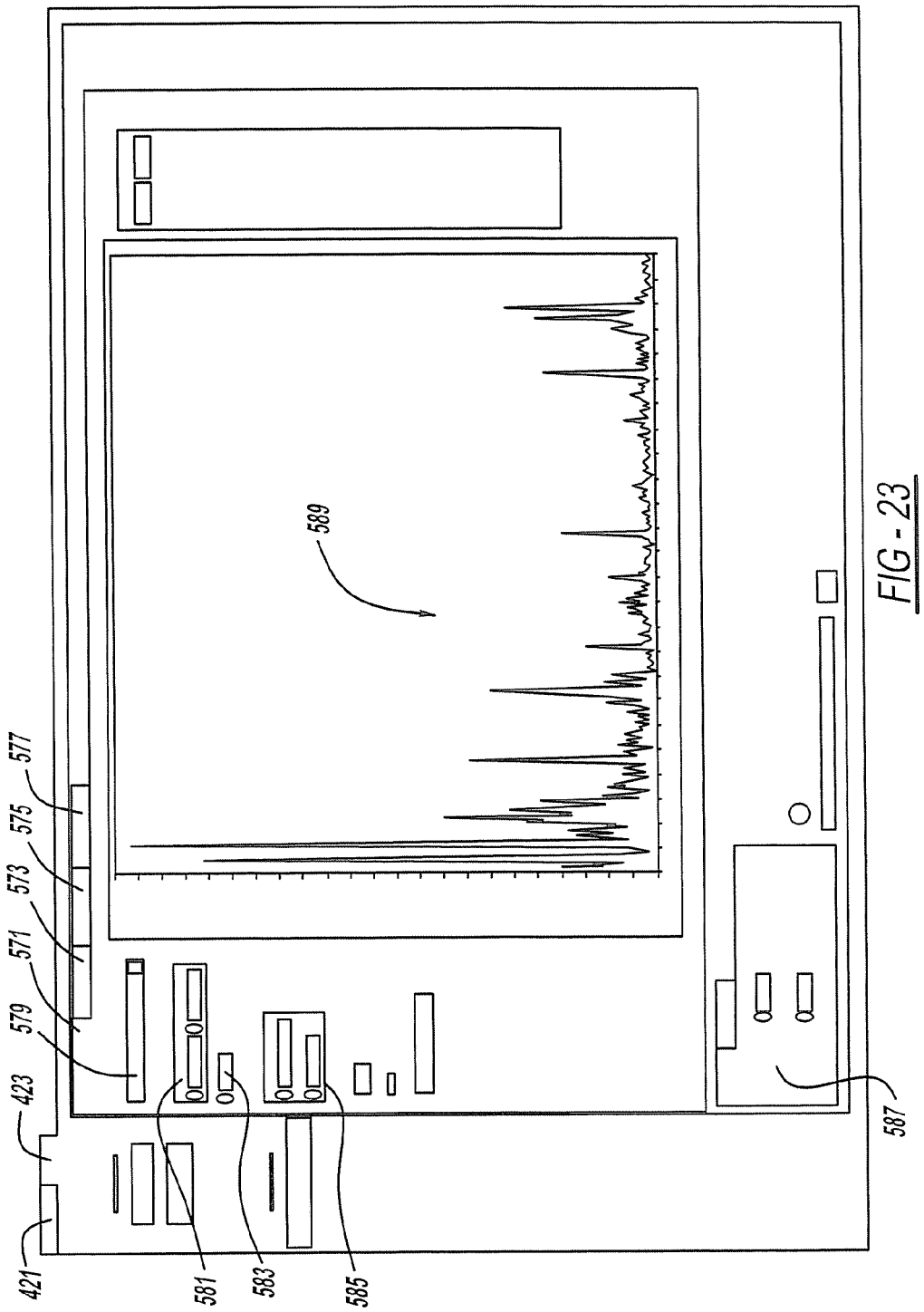

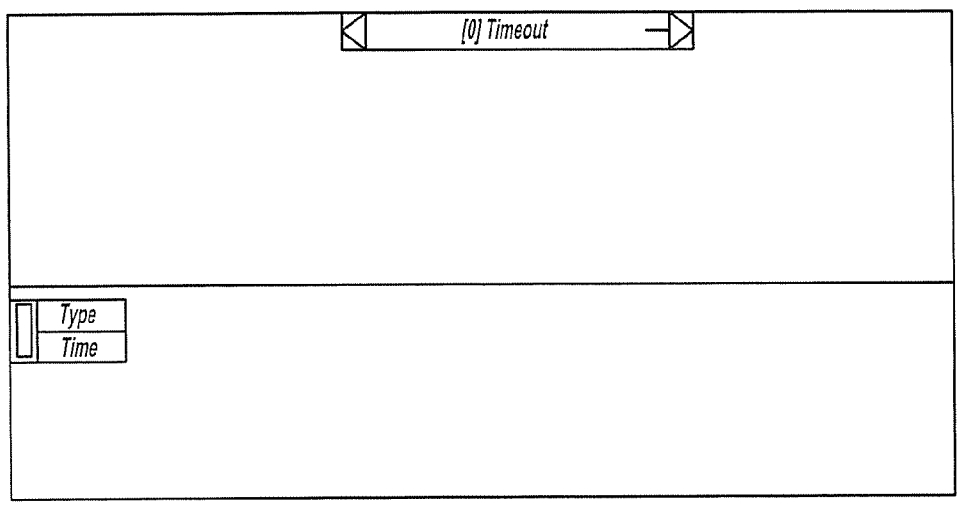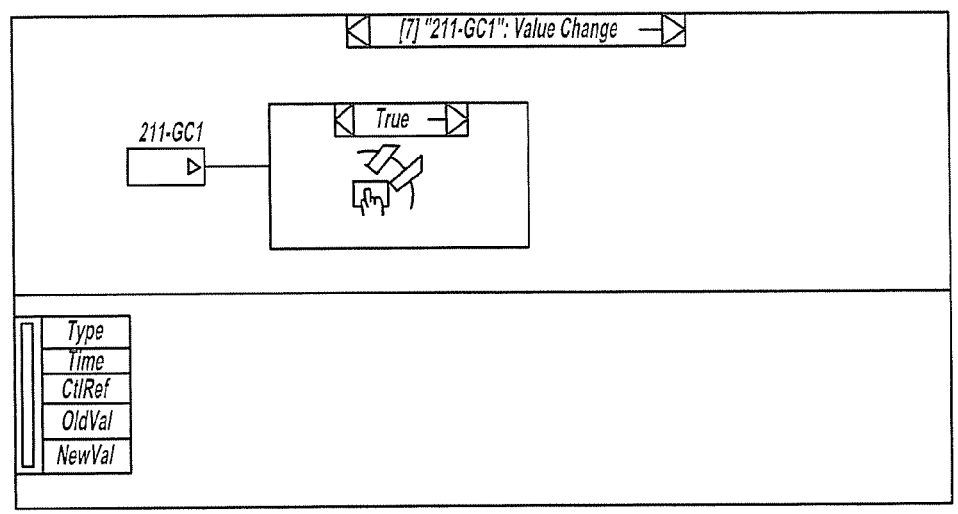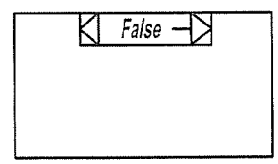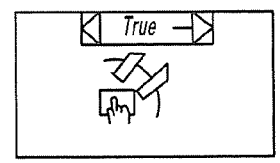
FIG - 30C-3

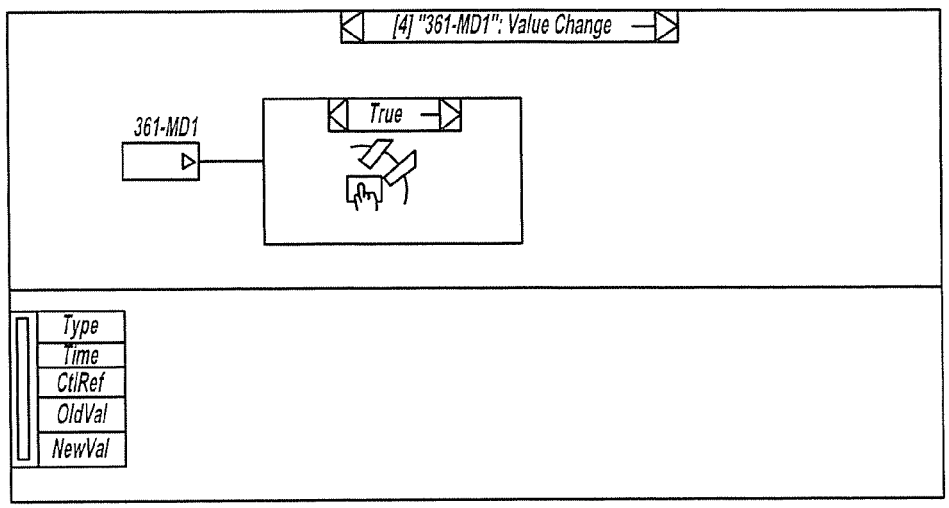
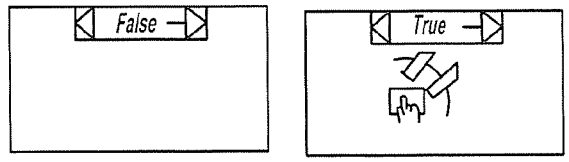
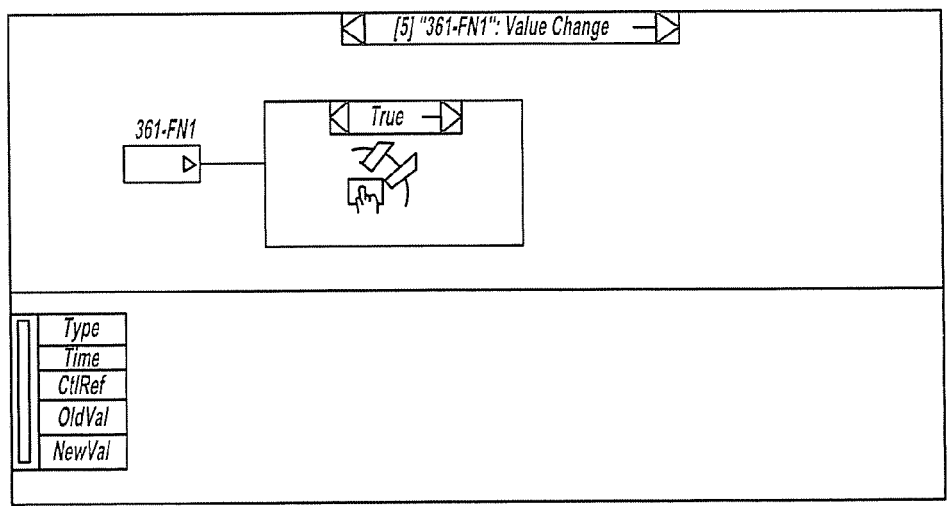
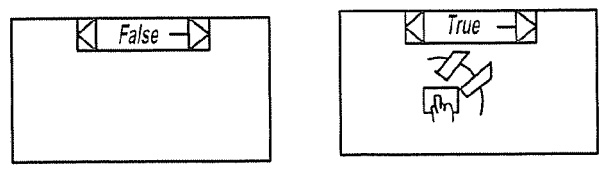
FIG - 30D-2

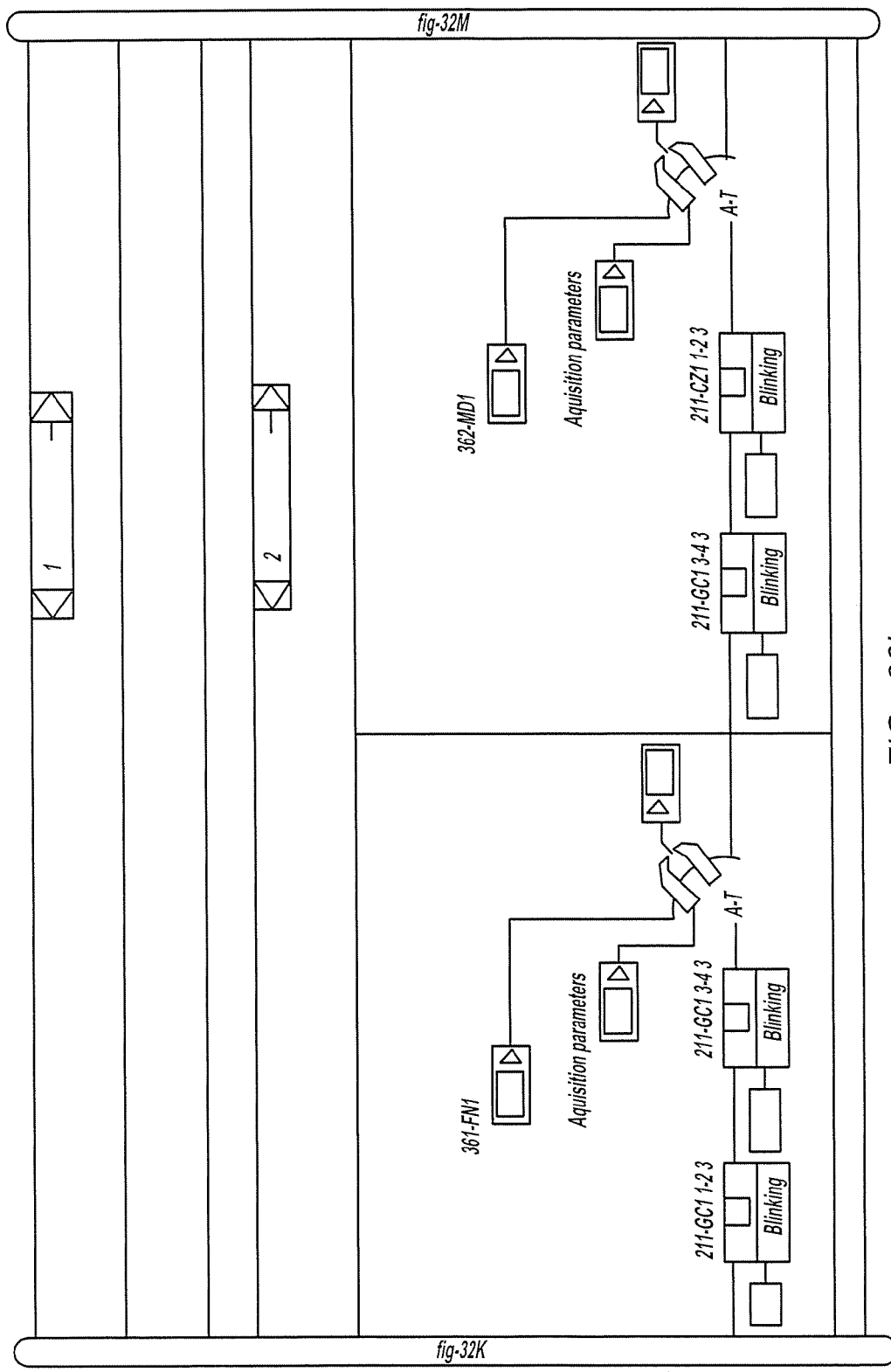

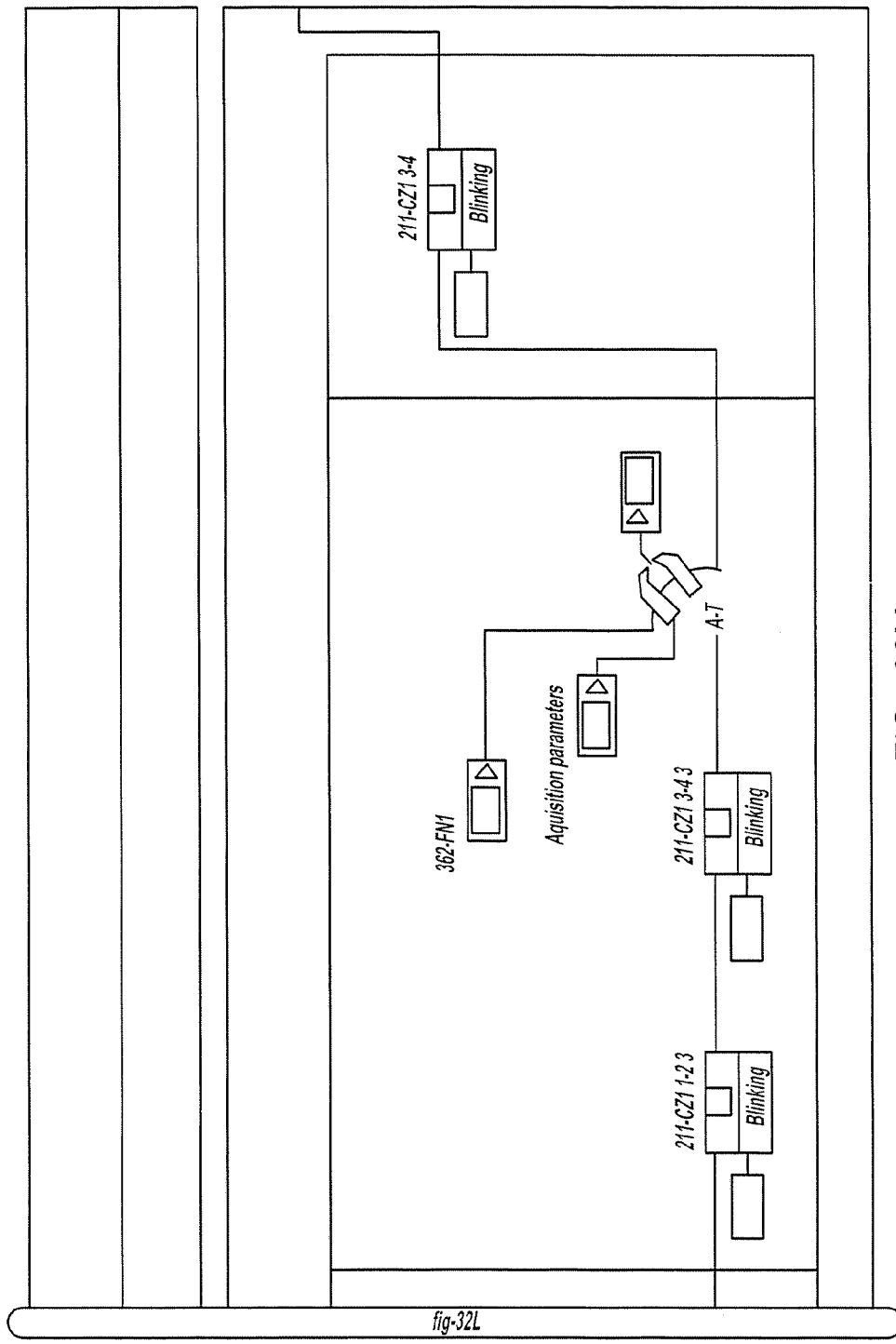

SYSTEM FOR MONITORING PLANT EQUIPMENT

BACKGROUND AND SUMMARY

This disclosure relates generally to manufacturing equipment and more particularly to a system for monitoring manufacturing plant machinery.

Various diagnostic devices are known which monitor or determine a fault in general purpose machinery. Examples of this can be found in the following U.S. Pat. No. 7,010,445 entitled "Automated Fault Diagnosis Device and Method" which issued to Battenberg et al. on Mar. 7, 2006; U.S. Pat. No. 6,549,869 entitled "Expert Analysis Modules for Machine Testing" which issued to Piety et al. on Apr. 15, 2003; U.S. Pat. No. 6,839,660 entitled "On-Line Rotating Equipment Monitoring Device" which issued to Eryurek on Jan. 4, 2005; and U.S. Pat. No. 7,539,549 entitled "Motorized System Integrated Control and Diagnostics Using Vibration, Pressure, Temperature, Speed, and/or Current Analysis" which issued to Discenzo et al. on May 26, 2009. All of these patents are incorporated by reference herein. These conventional devices also typically employ a rigid set of programmed rules to determine health of the machine.

In cement manufacturing plants, machine performance is typically monitored by one or more technicians physically walking or driving from machine to machine and either visually observing operating performance at various points for each machine or collecting sensor data through a hand-held data collector at each machine during the walk by inspection. Some of these machines may be at least one mile away from each other. The collected data is subsequently downloaded to an off-line database for later analysis by an operator. This physical walk by monitoring is very time consuming and costly, and does not allow for easily managed and timely analysis of the sensed machine data.

Various alarm and temperature fault detection systems have been proposed for use in kiln bearing condition and electric motor monitoring. For example, reference should be made to A. Henningsen et al., "Intelligent Alarm Handling In Cement Plants—Lessons Learned From The Nuclear Industry," IEEE, 0-7803-0960-x/93, p. 165 (1993), and J. Blaney, "Communication, Protection And Diagnostics For Cement Power Systems," IEEE, 0-7803-0960-x/93, p. 85 (1993). These proposed systems, however are very crude and do very little, if any, automatic calculation and analysis of the monitored information. Instead, they rely on the operator to manually analyze the information to determine problem causation which will quickly overload the operator with too much data and prevent real-time monitoring, especially if many machines are involved.

In accordance with the present invention, a system for monitoring plant equipment is provided. Another aspect provides an automated analysis system wherein software instructions operably analyze sensor data and extract specific spectrum related values to determine mechanical problems in multiple machines. In another aspect, a cement manufacturing system includes sensors for sensing vibration conditions of cement making machines. A further aspect provides a central computer connected to vibration sensors associated with cement making machines, where software instructions perform real-time comparisons and machine performance determinations, and/or evolutionary learning calculations, based at least in part on sensed signals. A method of using machines to manufacture cement, including detecting characteristics associated with a machine and then determining if an undesirable machine condition exists, is also provided.

The present invention is advantageous over traditional devices since the present invention allows for essentially instantaneous, real-time data analysis by a centralized computer of the sensed machine operating conditions. This will save significant labor time and expense while also greatly improving the accuracy and timeliness of machine monitoring and maintenance. Certain aspects of the present system also advantageously employ evolutionary learning calculations to improve sensed data analysis and more accurate identification of machine problems. Furthermore, certain aspects of the present system allow for significantly reduced hardware costs by employing a switch matrix and multiplexer computer-to-sensor connection, which inexpensively proves at least 50, and more preferably 64, communication channels. Various aspects of the present system advantageously interface with a hand-held data collector, on-line databases and/or off-line databases, using hard-wired or wireless communications. The present system is ideally suited for use in cement manufacturing machinery, such as cement making kilns, crushers, conveyors, fans and the like. Additional advantages and features of the present invention will become apparent from the following description and appended claims, taken in conjunction with the accompanying drawings.

BRIEF DESCRIPTION OF THE DRAWINGS

FIG. 6 is a side elevational view showing a kiln machine employed in the system;

FIG. 7 is a side elevational view, opposite that of FIG. 6, showing the kiln machine employed in the system;

FIG. 23 is a diagrammatic view showing a computer screen display for a vibration spectrum analysis section of the interface in the system;

FIGS. 30A-1-32M are programming diagrams showing software logic employed in the system.

DETAILED DESCRIPTION OF THE PREFERRED EMBODIMENT

Figure 1:
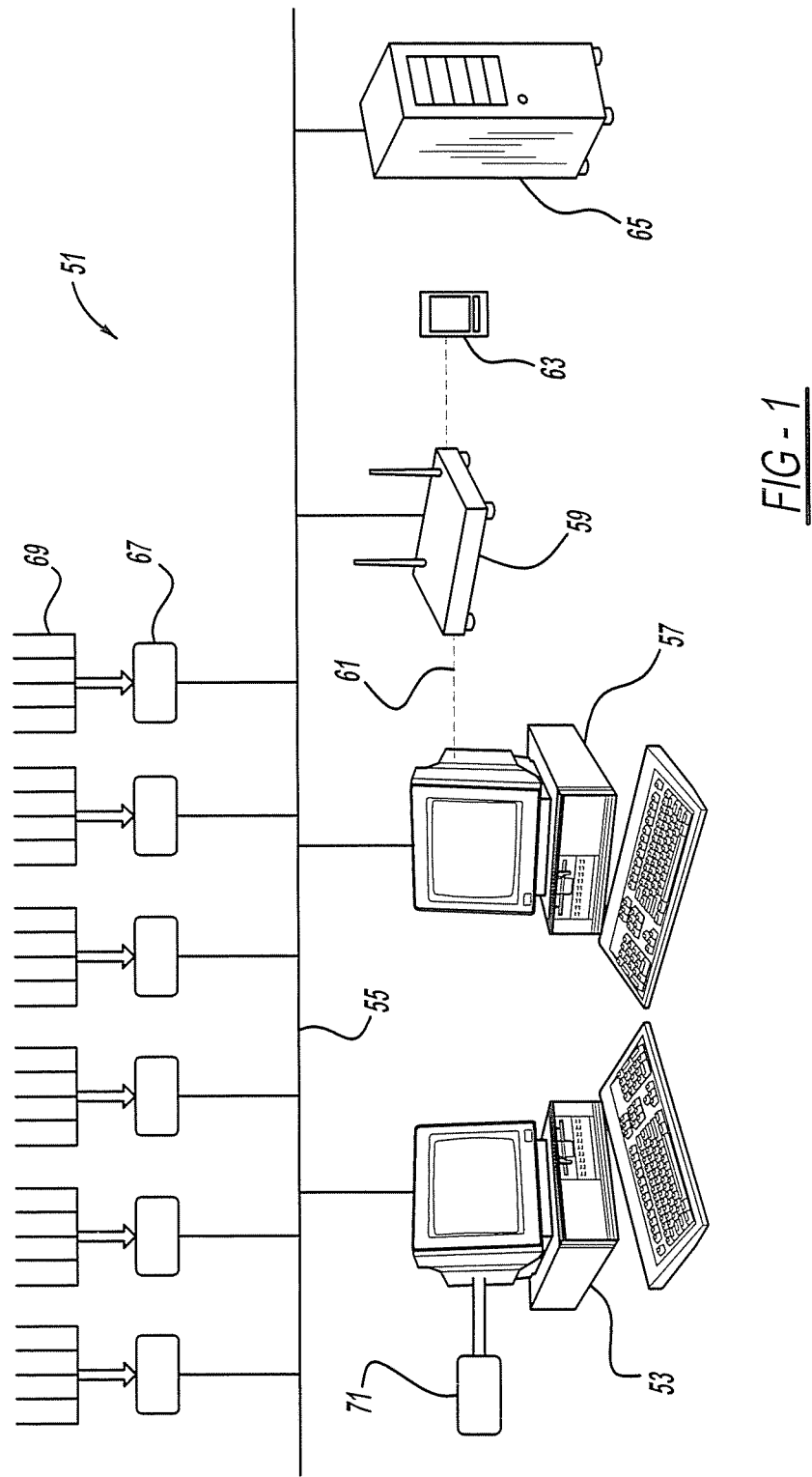
FIG. 1 is a network structure diagram of the preferred embodiment of the present system.

The preferred embodiment of a system for monitoring plant equipment, more preferably cement manufacturing equipment and machinery, may be used to monitor the operating condition of many machines used to make cement, such as Portland cement. In general, the cement manufacturing process begins with extracting raw materials, such as limestone and clay, from a quarry, transporting the materials to crushing machines which reduce the size of the extracted rock, and conveying the crushed rock to grinders. Corrective materials such as iron, minerals and sand are mixed to the crushed material before it enters the raw mills for grinding, drying and pulverizing. The pulverized material is then transported to kiln machines where it is heated until the material forms clinker, which is subsequently cooled by fans. Next, the clinker is transported to storage silos and later sent to clinker grinding mills where it is mixed with gypsum and other materials, whereafter it is transported to storage silos in its final cement form.

The present system employs a computer controller, software and sensor configuration to automate and improve the reporting and analysis of the operation of the many cement manufacturing machines for problem and fault identification, maintenance planning and for historical trend tracking. The present system advantageously minimizes machinery and manufacturing downtime, provides real-time data, improves the quality of data collection and analysis, and significantly reduces the labor, time and cost to collect and analyze the equipment data. More specifically, referring to FIGS. 1 through 5, the present system 51 includes a first computer controller terminal 53 connected to an ethernet communications network 55, and a second computer controller terminal 57 connected to a wireless communications modem 59 via wireless communications 61; the modem is also connected to the ethernet communications network 55. A personal digital assistant ("FDA") controller 63, such as a cellular telephone with e-mail access, is also connected to modem 59 or a cellular telephone tower via wireless communications. A computer server 65 is additionally connected to the ethernet communications network via an ethernet cable.

Figure 3:
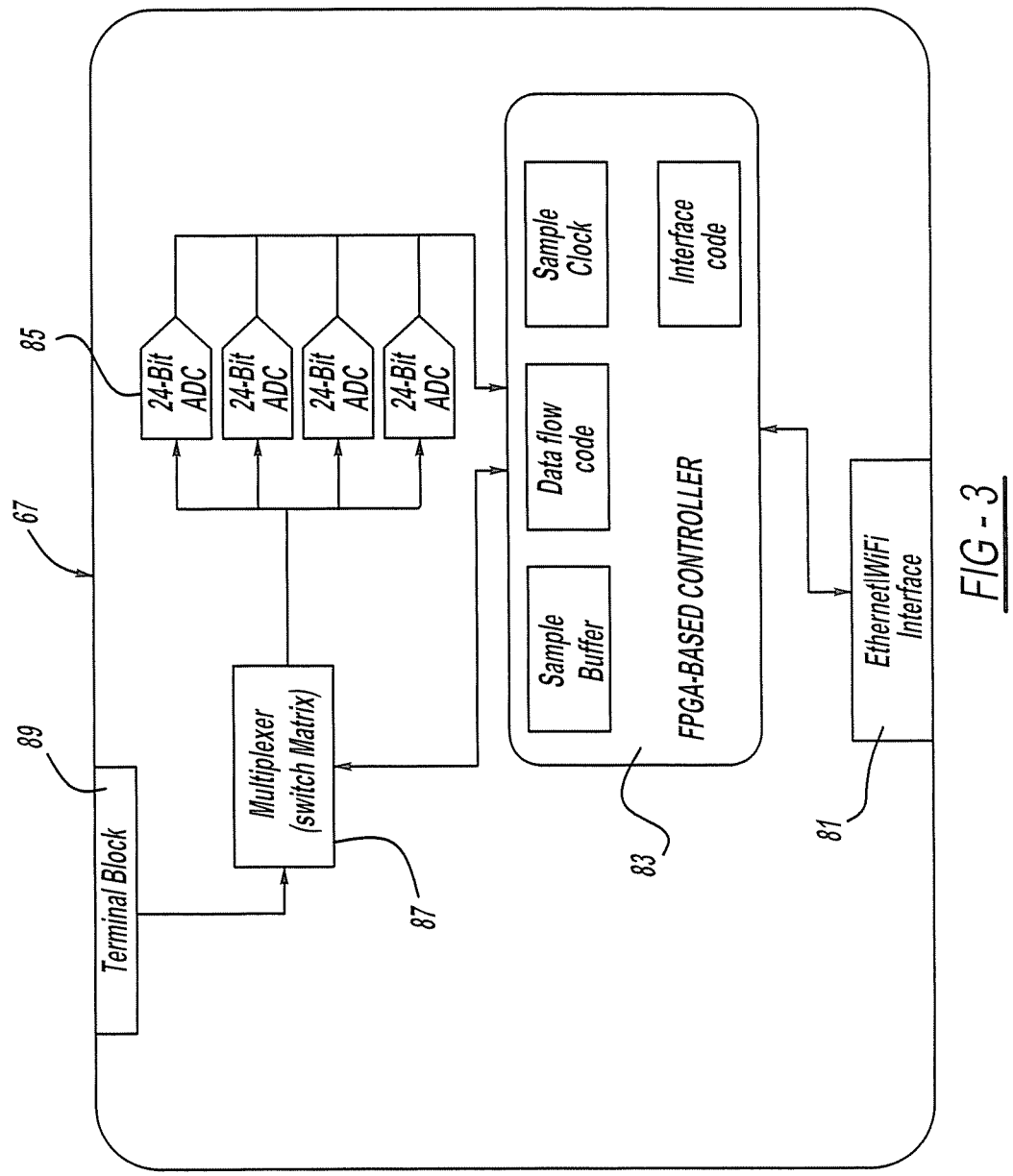
FIG. 3 is an electrical diagram of a signal management box unit employed in the system.
Figure 4:
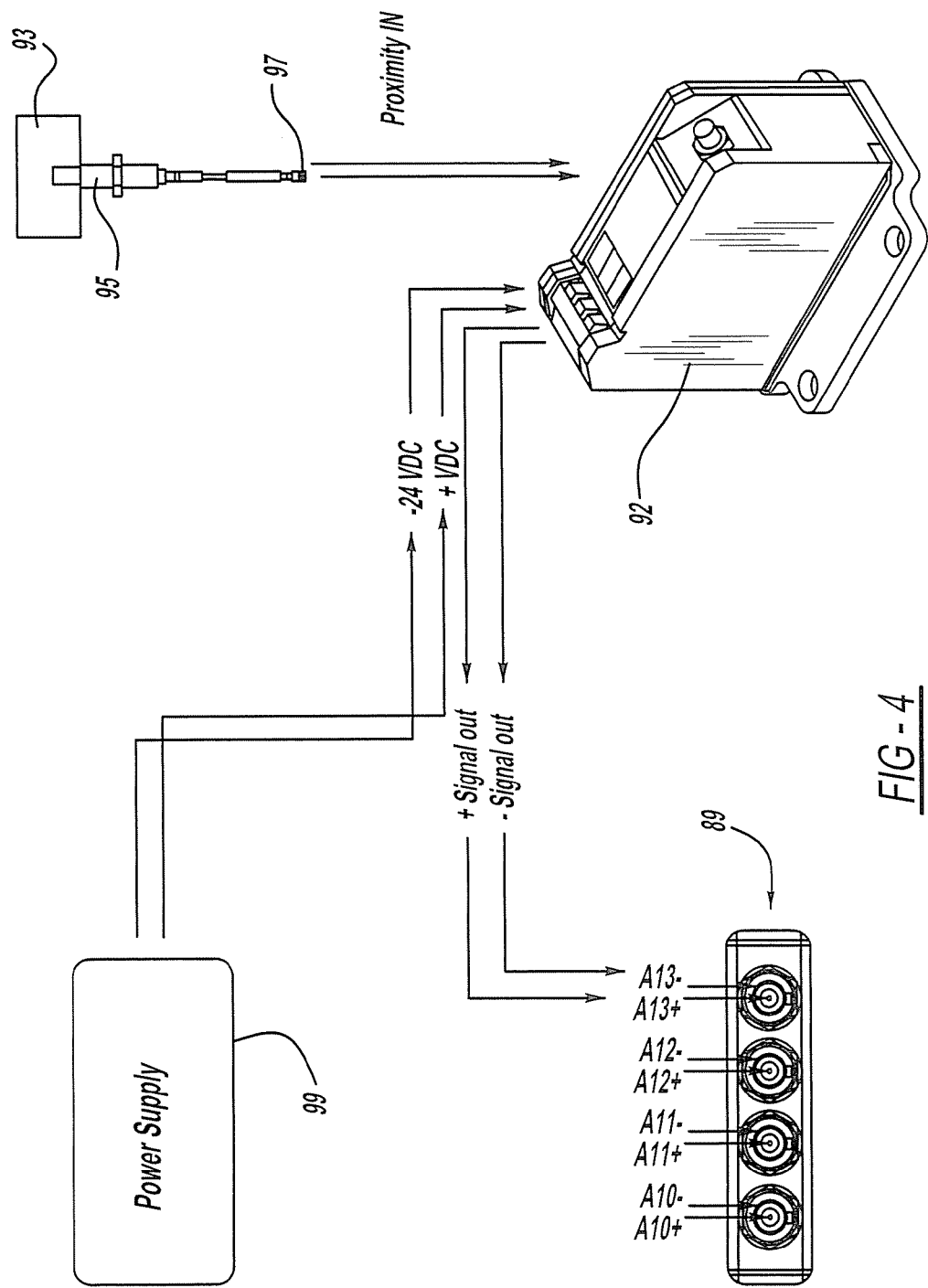
FIG. 4 is an electrical diagram of a proximity sensor interface circuit employed in the system.
Figure 5:
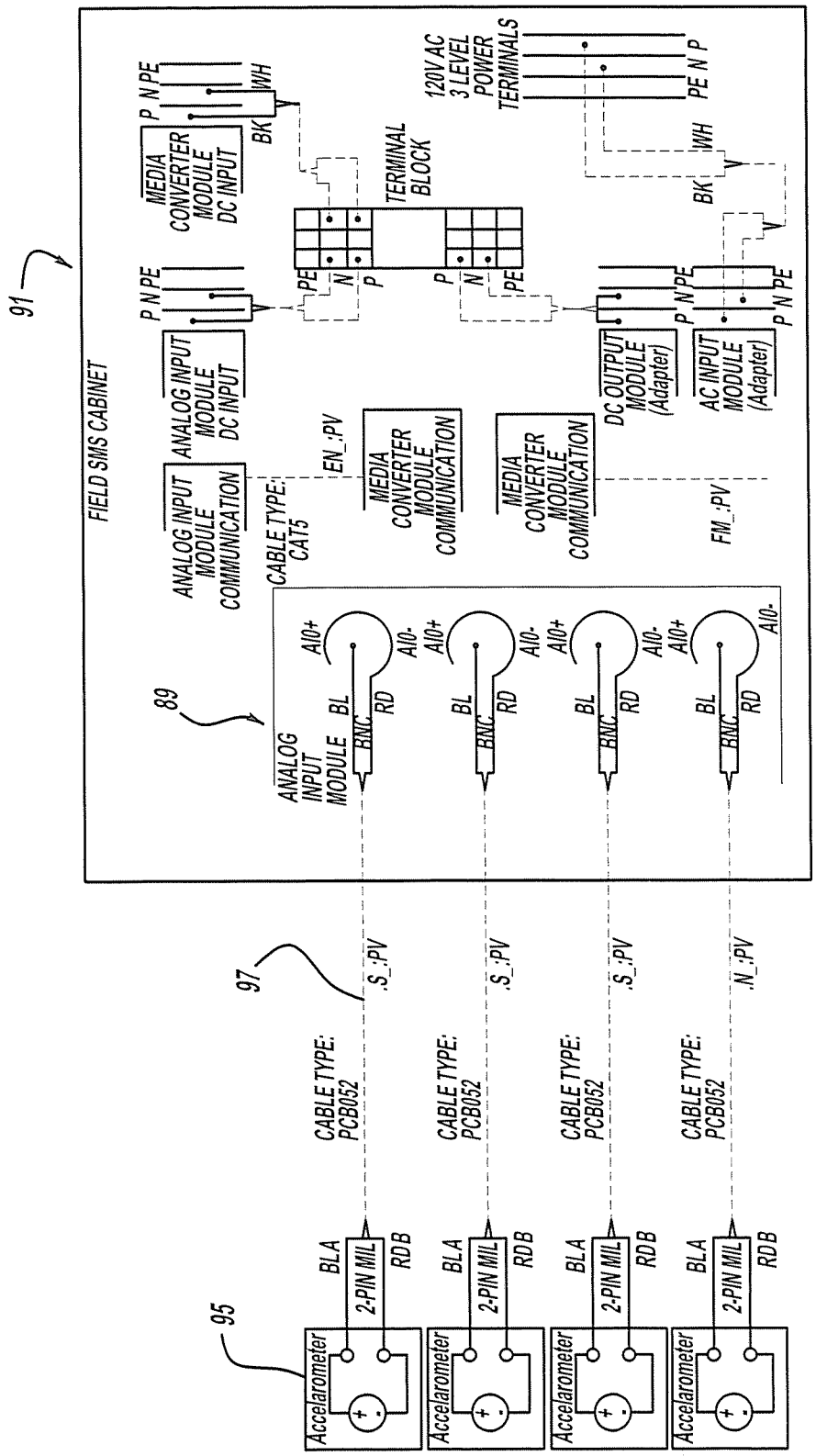
FIG. 5 is an electrical diagram showing an electric power distribution and control cabinet employed in the system.
Figure 8:
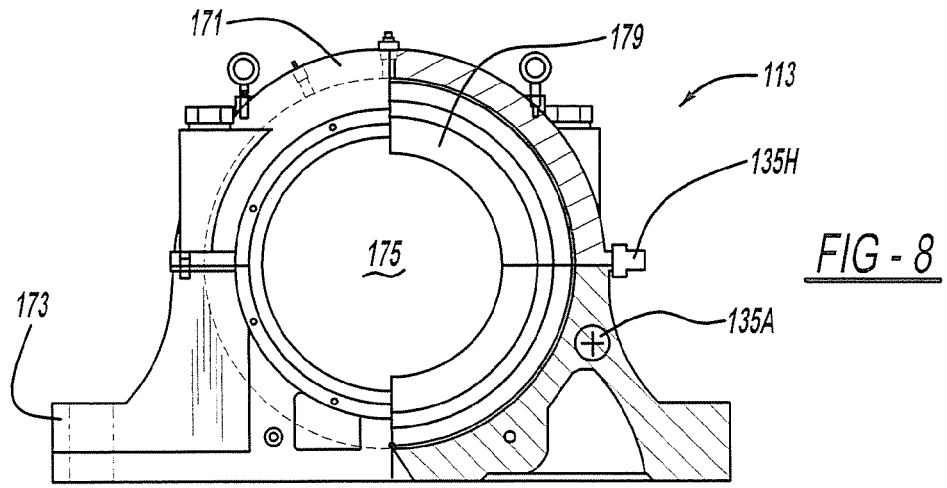
FIG. 8 is a partially fragmented, front elevational view, taken along line 8-8 of FIG. 10, showing a pillow block assembly of the kiln machines employed in the system.
Figure 9:
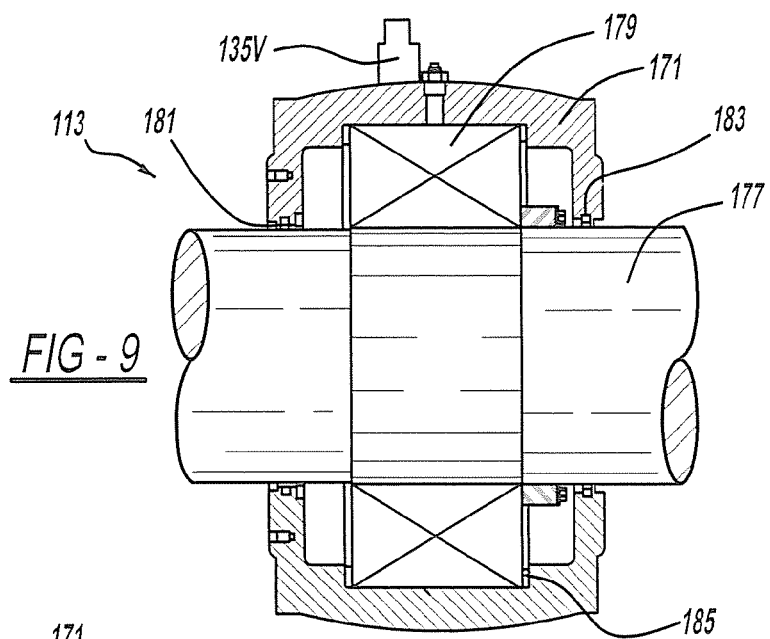
FIG. 9 is a cross-sectional view, showing the pillow block assembly employed in the system.
Figure 10:
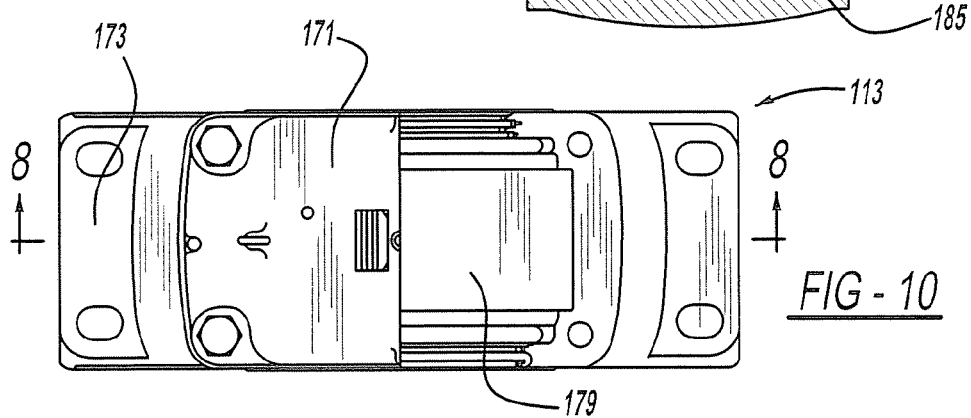
FIG. 10 is a top elevational view showing the pillow block assembly employed in the system.

FIG. 3 illustrates data flow in an FPGA-based data acquisition device. The device receives analog data continuously from accelerometers and then carries out a 24-bit high resolution analog-to-digital conversion. Thereafter, data is sent to the server through either ethernet communication ports or through wireless communications. FPGA-based data acquisition boards 67 are connected to the ethernet communications network via ethernet cables and these boards are connected to associated dynamic signal inputs 69, for example, accelerometers.

Figure 2:
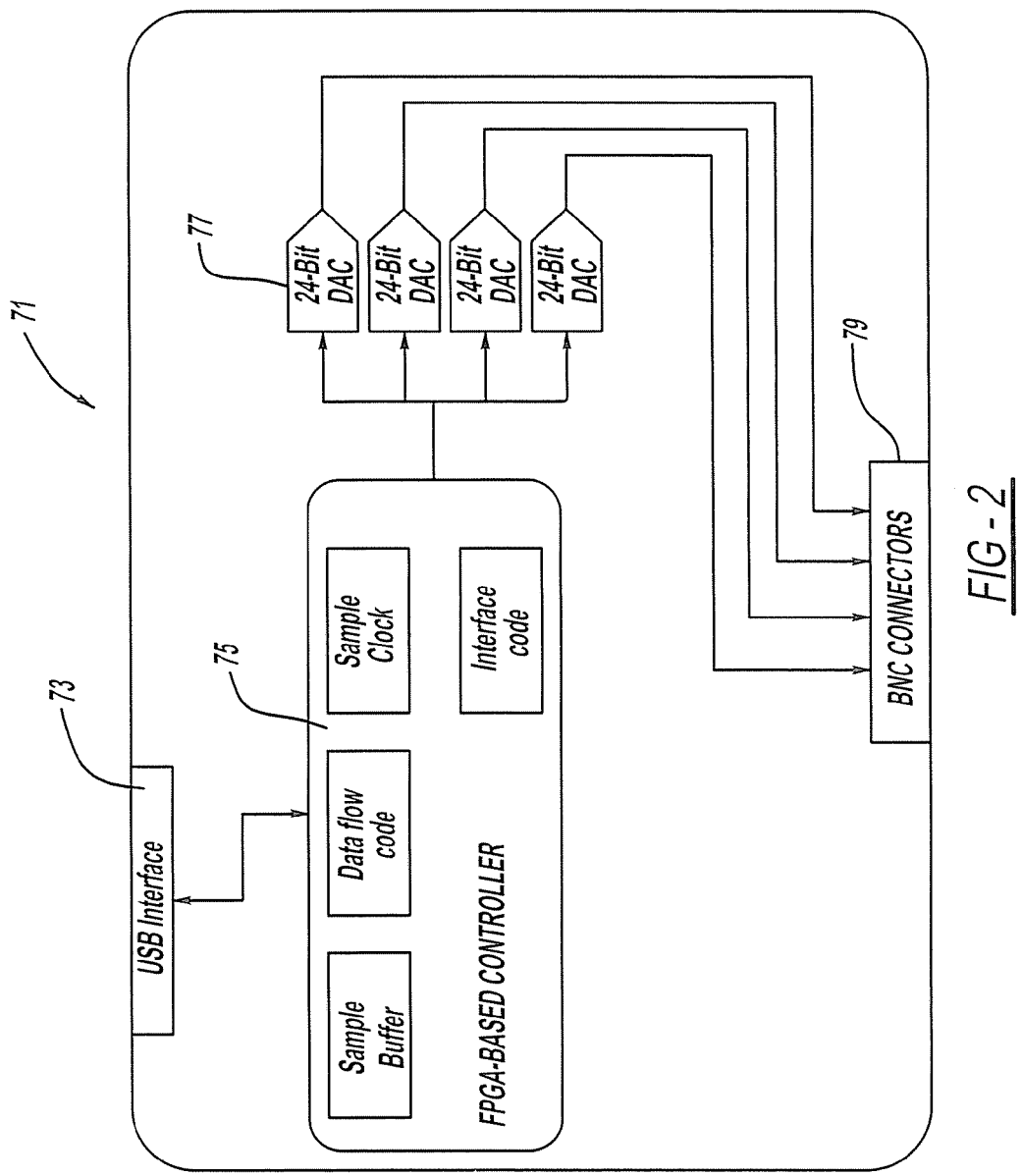
FIG. 2 is an electrical diagram of an FPGA data acquisition board of a central processing unit employed in the system.

FIG. 2 shows data flow from a management box 71 which receives the digital signals from the central computer through any of the computer terminals and then converts the signals back into their original analog form received from the accelerometers. Management box 71 then generates a series of analog data through its BNC output connections, based on a predefined, timed sequence that scans through all measured points in order to simulate the manual data collection process where regular data collectors can connect and acquire data in a point-by-point manner. BNC management box 71 is connected to computer terminal 53 via a USB interface 73. The BNC management box further includes an FPGA-based controller having a sample buffer, data flow code, sample clock and interface code. Multiple 24-bit digital-to-analog converters 77 convert controller 75 outputs to analog form and transmit the signals to BNC connectors 79. There is two way communication between interface 73 and controller 75.

Each FPGA-based data acquisition board 67 includes an ethernet and wireless communications interface 81, an FPGA-based controller 83, multiple 24-bit analog-to-digital converters 85, and a terminal block 89. A multiplexer switch matrix 87 is only utilized where channel count exceeds four monitored locations per machine. Controller 83 further includes a sample buffer, data flow code, sample clock and interface code. Terminal block 89 is connected to a data acquisition device 91 which is mounted within an enclosure attached to the corresponding machine to be monitored. An accelerometer sensor is mounted adjacent a moving component of interest within a corresponding monitored machine 93. For a proximity sensor, there is preferably a 2.5 millimeter gap between the component of the machine being monitored and a tip of sensor 95. A cable 97 connects sensor 95 to a proximitor circuit 92 (see FIG. 4), which powers the sensor and sends the signal to data acquisition device 91. Furthermore, a power supply 99 is connected to and powers the proximity sensor circuitry.

An exemplary real-time and continuously monitored machine includes a pair of kiln drive systems 119 and 119'. These are illustrated in FIGS. 6-10. The kiln 101 includes a rotatable hollow tube 103 through which the raw materials are heated and moved to form clinker, a south side drive system 119 and a north side drive system 119'. Each kiln arrangement further includes piers 105, 107 and 109 upon which are mounted pillow blocks 111, 113, 115 and 117, and the two main drive assemblies 119 and 119'. Supporting slip rings 121, 123 and 125 concentrically surround and move with kiln tube 103 and are engaged by rollers journaled by shafts. Approximately 36 sensors 131-153 are employed to continuously monitor vibration of the kiln arrangement in a real-time manner.

Exemplary pillow block 113 includes a cast and machined iron housing 171 having lateral flanges 173 bolted to pier 105 and a central opening 175 through which extends a shaft 177. A ball bearing assembly 179 is provided within opening 175 of pillow block 113 and rotatably engages the outside diameter surface of shaft 177. Additional ring seals 181, O-rings 183, and stabilizer rings 185 are provided. Oil is provided within pillow block 113. Shaft 177 rotatably drives a small pinion gear 187 which, in turn, drives the much larger girth gear 189 affixed around an outer surface of tube 103. Of particular note, sensor 135H designates a substantially horizontally oriented and enlongated accelerometer, 135A designates a substantially axially oriented and elongated accelerometer and 135V designates a substantially vertically oriented and elongated accelerometer, which all sense and detect vibrations from the bearing 179, shaft 177 and associated gears 187 and 189.

Figure 11:
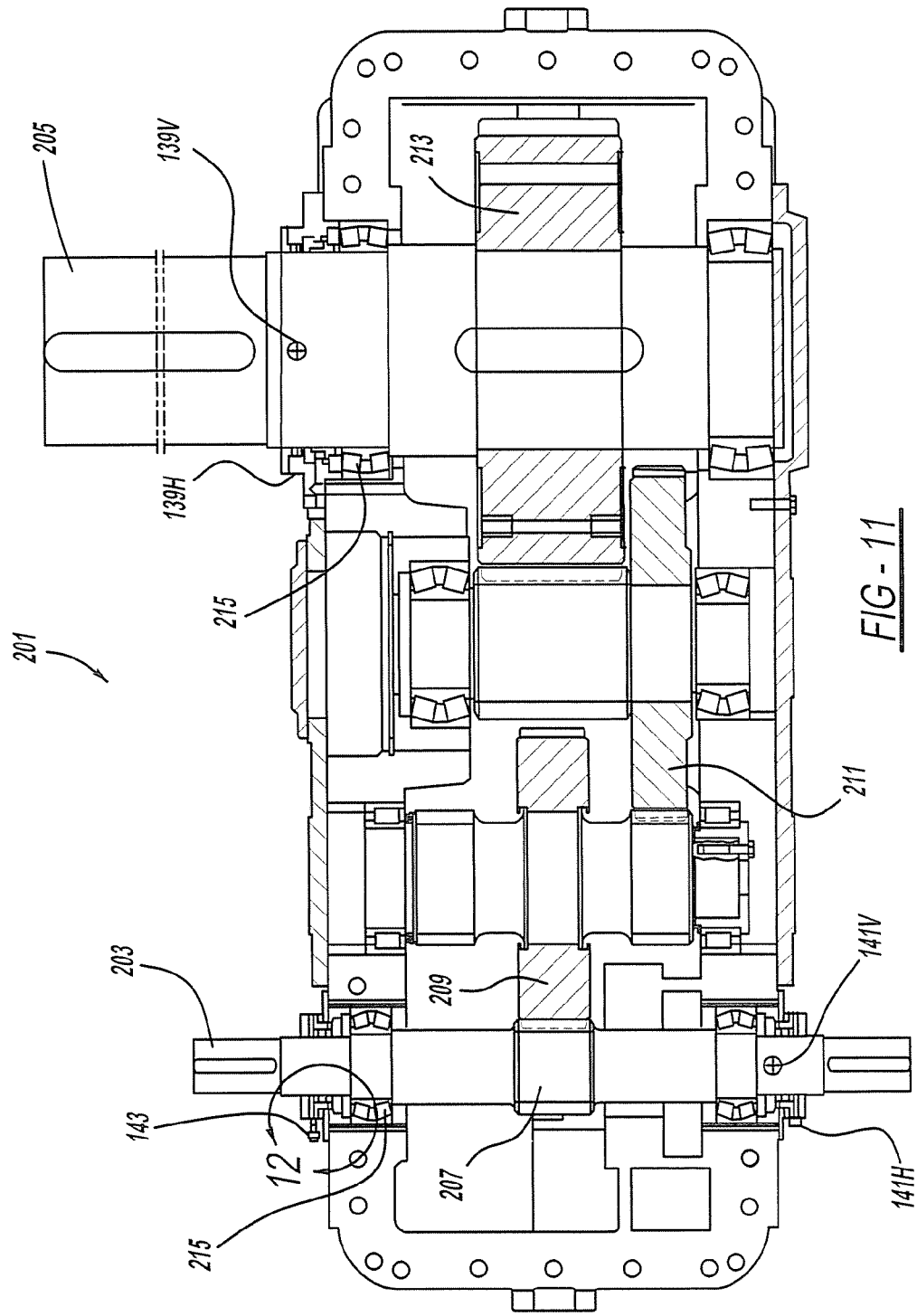
FIG. 11 is a partially fragmented, top elevational view showing a transmission gear box of the kiln machines employed in the system.
Figure 12:
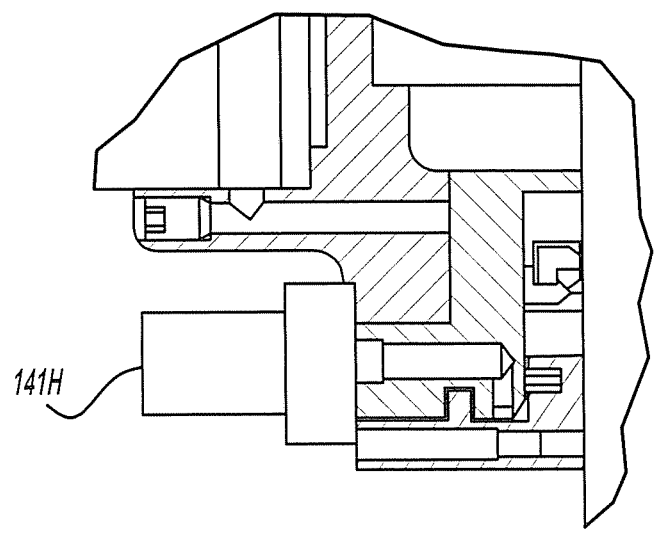
FIG. 12 is an enlarged, partially fragmented view, taken within circle 12 of FIG. 11, showing a portion of the gear box employed in the system.

A gear box 201 of each main drive assembly 119 and 119' is best shown in FIGS. 11 and 12. Gear box 201 includes an input shaft 203 connecting to and rotatably driven by an armature of an electric motor 205 (see FIG. 6). Input shaft 203 rotatably drives and rotates an output shaft 205 through a set of interengaging gears 207, 209, 211 and 213 of different ratios. Each shaft associated with gears 207-213 have at least a pair of associated bearing assemblies 215. Accordingly, sensor 141H is a substantially horizontally oriented accelerometer, sensor 141V is a substantially vertically oriented accelerometer, sensor 139H is a substantially horizontally aligned accelerometer, sensor 139V is a substantially vertically aligned accelerometer, and sensor 143 is a substantially horizontally aligned accelerometer, which all sense and detect vibrational characteristics of the adjacent shaft, bearings and gears, when the components of the gear box are rotated. Most of the other sensors for kilns 101 and 103 are also rotational vibration accelerometer sensors, however, it is alternately envisioned that temperature sensors and electric motor voltage and/or current sensors may optionally be employed.

Each of the accelerometer sensors associated with the pillow blocks provide high sampling rates with a qualitative signal. For example, at least 1,000 analog samples are sensed per second from each sensor, and more preferably, the samples are sensed and sent approximately 16,000 per second. As will be discussed in more detail hereinafter, the central processing unit and software therein use a signal sent by the sensors to determine defects or potential maintenance problems in the corresponding bearings, gears, shaft and other rotating machinery. This information also allows the computer software to determine if there is undesired looseness in the moving parts or if there is too much friction caused by insufficient lubricant.

Moreover, a torque sensor and/or strain gauge is disposed between each coupling disc 217 (see FIG. 6) and the corresponding accelerometer vibration sensor 137. The disc torque sensor measures the torque of the connecting shaft, and torsional vibration can be automatically determined by the software. Thus, the relative difference between kilns drives 119 and 119' can be determined by comparing their respective torsional vibration since the same torque is desired.

Figure 13:
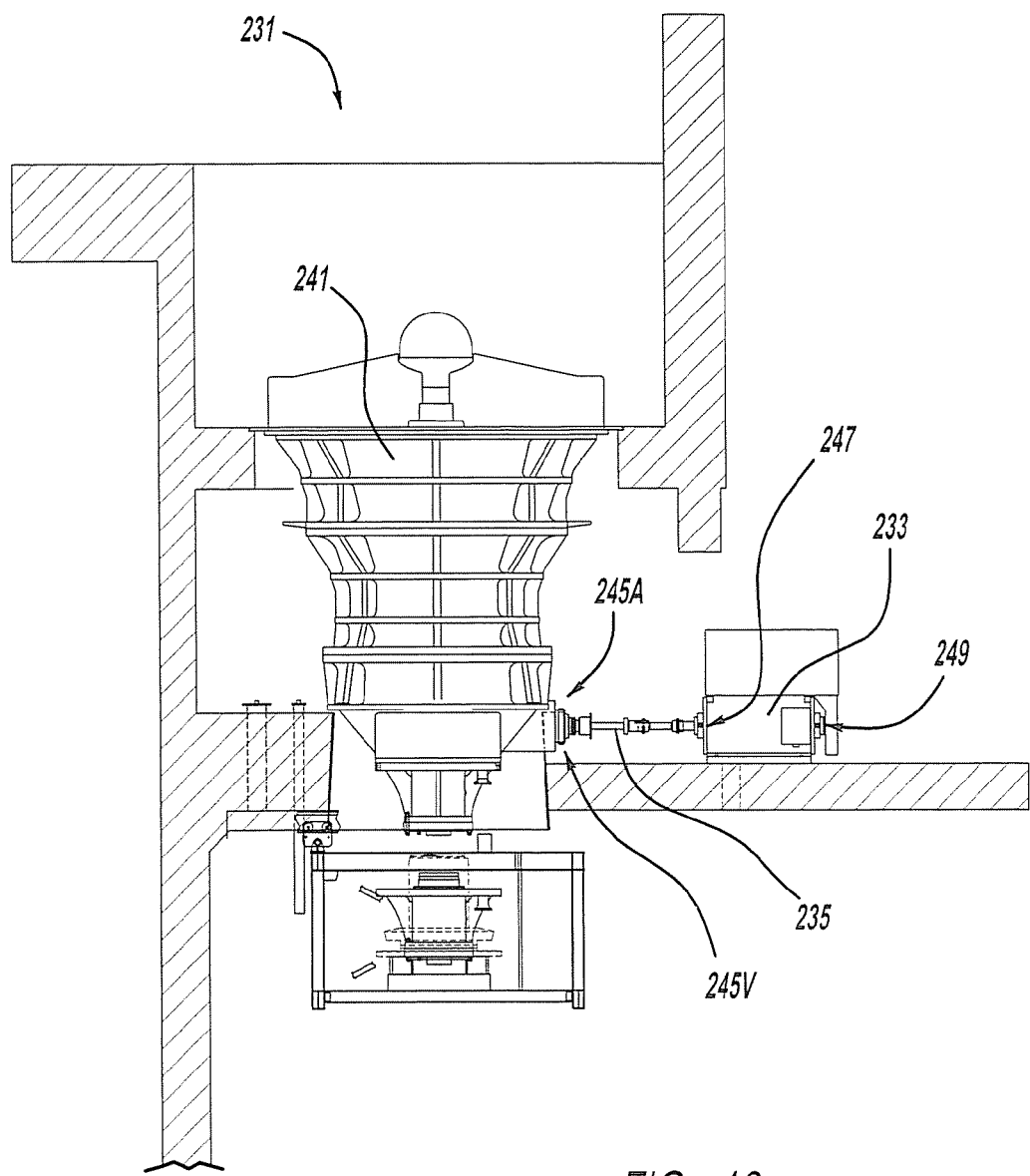
FIG. 13 is a partially fragmented side elevational view showing a crusher machine employed in the system.
Figure 18:
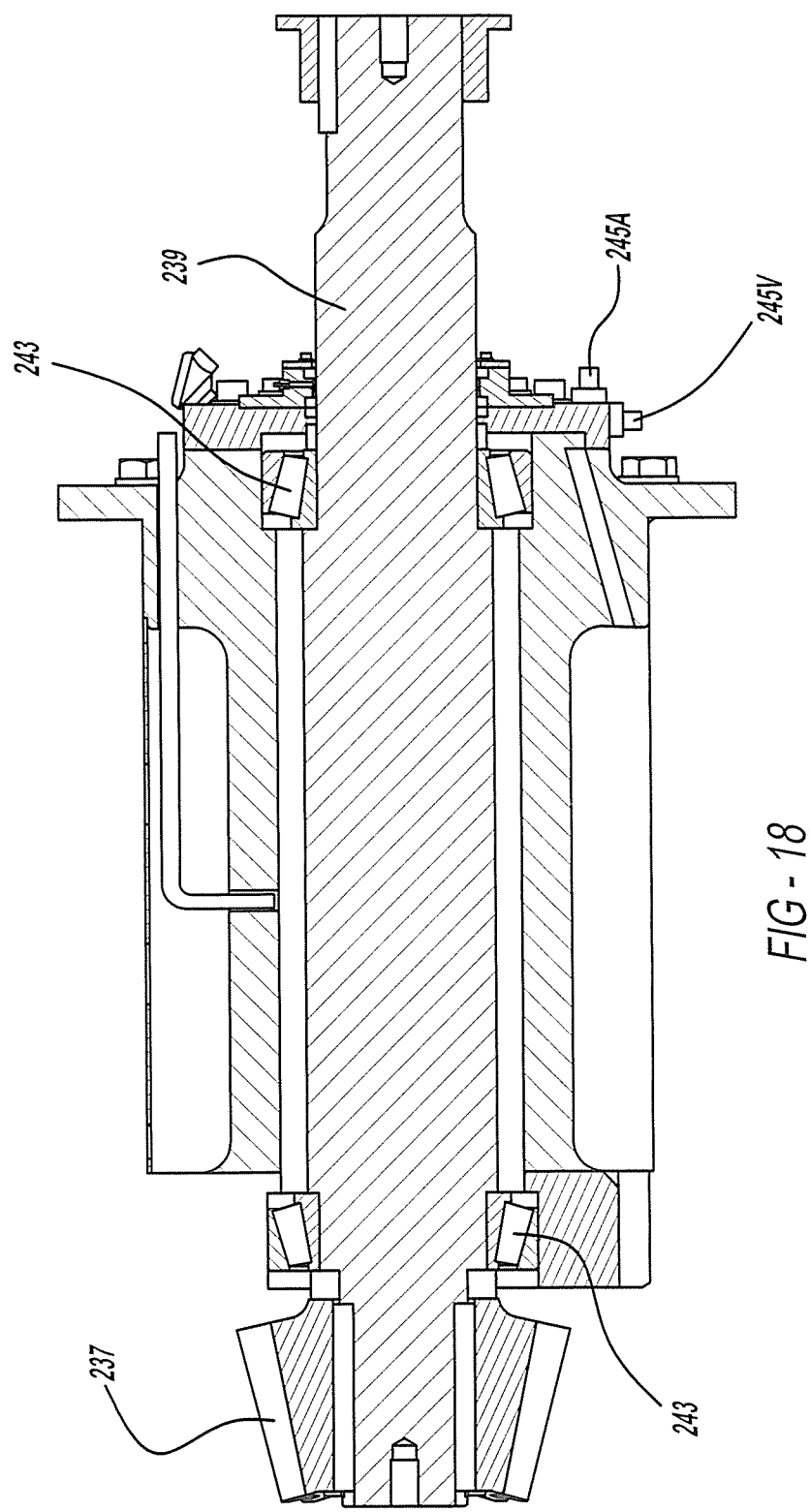
FIG. 18 is an enlarged and partially fragmented view showing an input shaft assembly for the crusher machine of FIG. 13.

FIGS. 13 and 18 illustrate a crusher machine 231 employed prior to the kiln. An electric motor 233 operably rotates a set of shafts 235 through various couplings and gears 237, which in turn rotate a crusher input shaft 239. A crushing roller or other such member is rotated by input shaft 239 in order to reduce the size of the raw limestone and other such raw material. A raw material hopper 241 is located above input shaft 239 and the associated crushing shaft. Furthermore, sets of bearing assemblies 243 are associated for journaling input shaft 239 as well as other associated transmission shafts therein. A substantially axially oriented accelerometer sensor 245A and a substantially vertically oriented accelerometer sensor 245V perform vibration sensing at crusher input shaft 239 and the adjacent components such as bearings and gears. Additionally, substantially horizontally oriented accelerometer sensors 247 and 249 are attached adjacent the driving end and non-driving end, respectively, for sensing rotational vibration associated with electric motor 233 and the associated transmission component and bearings rotated therewith.

Figure 14:
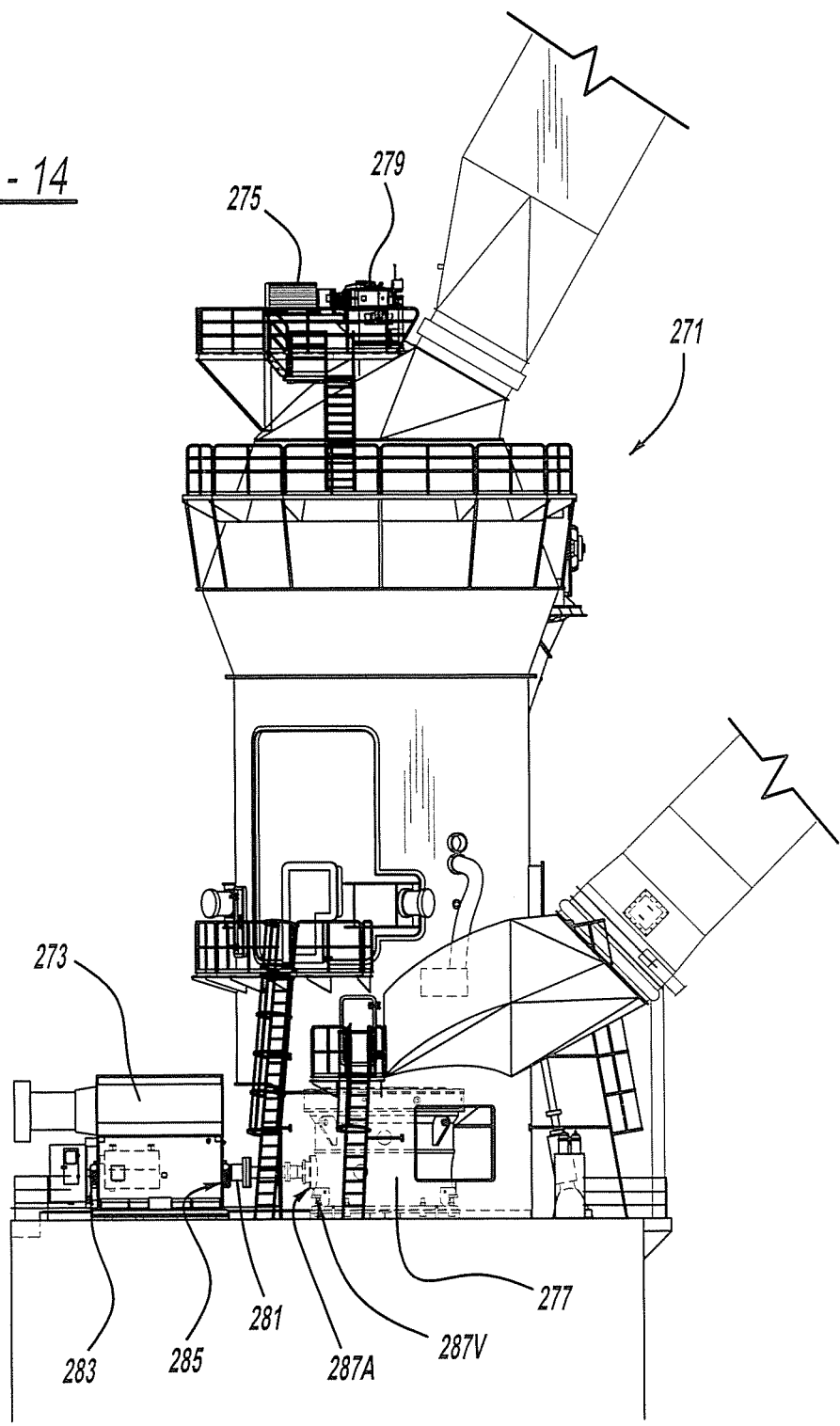
FIG. 14 is a side elevational view of a vertical roller mill machine employed in the system.
Figure 15:
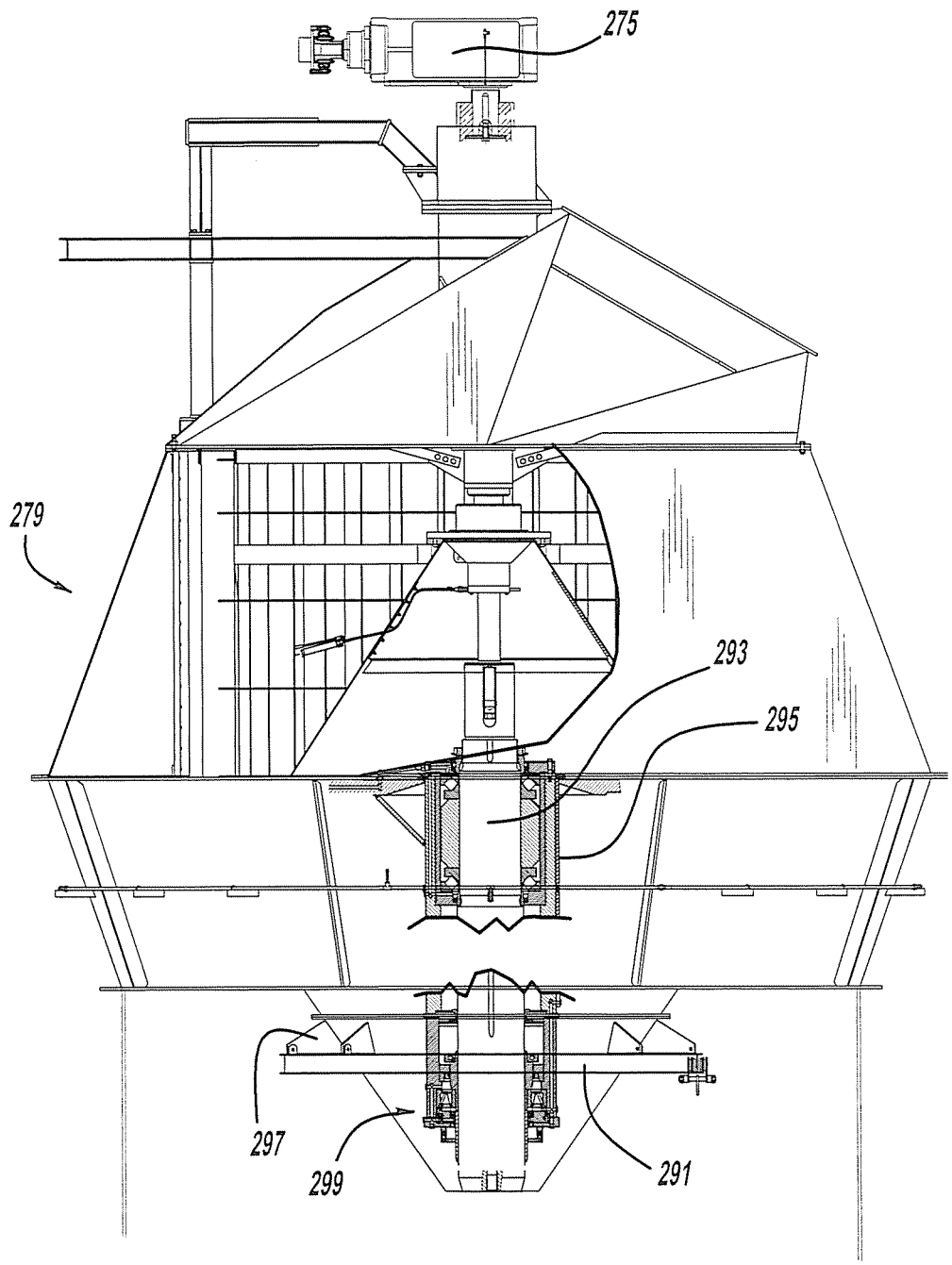
FIG. 15 is a partially fragmented top elevational view showing the separator machine employed in the system.

One out of eight similar milling machines 271 is shown in FIG. 14. Two of the milling machines reduce the size of the raw material before the kiln, four of the milling machines reduce the size of the clinker after the kiln and two of the milling machines are employed for the core fuel. A pair of electric motors 273 and 275 drive their respective gear boxes 277 and 279 via rotating shaft 281, gears and couplings. These transmission components operably rotate rollers or the like to reduce material size. A substantially horizontally oriented accelerometer sensor 283 is positioned adjacent the non-driving end of motor 273 while a substantially horizontally oriented accelerometer sensor 285 is positioned adjacent the driving end of motor 273 for vibration sensing associated with the motor and driven transmission components. Furthermore, substantially axially oriented and vertically oriented accelerometer sensors 287A and 287V are located adjacent an input shaft of gear box 277 for sensing the rotational vibration characteristics associated with the shafts, bearings and gears in gear box 277. Similar sensors are employed for motor 275 and gear box 279 as is shown in greater detail in FIG. 15.

Electric motor 275 drives the transmission components within gear box 279, which in turn, rotate a separator machine 291. An output shaft 293 and coupling 295 more particularly couple the transmission to a fan or cage 297 of separator machine 291. Multiple sets of bearings are also disposed within the separator machine, gear box and motor. A non-contact, proximity sensor 299 is mounted to separator machine 291 adjacent input shaft 293 and its associated bearings. Sensor 299 measures the relative displacement and provides an output DC signal. Sensor 299 further measures dynamic vibration by providing an output AC signal, which generates a spectrum for later analysis by the central processing unit and software. The use of a proximity sensor for the vertical separator shaft measures the relative clearance measurement in a non-contact manner and is advantageous for slower speeds such as with the separator shaft. Additional accelerometer-type vibration sensors may be optionally provided in the gear box and motor.

Figure 16:
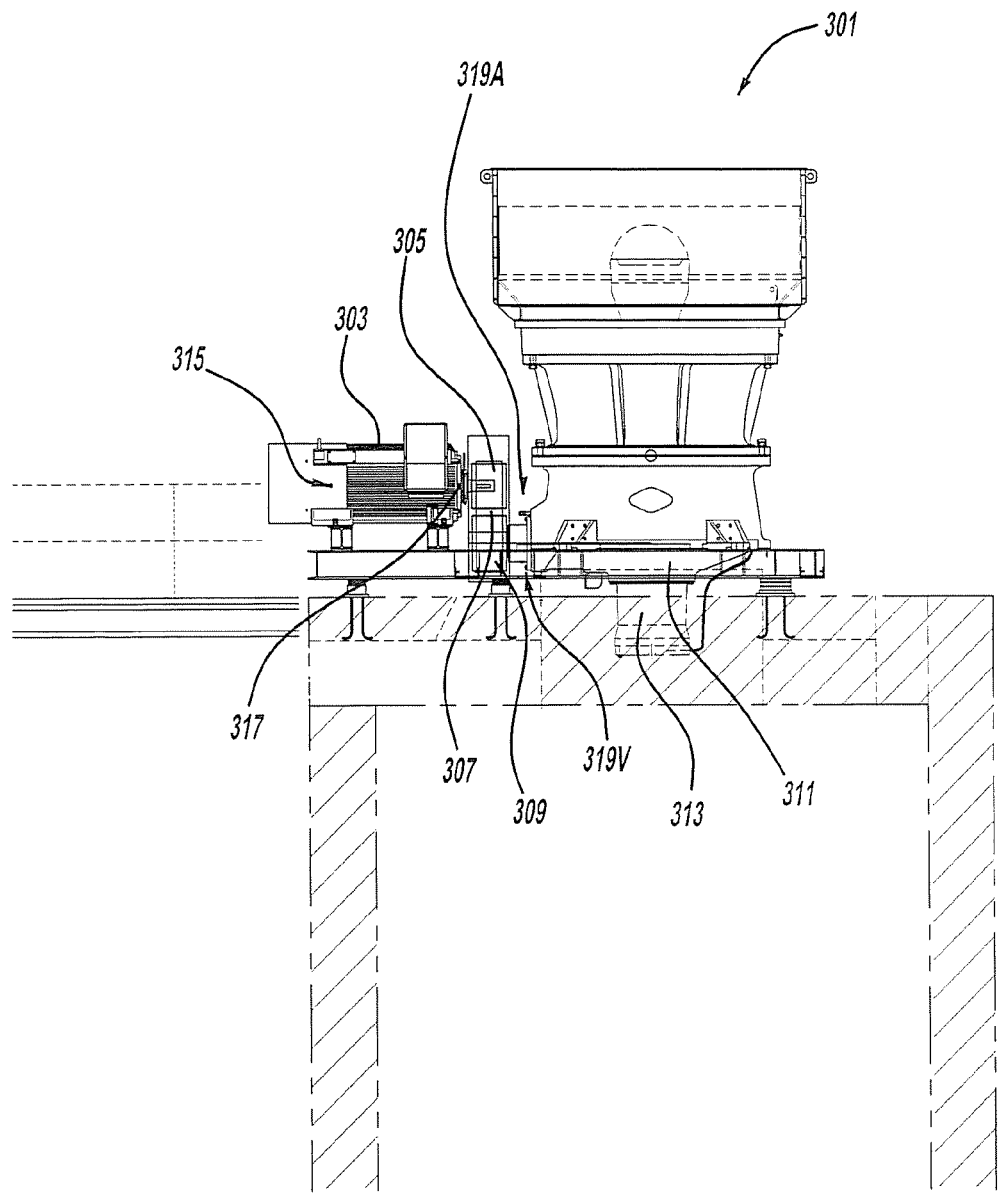
FIG. 16 is a side elevational view showing the crusher machine employed in the preferred system.

Referring to FIG. 16, a secondary crusher machine 301 is provided between the primary crusher and the kiln. Secondary crusher machine 301 includes an electric motor 303, an output pulley 305, a belts 307, an input pulley 309 and an input shaft 311. Input shaft 311 is rotated in response to energization of a raw material crushing shaft 313 or the like. A substantially horizontal accelerometer vibrational sensor 315 is mounted adjacent to a non-driving end of motor 303 and a substantially horizontally oriented accelerometer vibrational sensor 317 is mounted adjacent a driving end of motor 303. Furthermore, a substantially axially oriented accelerometer vibrational sensor 319A is disposed adjacent to input shaft 311 and its substantially vertically oriented accelerometer vibrational sensor 319V is located adjacent input shaft 311. The sensors measure vibrations associated with movement of associated shafts, gears and bearings.

Figure 17:
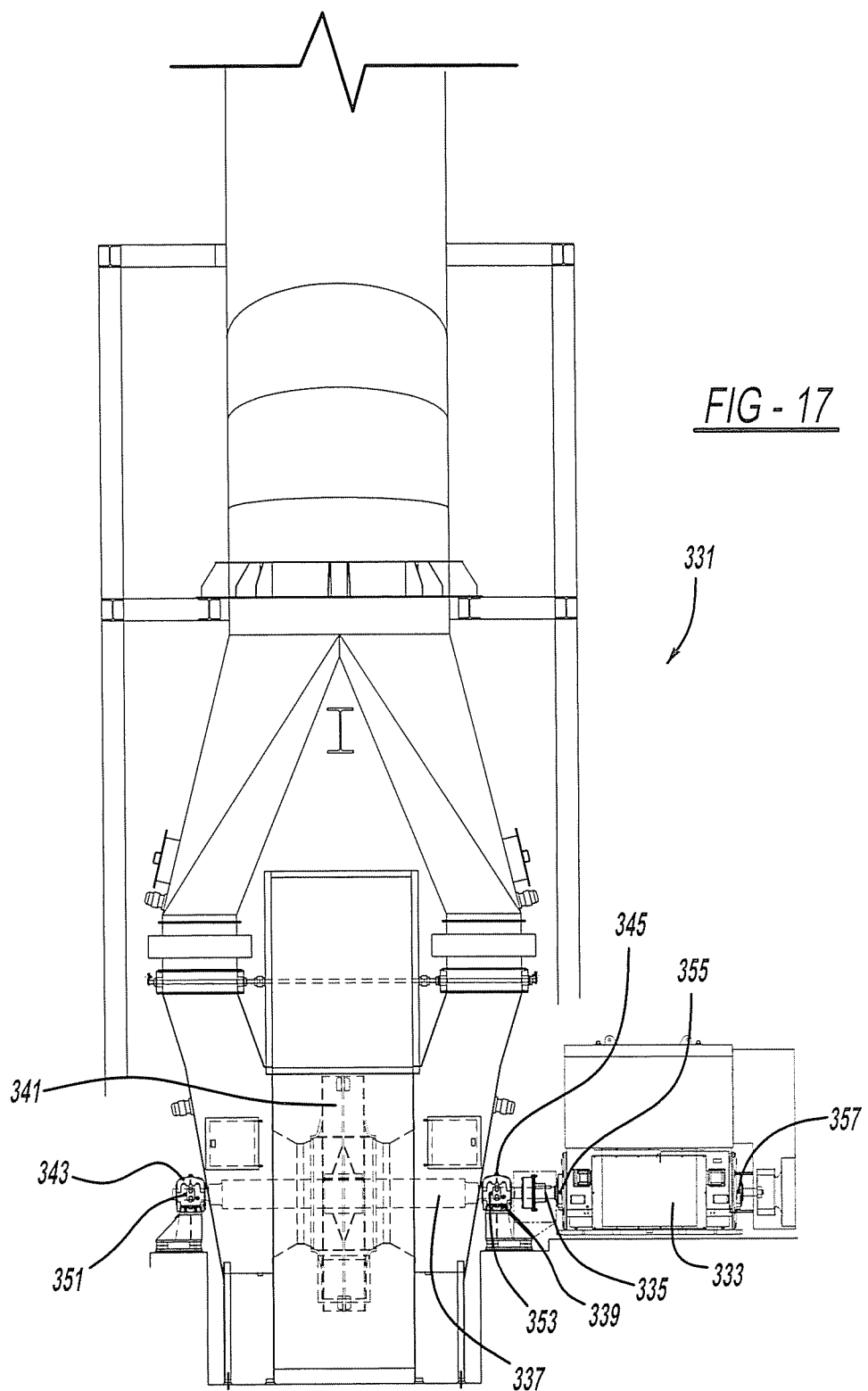
FIG. 17 is a side elevational view showing a fan machine employed in the system.

FIG. 17 shows a fan machine 331 which is employed in many different locations throughout the cement manufacturing plant. Approximately 15 or more fans are monitored in a real-time and continuous manner as further discussed hereinafter. An electric motor 333 operably rotates an output shaft 335 which is coupled to an input shaft 337 by a transmission coupling 339. A set of fan blades 341 are operably rotated with input shaft 337. A pair of pillow blocks 343 and 345, each having sets of bearing assemblies therein, support input shaft 337. A substantially horizontally oriented vibrational accelerometer sensor 351 is provided at the outboard bearing location for pillow block 343 and a substantially horizontally oriented vibrational accelerometer sensor is provided for the inboard fan bearing at pillow block 353. A substantially horizontal vibrational accelerometer sensor 355 is located adjacent a drive end of motor 333 and a substantially horizontally oriented vibrational accelerometer sensor 357 is mounted adjacent a non-drive end of motor 333.

Referring now to FIGS. 1-4 and 19, analog vibration signals are collected by accelerometer sensor 95 permanently mounted on rotating components within the equipment 93 being monitored. These analog signals are converted into digital form in data acquisition devices 91 and then transmitted to a server 65 acting as a central processing unit or computer controller. This analog-to-digital conversion occurs in the data acquisition boards which communicate with the network by either ether net protocols and network switches, or wireless protocols and access points 59. Server 65 houses essentially all of the data processing and analysis algorithms and software, manages data flow from all acquisition boards and performs a set of parallel tasks for data analysis. The server then directs the results to the display terminals 53, 57, 63 and a control room display monitor 401. Server 65 and its programmable software instructions monitor all of the measured sensor points and optionally, continuously analyze the data with a self-learning multi-layered, neural network algorithm that performs pattern recognition and identifies machine defects or potential maintenance concerns.

The software then posts or outputs the results and alerts for specific actions. The terminal computers 53 and 57 post a set of analysis features that receive live data from server 65 and perform octave analysis, power spectra, zoom FFT, FRF analysis, torsional analysis, order analysis, order tracking, tachometer processing, and Orbit, Bode, Waterfall, and Cascade plots. A fiber optic converter 403 is located within the same enclosure housing of each data acquisition device 91 and transmits the sensor output signal through optical fibers 405 to server 65.

Monitor 401 is located in the main, centralized control room for the entire manufacturing plant. Monitor 401 displays the sent information and any alarms in a simplistic fashion. This control room display may take the form of a virtual illustration of the entire manufacturing plant, or portions thereof, such as those displayed in FIGS. 20-22, with various colored lights or other illustrated warning indicia being visually seen if a problem or other undesired situation occurs at any sensor point.

Computer terminal 57 is for an operator, who is a data analyst or maintenance supervisor, to review the detailed data calculations, trends and other output from the monitoring software. This computer terminal 57 is in a centralized and remote location spaced away from the equipment being monitored and has the capability to analyze and manipulate the real-time and continuously monitored sensor information as well as information from off-line databases. Computer terminal 53 is also remotely located away from the monitored machines and is used by computer personnel to make programming changes to the software instructions employed in server 65, if necessary. A TIS web host 407 is connected to the network via ethernet, and provides executive and routine maintenance reports for the entire manufacturing plant operations. Moreover, PDA devices 63 are connected to the network for receiving warning alarms and other information of undesirable situations occurring through e-mail communications and the like, thereby notifying plant engineers and technicians who may not be present at the control room or analyst computer terminals.

The present system currently monitors approximately 800 of the cement manufacturing equipment in an off-line manner, where a handheld unit is employed to collect data from running equipment and download the collected data in an off-line database for manual analysis. However, in the presently preferred embodiment, about 80 equipment are monitored on a real-time and continuous basis due to the manufacturing importance or cost of the associated equipment. Furthermore and optionally, the continuously monitored equipment signals can be routed to the hand held unit through the data interface devices 411 (see FIG. 19) as an alternative remove collection method for the off-line database.

The software allows for adaptive monitoring of the equipment through the sensors, for the on-line and continuously monitored equipment. Based on the severity of the potential problem and the criticality of the specific equipment, the software can selectively take snap shots of data and trend information, the frequency of which can be automatically increased if a problem is detected. This allows for more aggressive monitoring if the software automatically determines that alarm or fault levels of a monitored location are increasing. The software is intelligent and self-adjusting where it automatically adjusts its fault detection criteria based on the equipment running conditions. For example, equipment running speeds are continuously changed and optimized for the manufacturing process by the control room operators.

Furthermore, a switch matrix and a multiplexer are employed to most optimally connect the sensors to the server while providing at least 50 channel data acquisition and more preferably, 64 channel data acquisition, but at a significantly reduced hardware cost compared to if multiplexing was not employed. Optionally, the software can further perform generally real-time, evolutionary learning calculations based at least in part on signals from the sensors to determine if operating problems occur, identify the actual mechanical problem based on the data, and report the results based on historical data on associated maintenance. This allows the software to automatically identify the actual problem occurring based on various characteristics of the qualitative analog sensor signals while also accounting for prior maintenance trends, and field observations relative to prior sensor signal data.

Figure 19:
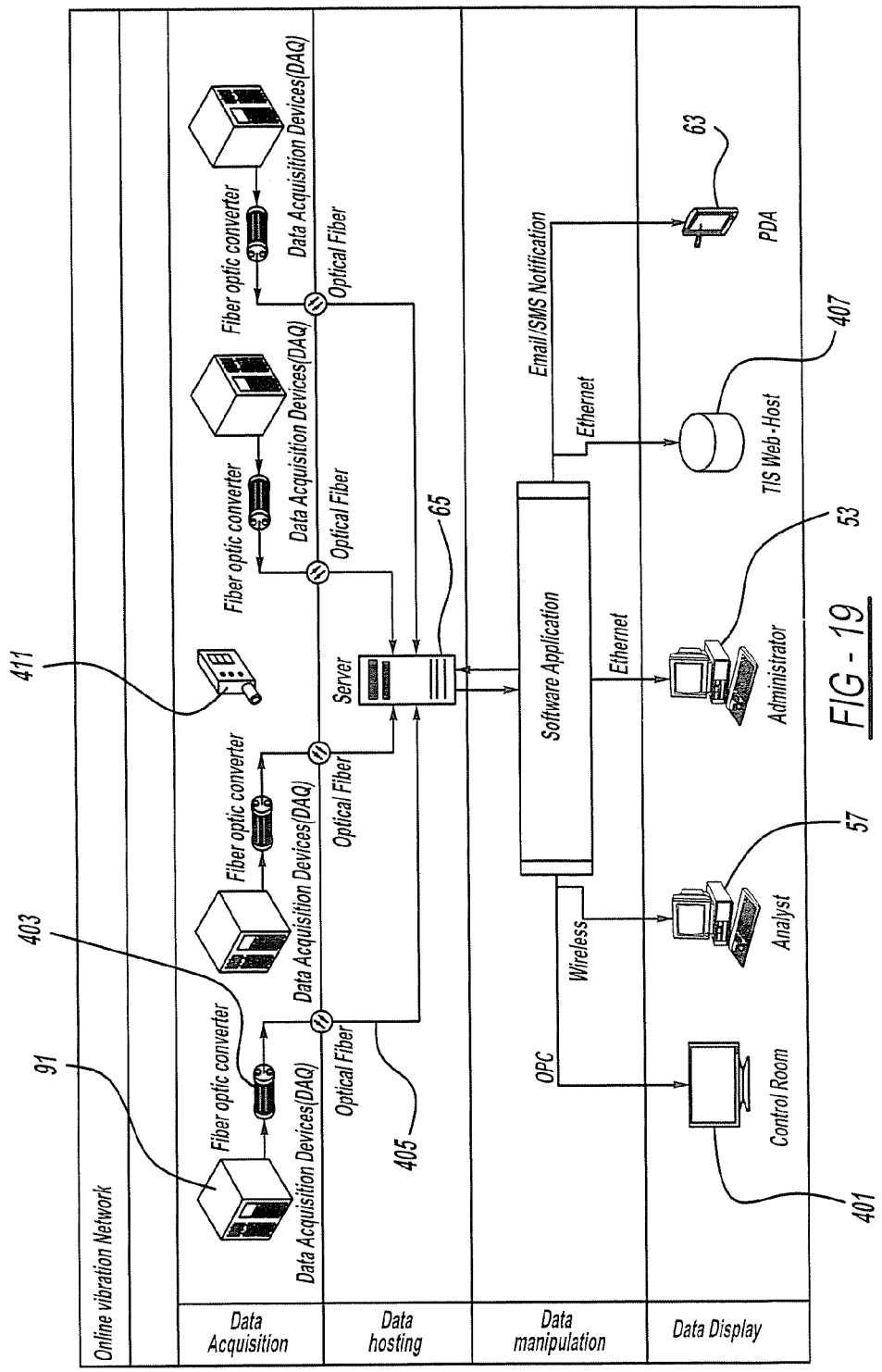
FIG. 19 is a diagrammatic view showing a computer network layout employed in the system.
Figure 20:
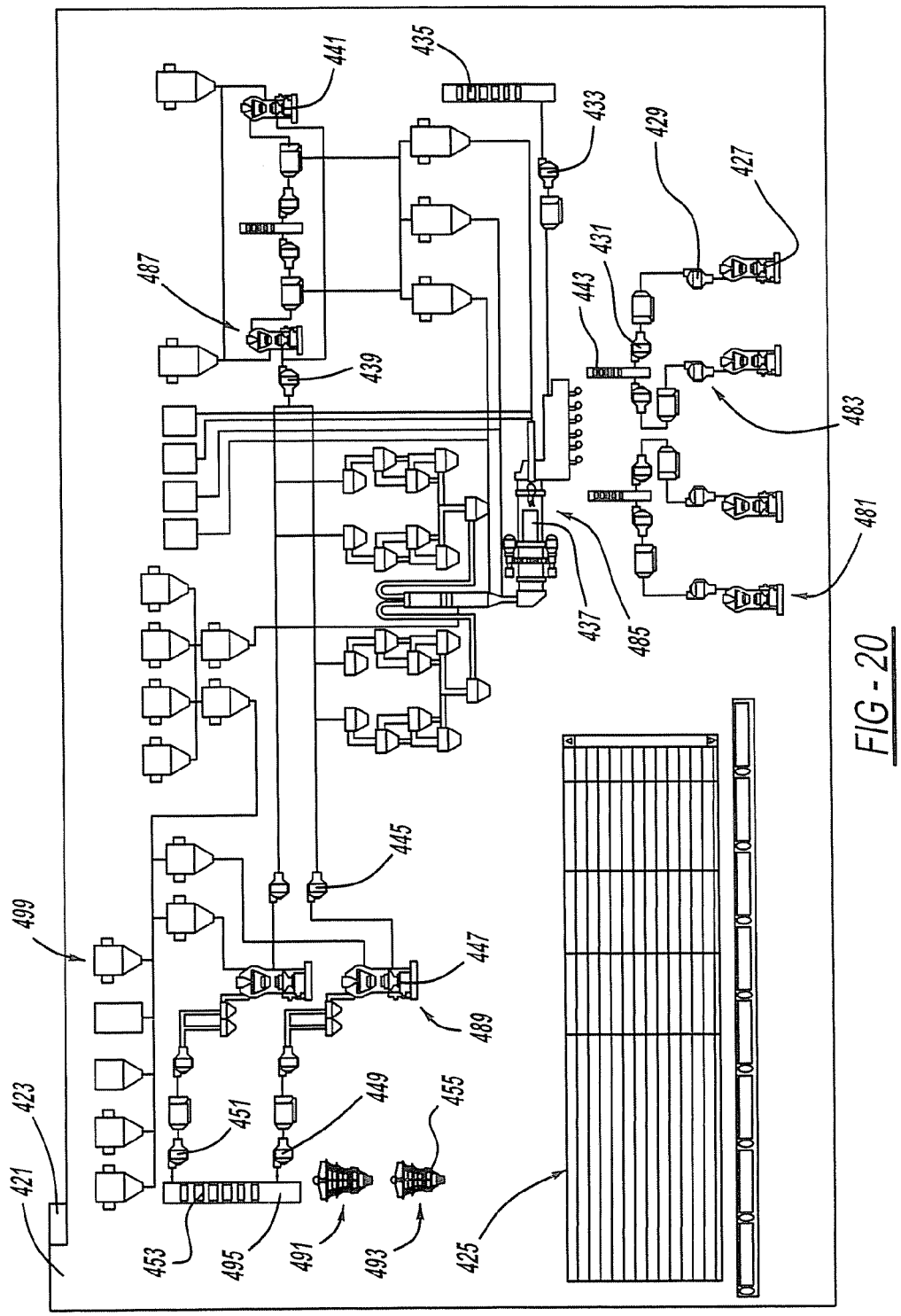
FIG. 20 is a diagrammatic view showing a computer screen display for a main interface employed in the system.

FIGS. 20 through 23 show various software application interface displays for the monitor of analyst computer terminal 57 (see FIG. 19). FIG. 20 shows the main interface of the software for alarm and notification. In particular, this is the display associated with a "plant overview" tab 421 (versus a hidden "control" tab 423). An alarm list 425 is displayed in a chart at the bottom of the screen display. This main interface visually shows a simulated representation of the manufacturing plant machinery with various sensor indication boxes 427, 429, 431, 433, 435, 437, 439, 441, 443, 445, 447, 449, 451, 453, and 455. These indication boxes are associated with the real-time, continuously monitored sensors and are shown in red if there is a problem, green if a sensed data is satisfactory and a blinking yellow if maintenance is recommended but not yet a problem. This screen display shows virtual finish mills 481, fans 483, kilns 485, coal-fuel mills 487, rolling mills 489, primary crusher 491, secondary crusher 493, smokestacks 495 (which are monitored in a non-continuous, off-line manner) and various storage bins 499 which are not monitored. The term "crusher" may be generally used throughout this disclosure to include mills, crushers and grinders.

Figure 21:
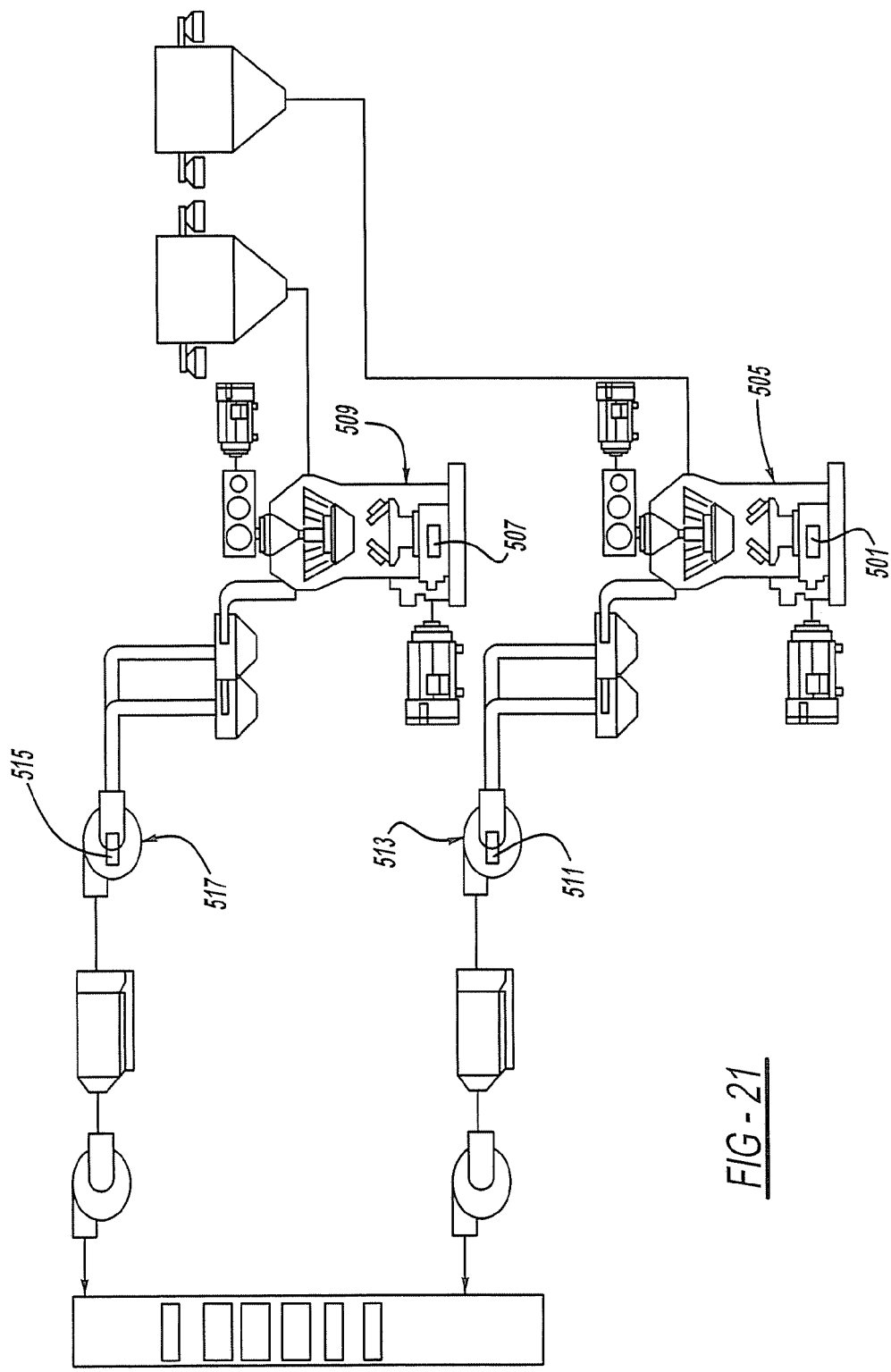
FIGS. 21 and 22 are diagrammatic views showing computer screen displays for data transfer sections of the interface in the system.

FIG. 21 illustrates a route acquisition interface where the associated "controls" tab is shown and the "plant overview" tab is hidden. This screen display also provides virtual illustrations of equipment throughout the manufacturing plant depending on which section of the plant is selected for display. An indication box 501 for a first roll mill 505, an indication box 507 for a second roll mill 509, an indication box 511 for a first fan 513, and an indication box 515 for a second fan 517 can be shown in red, green or yellow. The indication boxes are green if the sensored data has not yet been transferred to the data interface devices 411 (see FIG. 19) within a predetermined period of time. A red box designation indicates that the sensored data has already been acquired within the predetermined time period and a linking yellow colored box indicates that the signal is being acquired. The predetermined time can be set for once per week, once per day or in a manual manner by the analyst. It should be appreciated that alternate color designations or graphic designs for any of the interfaces can be employed.

Figure 22:
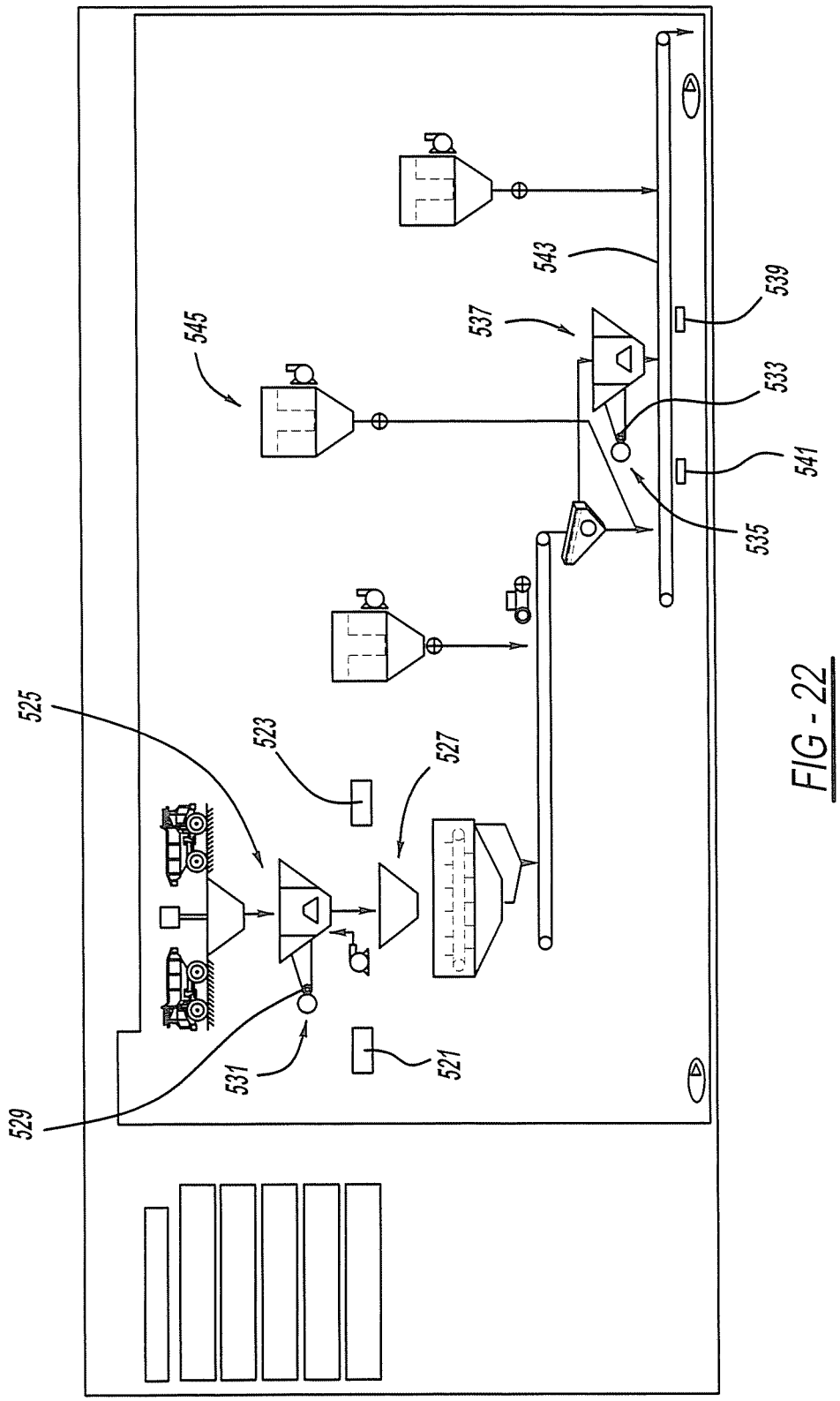

FIG. 22 illustrates a virtual plant equipment layout for a different area of the manufacturing plant. This display shows signal acquisition color indication boxes like that for the prior figure. In this plant area, indication boxes 521 and 523 are associated with sensors for crushing machines 525 and 527. Color display circle 529 is associated with the sensors for electric motor 531. Furthermore, an indication circle 533 is for electric motor 535 associated with crusher machine 537 while indication boxes 539 and 541 are associated with sensors for different portions of crushing machine 537. Additional conveyors 543 and storage bins 545 are illustrated but not monitored in this exemplary embodiment.

FIG. 23 shows another application interface screen display for the present system. This computer screen display shows the "control" tab 423 view with the "power spectral peaks" sub-tab 571 activated. Alternately, "weighted data" tab 573, "octave spectrum" tab 575 or "RMS" ("route/mean/squared") level tab 577 can be activated to display different forms of the wave form data. A channel control category 579 can be selected by the analyst in order to select which real-time sensor data is to be displayed. The frequency range values can be entered at input area 581, the number of lines value can be entered at 583, the peak search settings, such as single or multiple peaks, can be input at 585, and the scaler or dynamic limits can be entered at 587. This interface shows a vibrational spectrum, or alternately wave form, from the selected sensor.

It is noteworthy that in one software module, the software employed in the present system automatically compares the sensed vibrational peak values to predefined values associated with the machine component properties. The software then automatically calculates differences and automatically determines if there is a problem, and the severity of the problem, for different frequencies. These predetermined values are essentially the nominal harmonic vibration characteristics for a rotating bearing, gear or shaft as determined from the supplier's specifications, a textbook or prior field use during optimal conditions. This desirable target data is stored in memory of the central processing unit for quick access by the microprocessor of the central processing unit. The present software allows for very quick and efficient real-time and continuous comparisons of the monitored sensor values as compared to the target values for all of the continuously monitored sensors. The software and central processing unit controller automatically provide historical trends, alarms for problems, less urgent maintenance or inspection notifications, and the, like for thousands of sensed values every second.

Figure 24A:
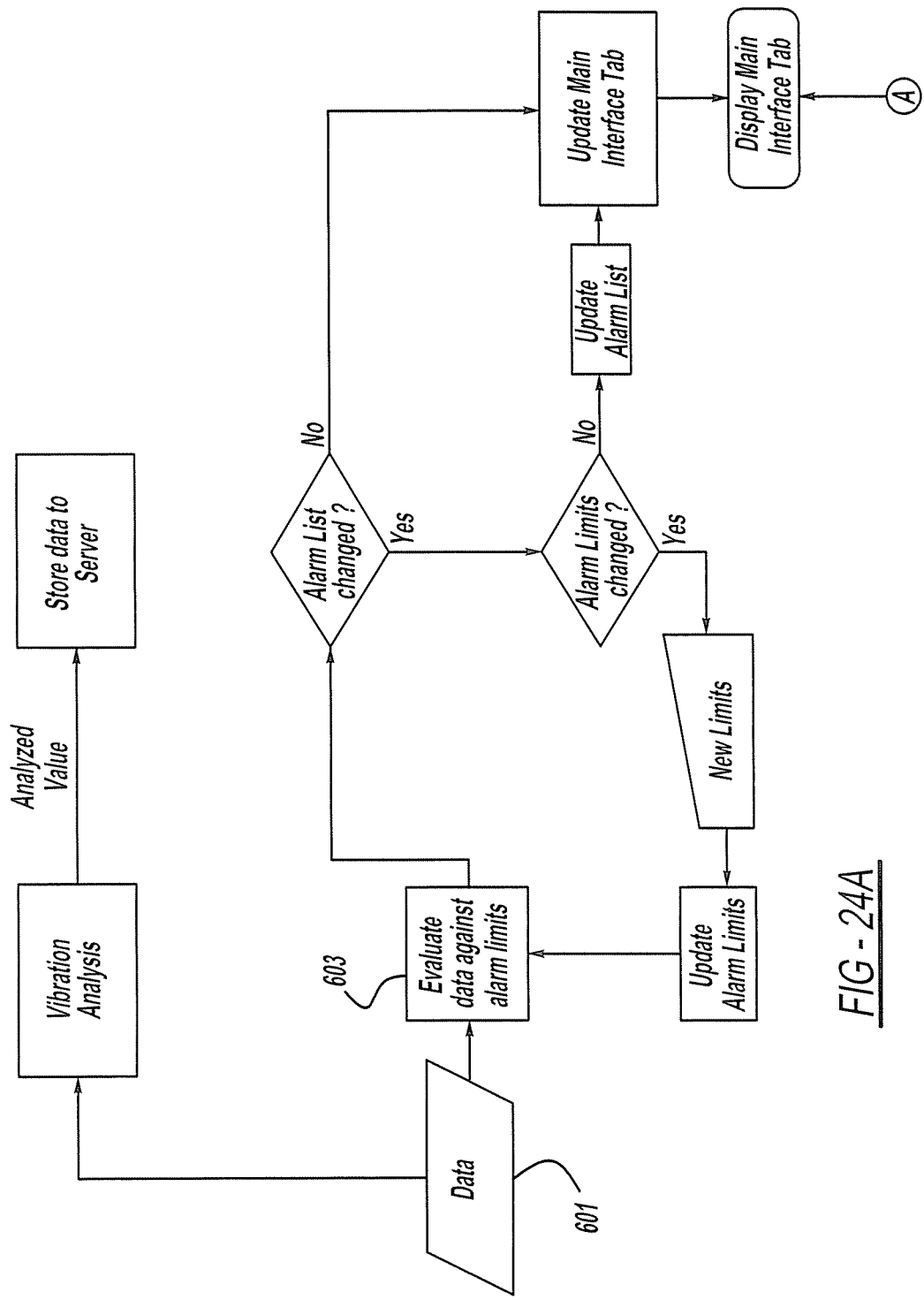
FIGS. 24-29 are flowcharts showing software logic employed in the system.
Figure 24B:
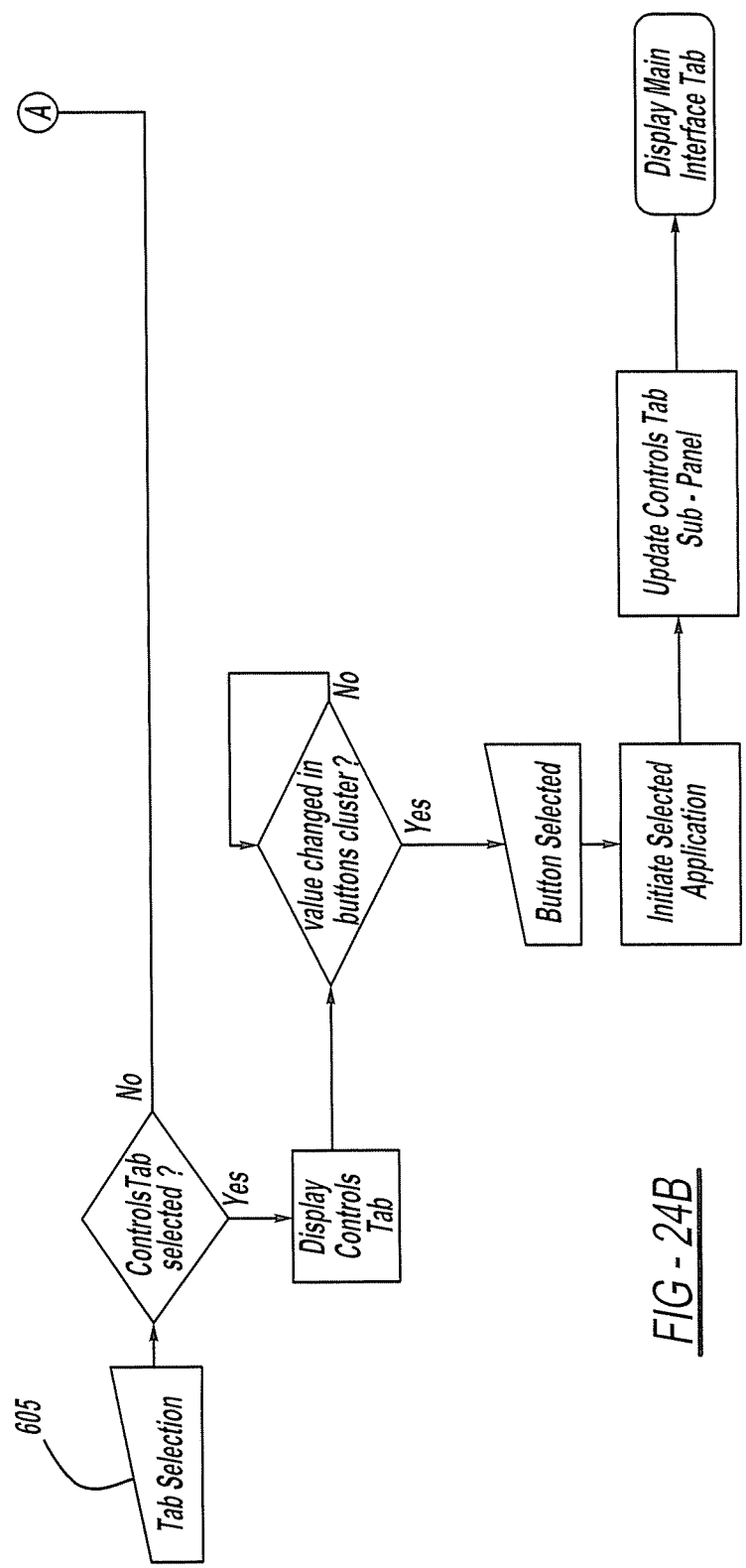

The programmed instructions for the computer software of the present system are stored in random access memory of the central processing unit, or alternately read-only memory, a removable disc, tape or other storage device. Referring to FIGS. 24A and 24B, software flow diagrams show a main interface software logic for the alarm and notification interface and for automatically determining if an e-mail or other error reporting message needs to be sent at box 611 (see FIG. 27) to a remote communications device 63 (see FIG. 1) carried by the plant engineer or technician. This corresponds to the interface screen display of FIG. 20. Trapezoidal boxes such as "tab selection" indicate analyst manual entries, diamond-shaped boxes such as "value changed in buttons cluster" indicate logical computer operations, rectangular boxes such as "vibration analysis" indicate computer processes, while generally ovallular-shaped boxes such as "display main interface tab" indicate final computer processes. If the alarm limit is exceeded, then the software updates the alarm list by displaying the newly determined problem. If it does change, then the update alarm limits the updated and reevaluated against newly sensed data values. If the list is not changed, then no update is needed. The software often updates the main interface, such as by providing a different color to the displayed indication boxes in FIG. 20, and it refreshes the main display. More specifically, the data box 601 indicates stored data on the CPU server that is sensed from the data acquisition devices, then evaluates data against the alarm limits calculation in comparison box 603 if performed in the CPU server, and the tab selection box 605 requires manual selection between the plant overview and controls tabs from FIG. 20.

Figure 25:
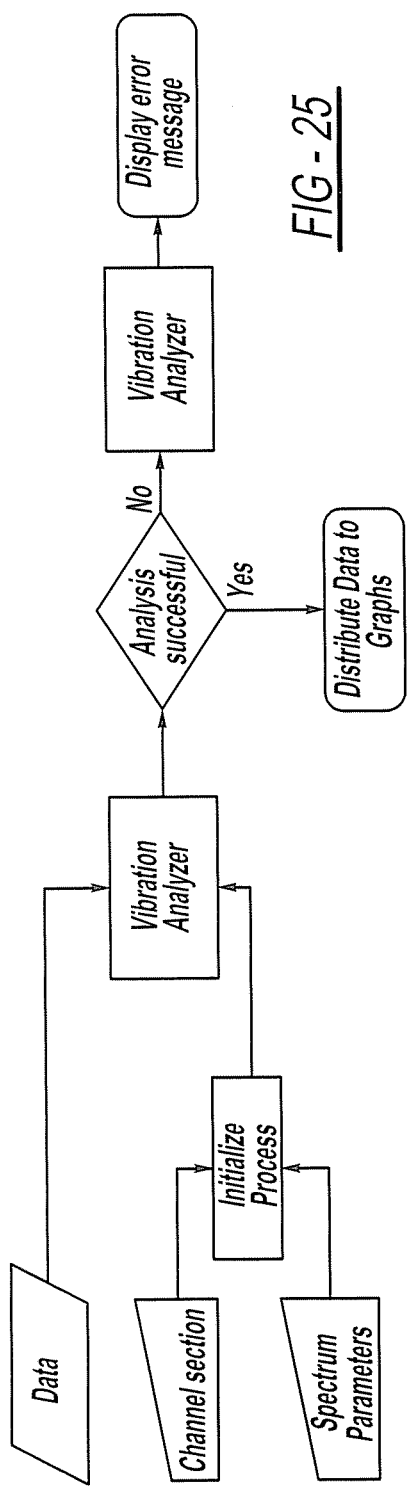
Figure 26:
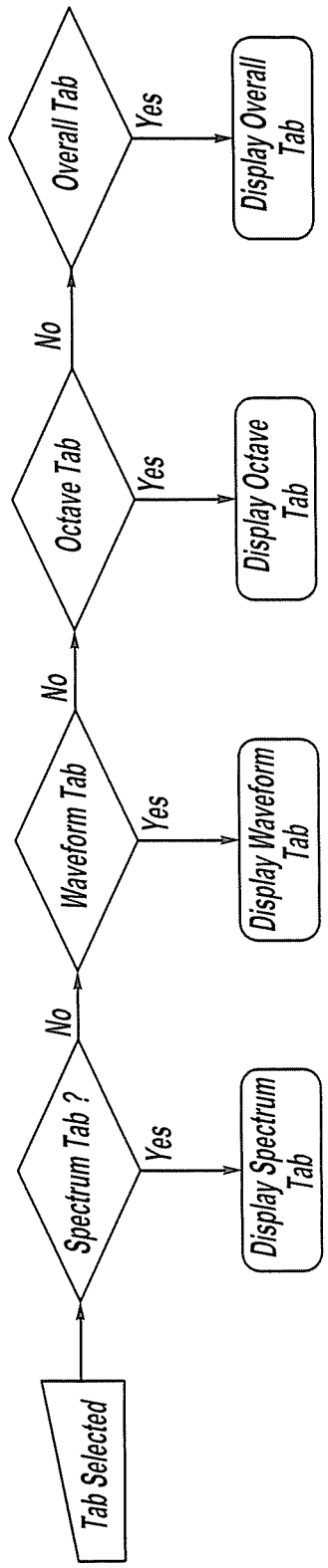
Figure 27:
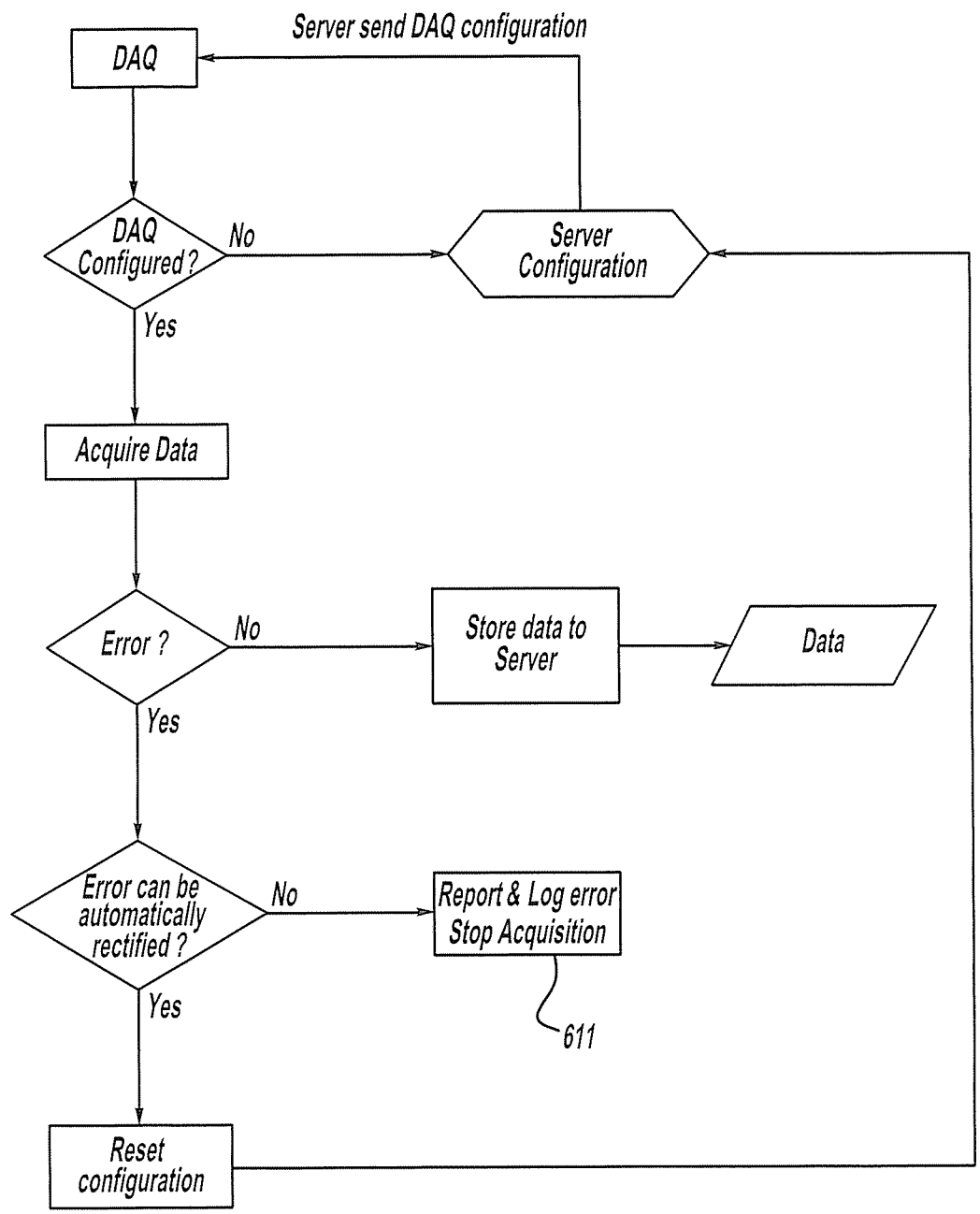

FIGS. 25 and 26 are software flowcharts that correspond to the screen display and analysis of FIG. 23. This software routine allows for the manual analysis operations module of the sensed data. As previously mentioned, the data can be automatically compared and analyzed, or it can be manually compared and analyzed by the operator, thereby providing different operations possibilities depending upon the equipment needs. FIG. 27 shows the software flowchart for the continuous acquisition process from data acquisition devices 91. This routine is automatically conducted by the software and controller for all of the real-time and continuously monitored sensors which are associated with the most critical or expensive machinery components.

Figure 28:
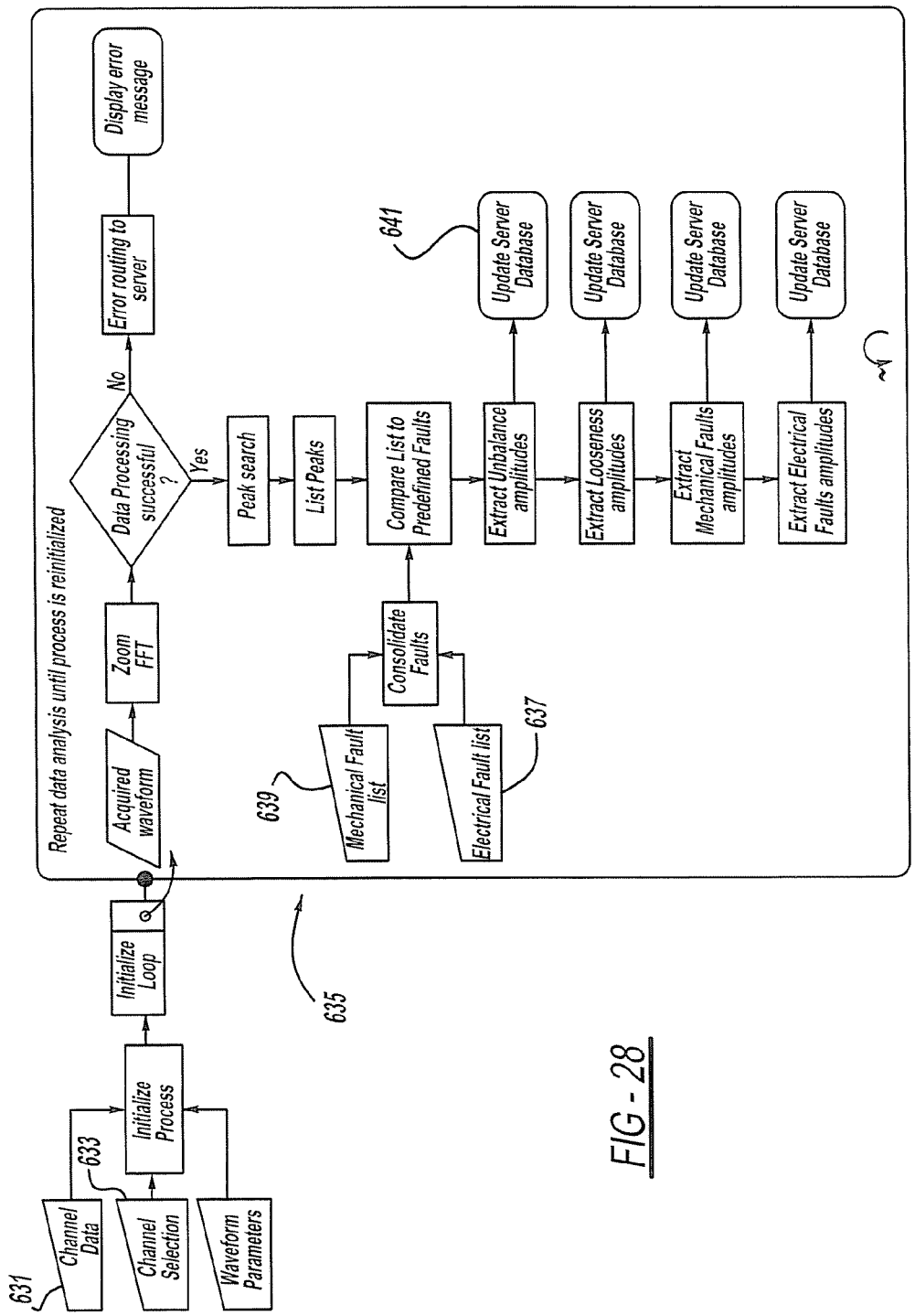

Referring now to FIG. 28, a vibration analyst application software flow diagram is shown. Incoming sensor data is received in box 631 and the physical/mechanical perimeter values for a specific machinery component are received in box 633. Fast Fourier transform procedures are used to match the physical/mechanical properties to the real-time sensor data and the software routine 635. Predefined rules with regard to comparing sent data to target values are indicated by boxes 637 and 639, while boxes indicated by 641 store and track historical trends for prior years for routine maintenance reports and to analyze long-term machine component vibrational trends. This software routine triggers alarm limits if unbalanced conditions, for example, are determined by the software and controller, and then alarm or fault severity levels are calculated, and subsequently, the appropriate visual, audio and/or written alarm indications are activated in an automatic manner. For example, a high alarm requires immediate attention and a high/high alarm requests the control room operator to manually turn off power to that specific machine in a severe situation.

Figure 29:
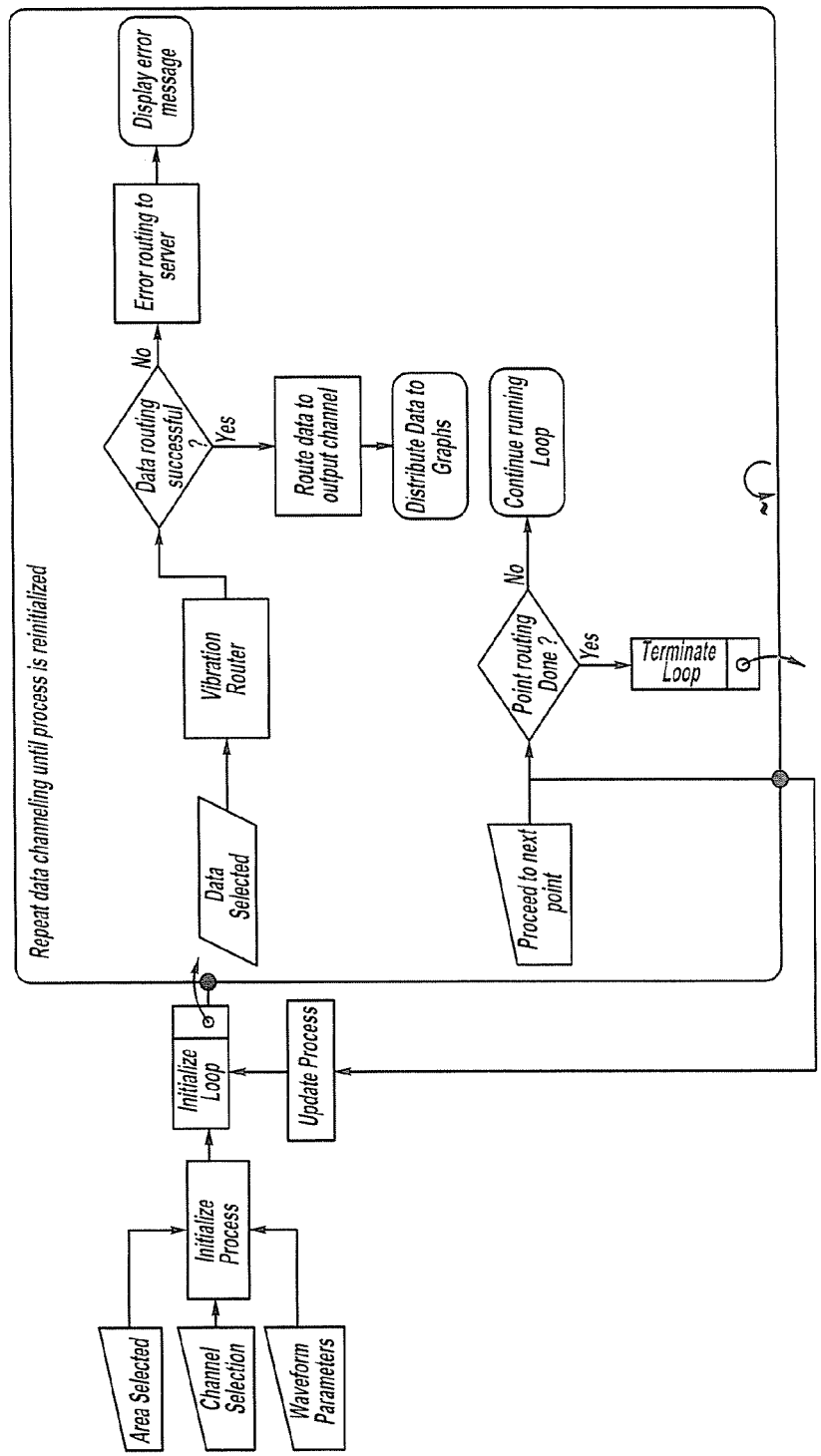
Figures 1, 30A:
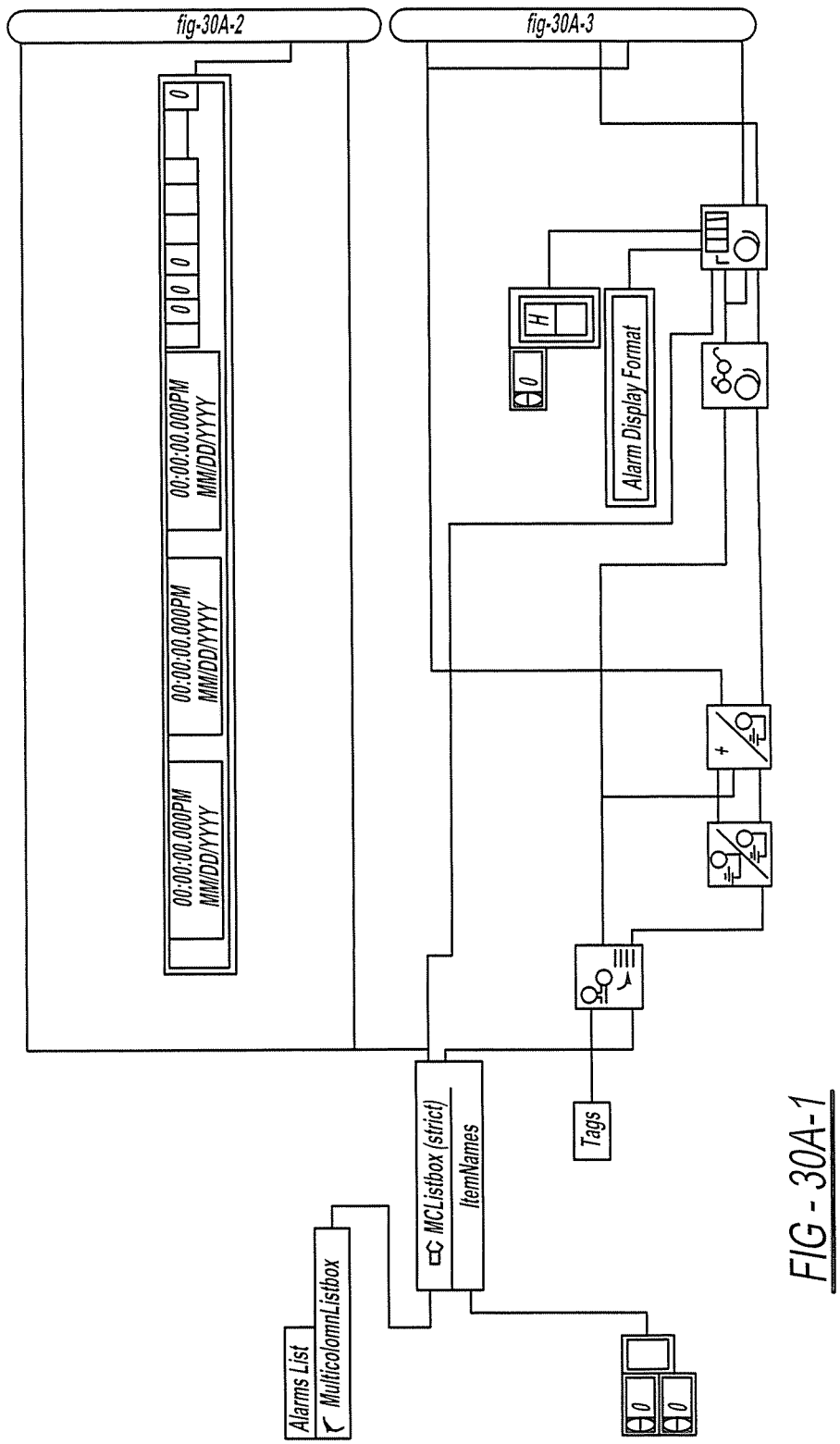
Figures 2, 30A:
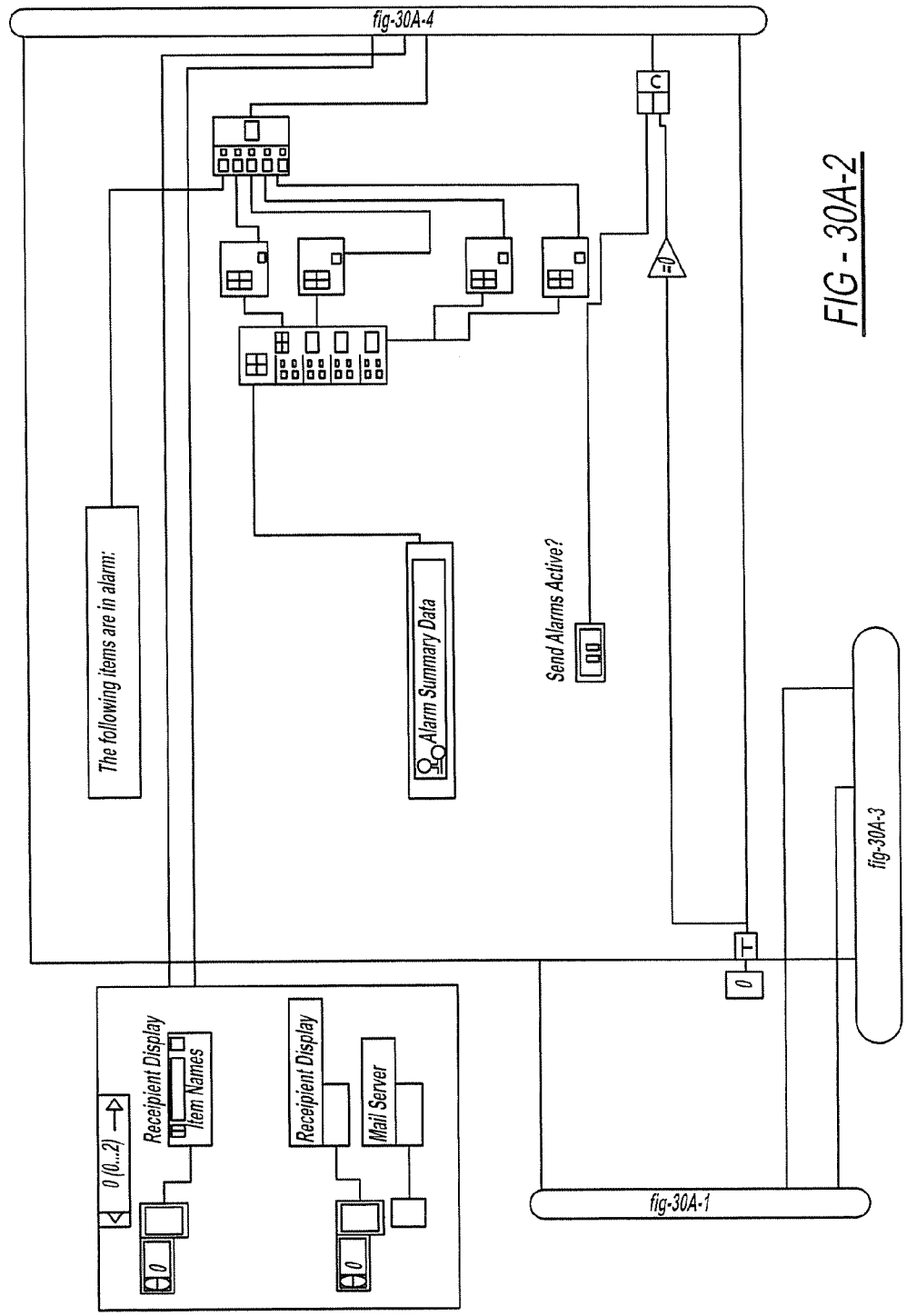
Figures 3, 30A:
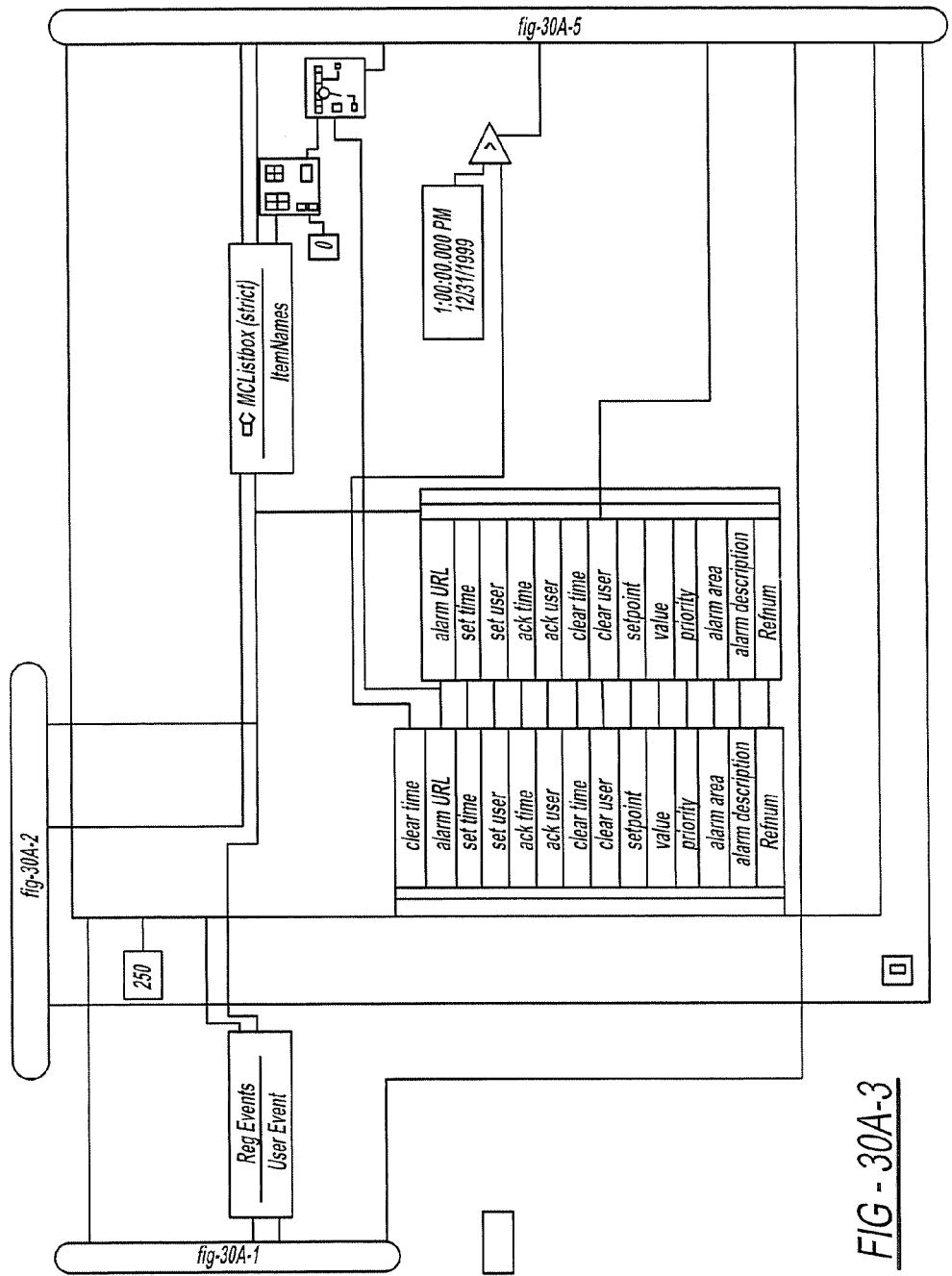
Figures 4, 30A:
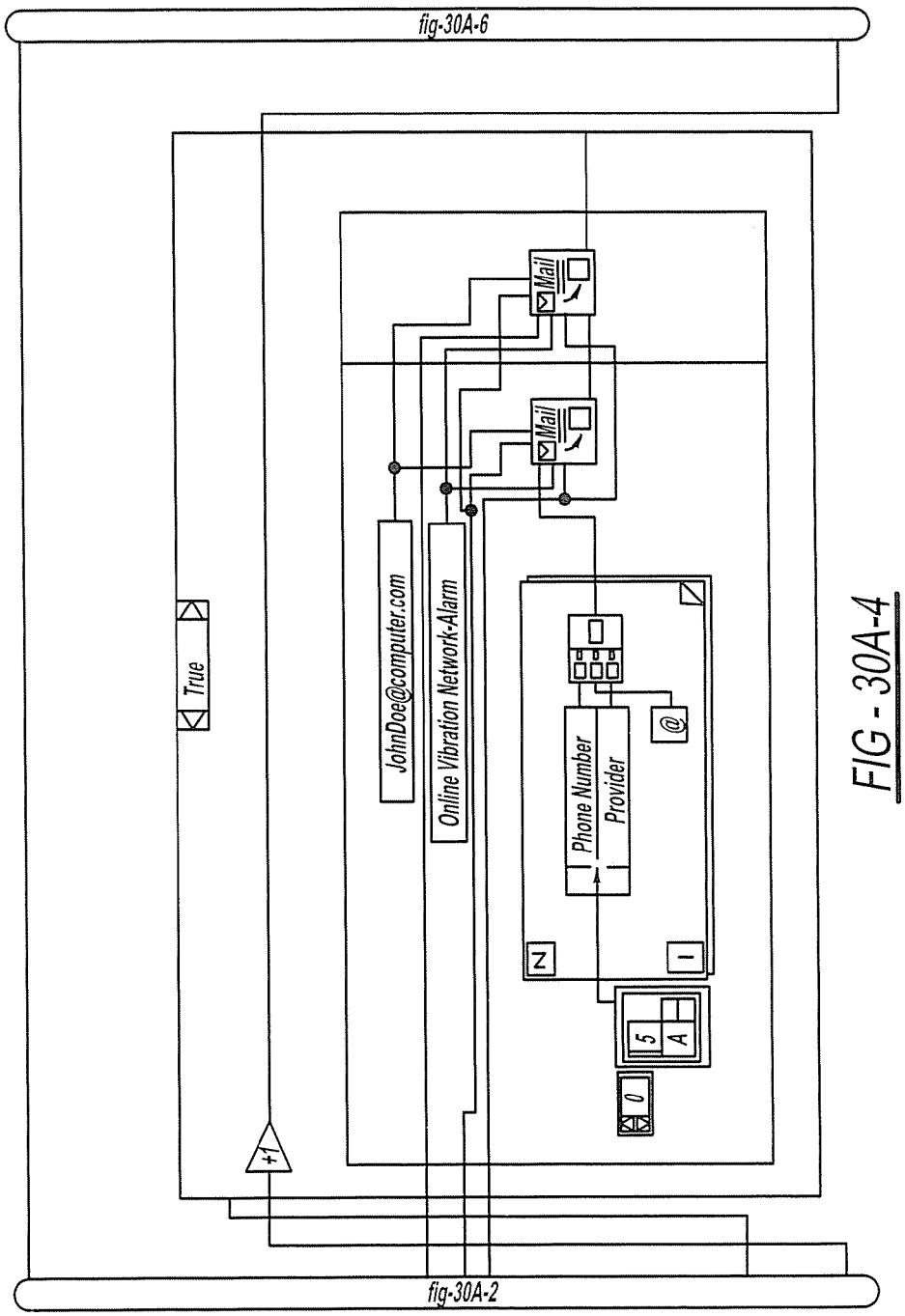
Figures 5, 30A:
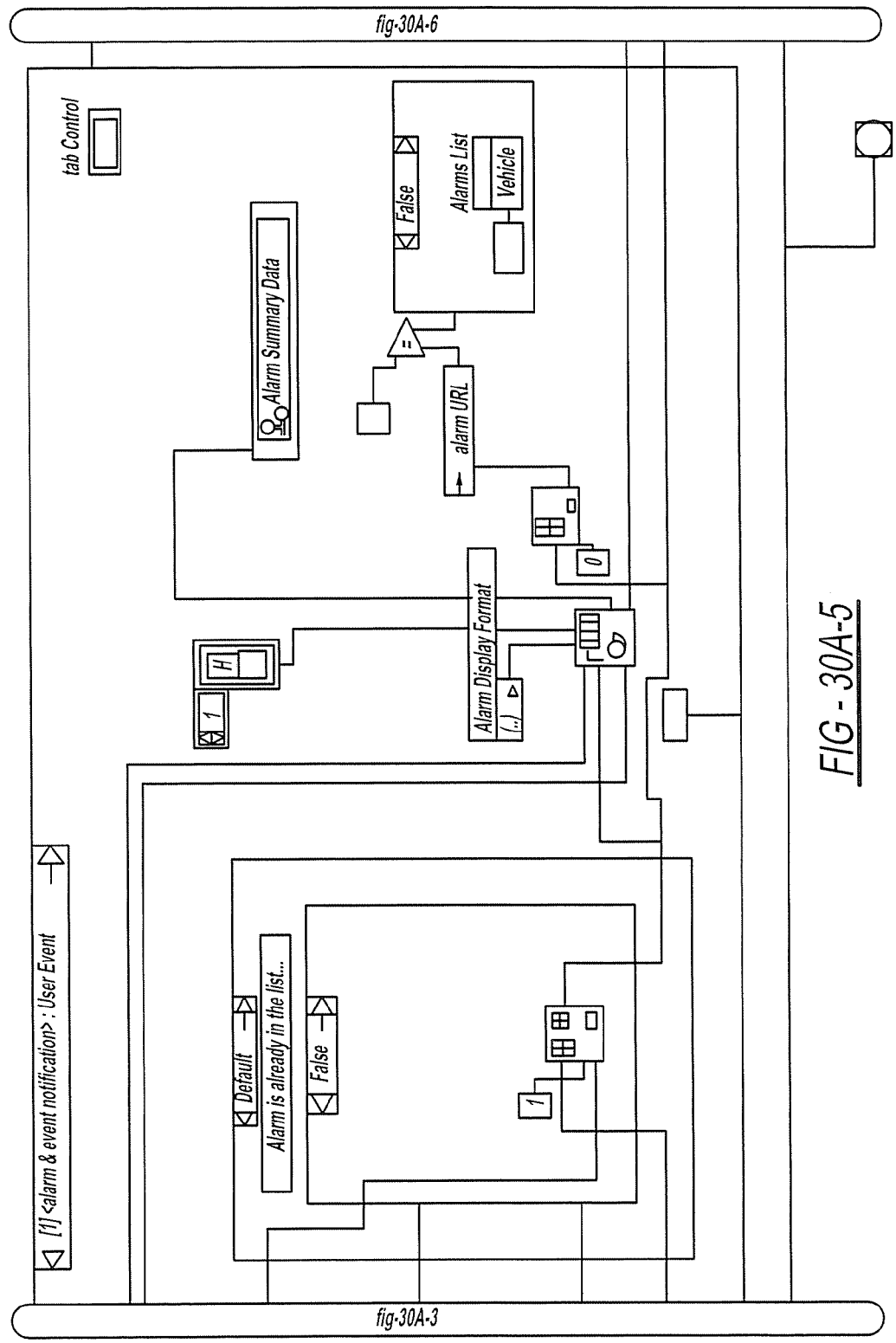
Figures 6, 30A:
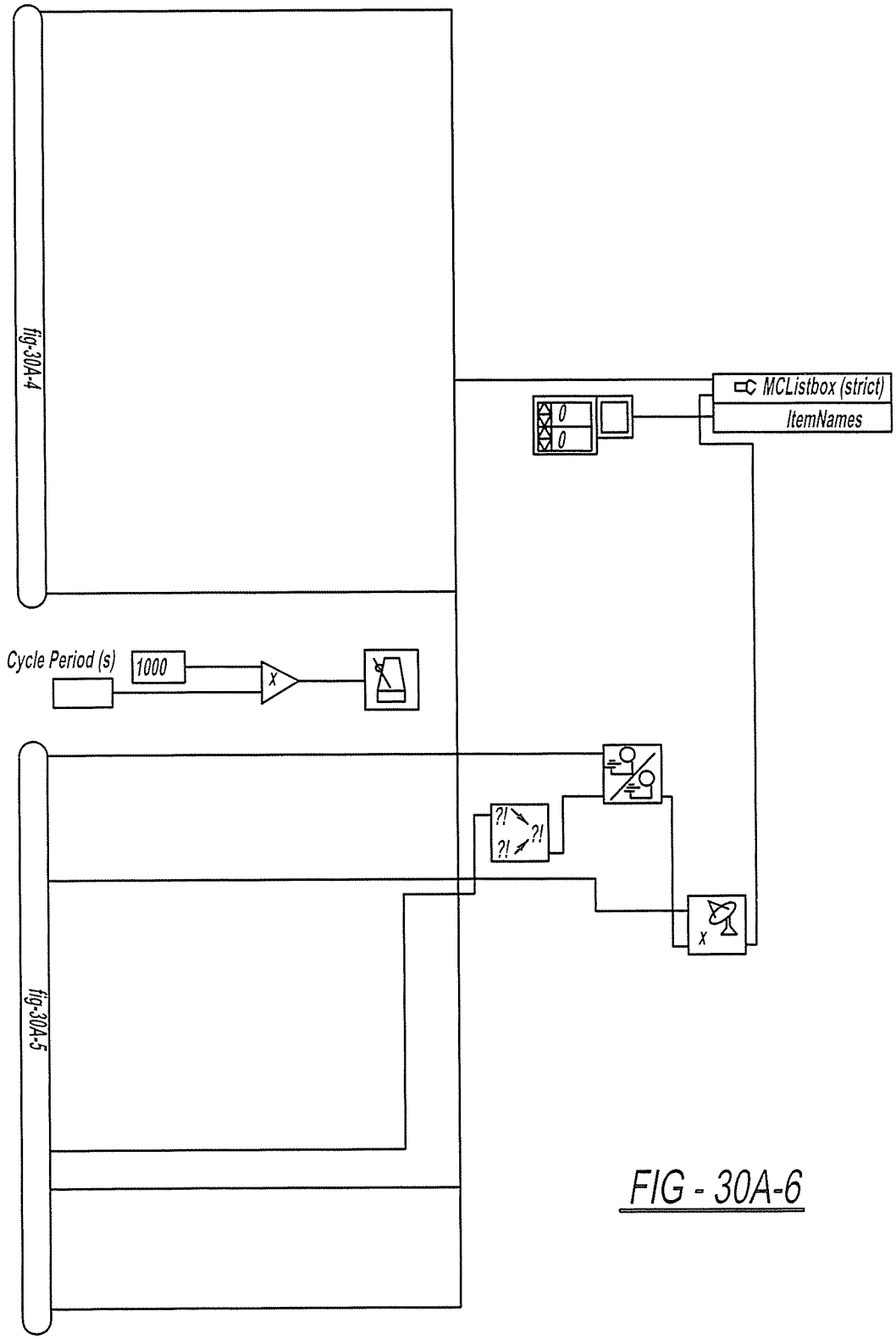
Figures 7, 30A:
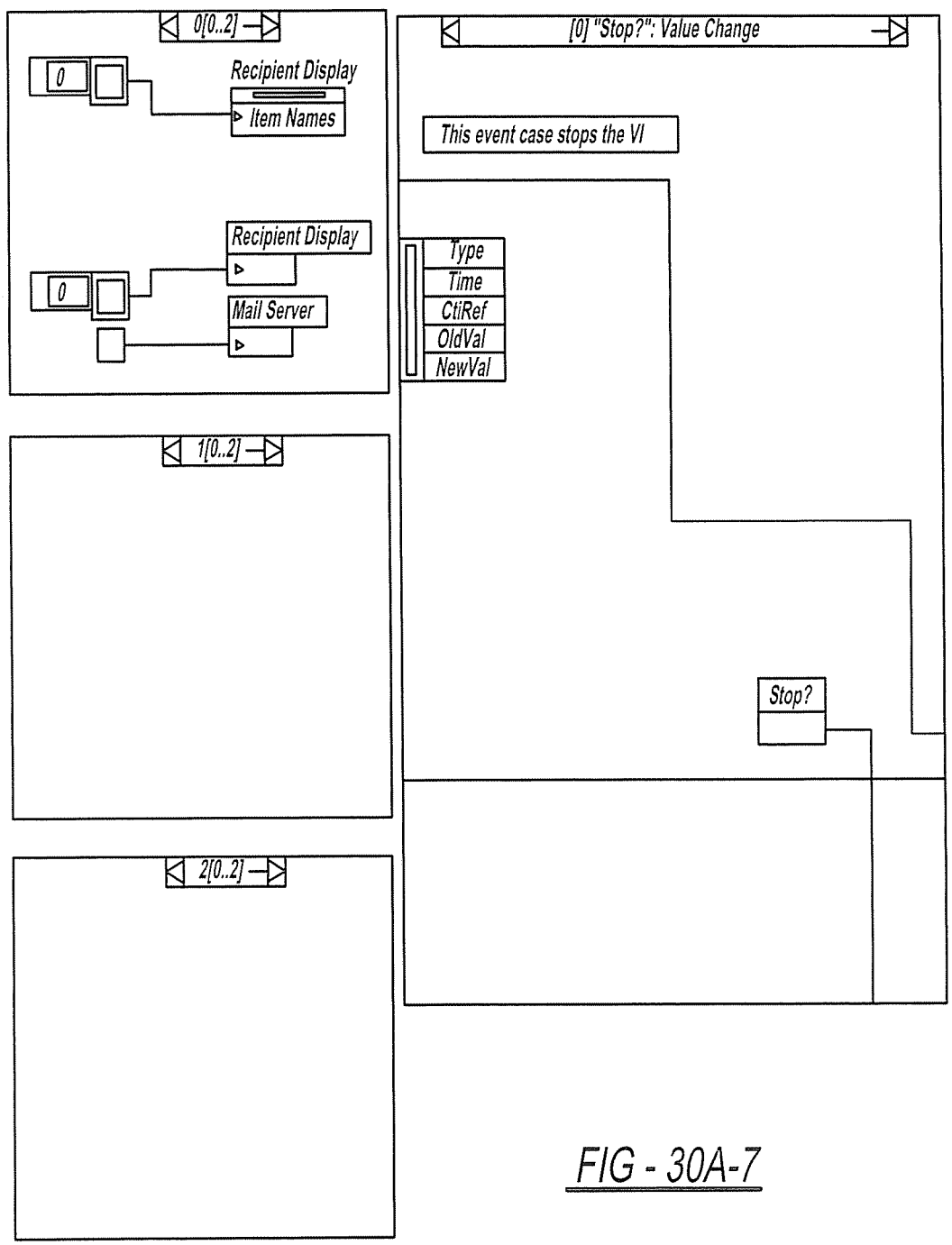
Figures 8, 30A:
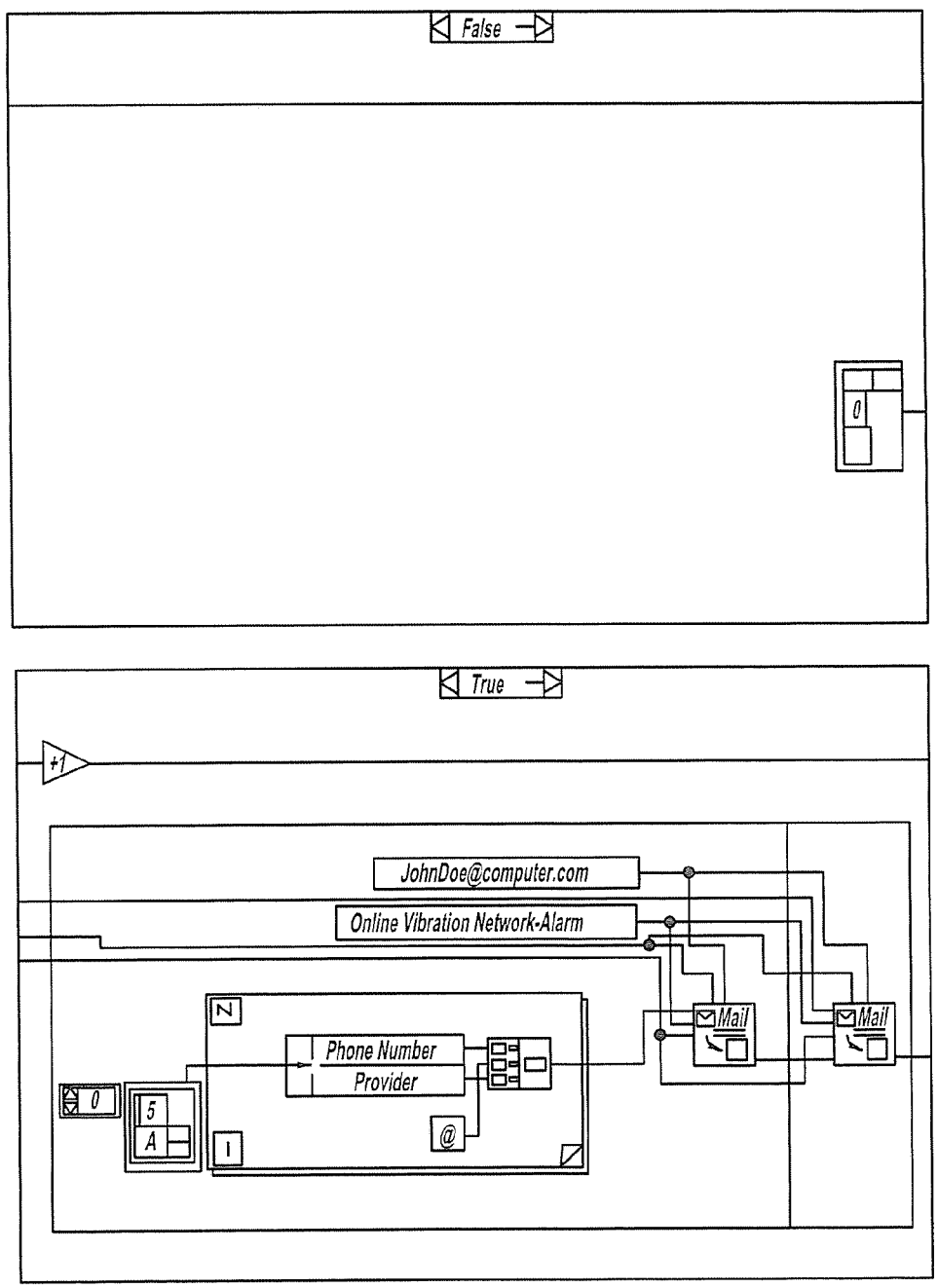
Figures 1, 30B:
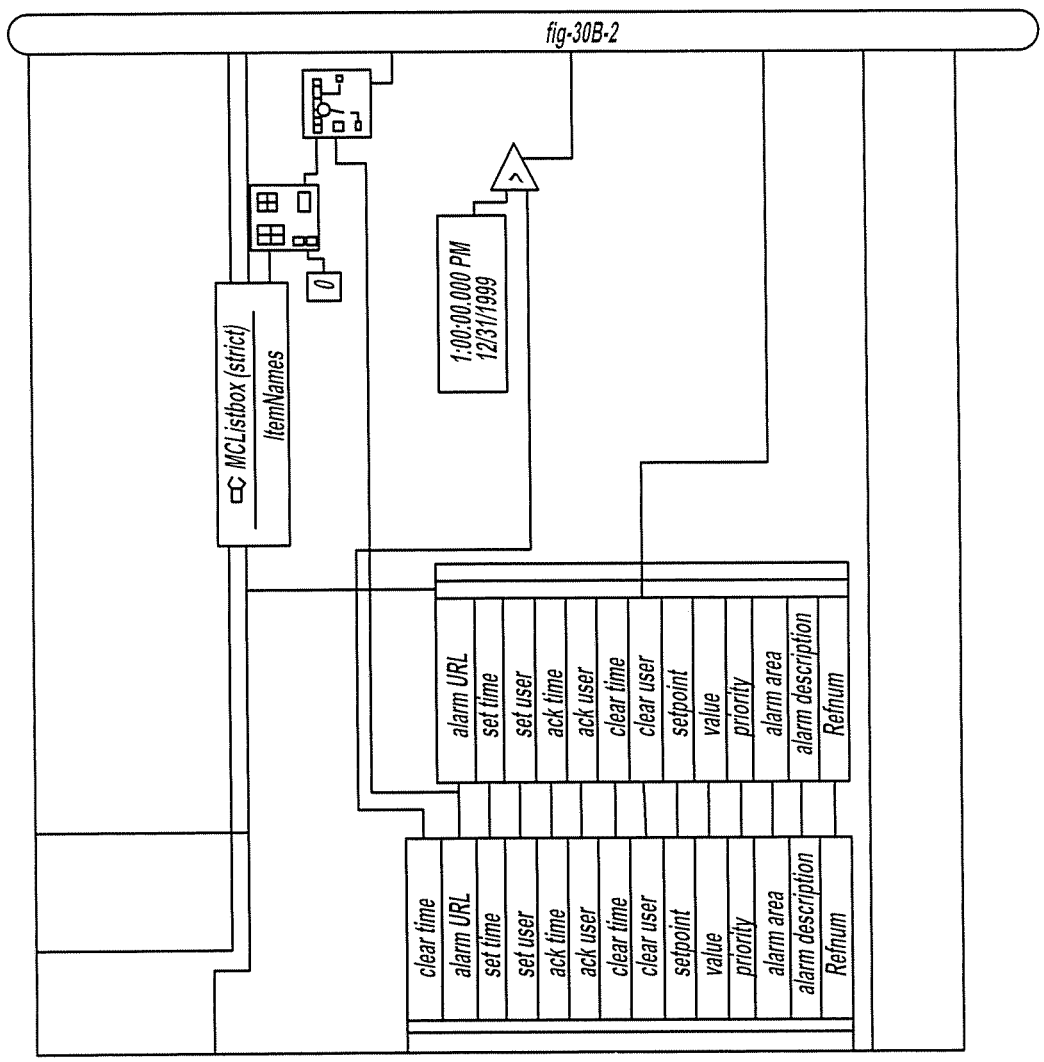
Figures 2, 30B:
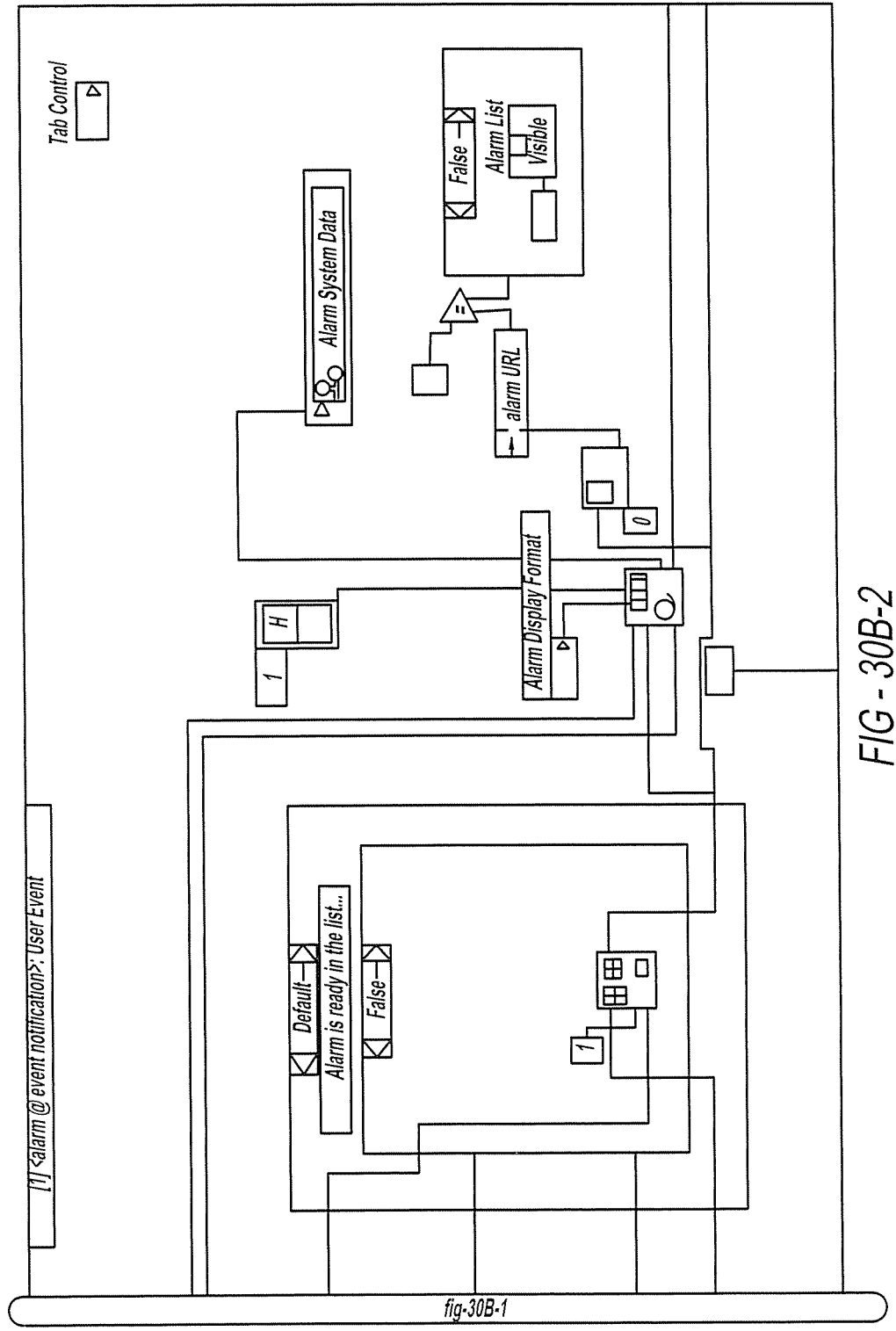
Figures 3, 30B:
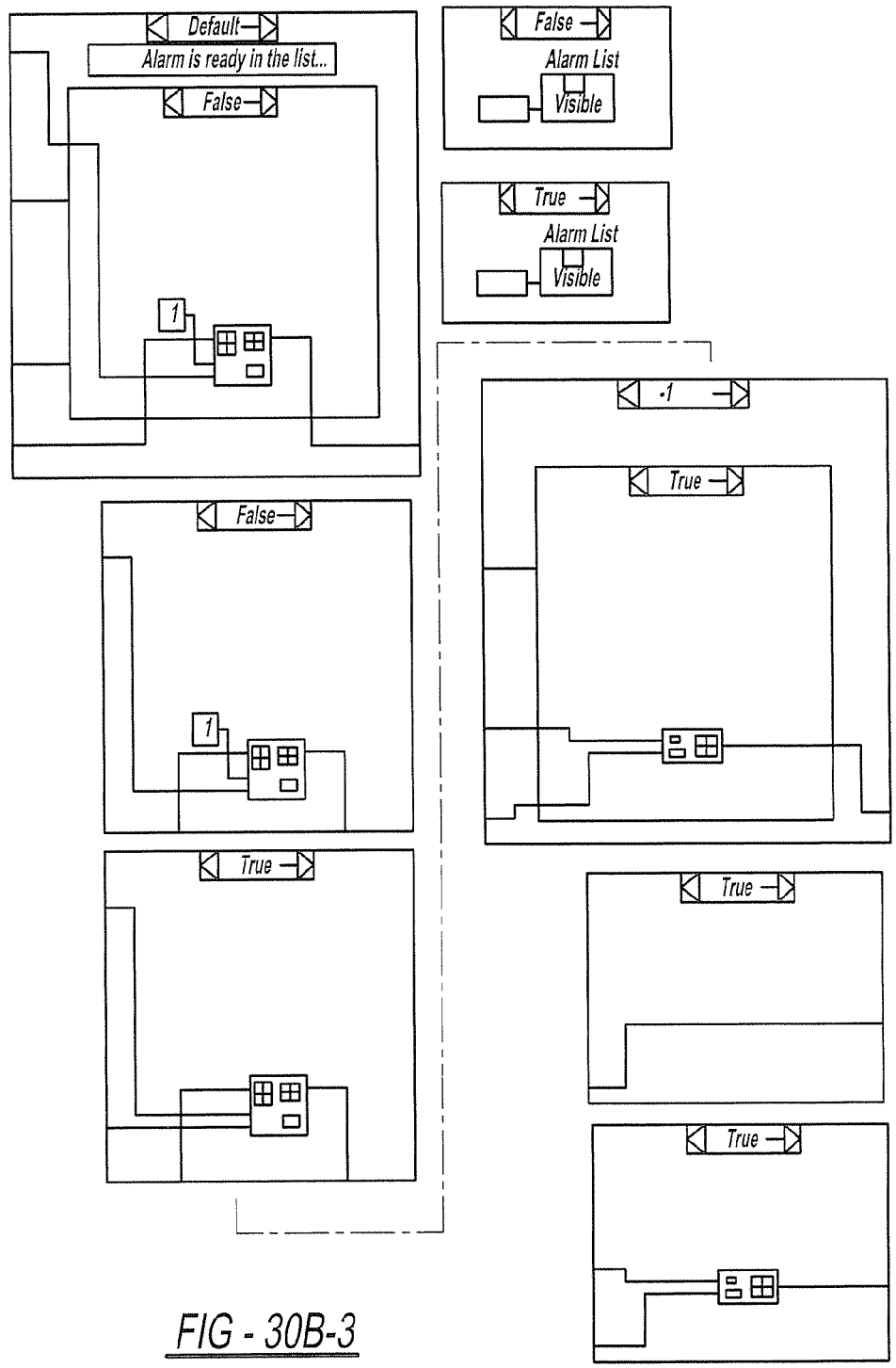
Figures 1, 30C:
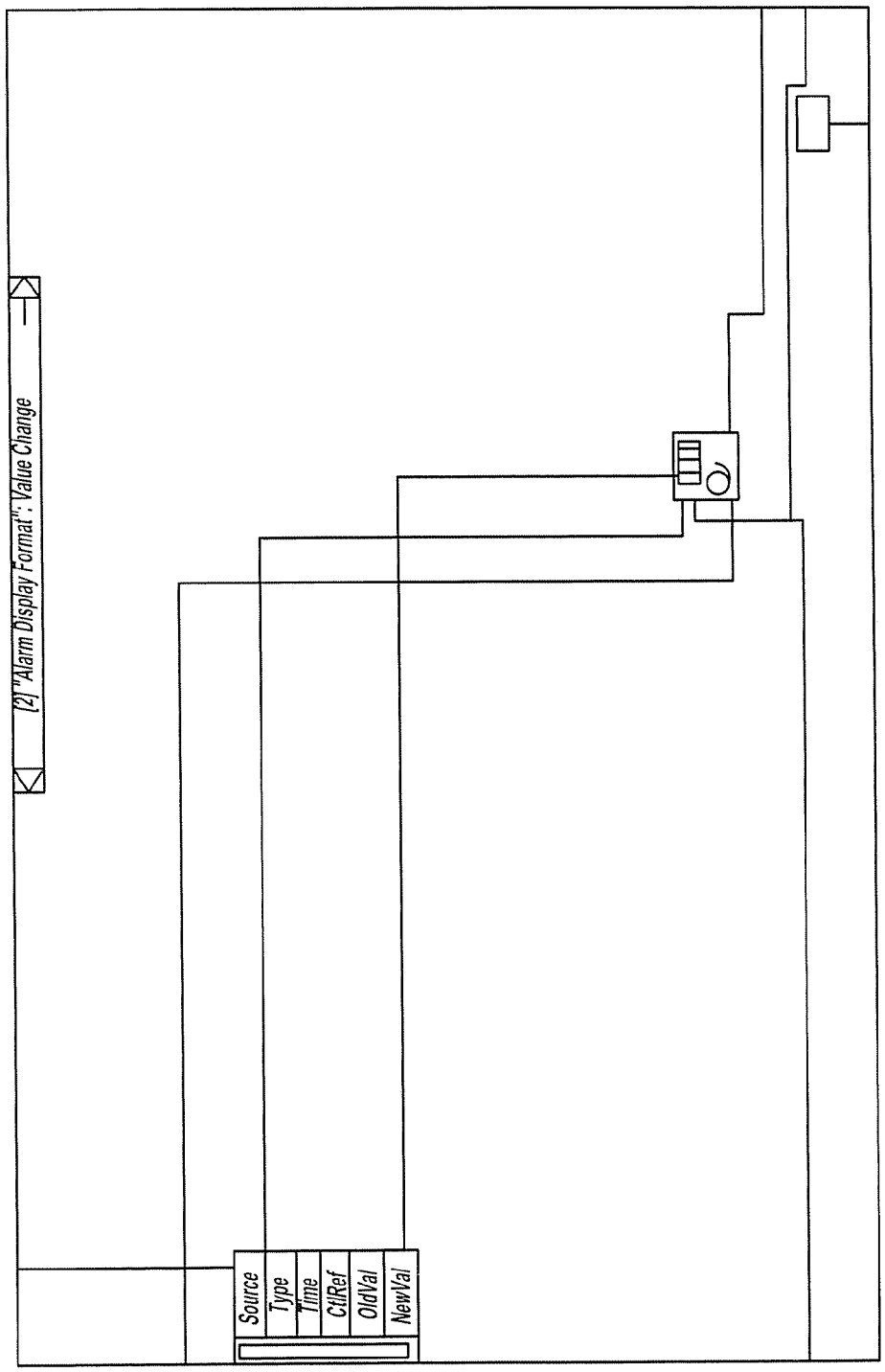
Figures 2, 30C:
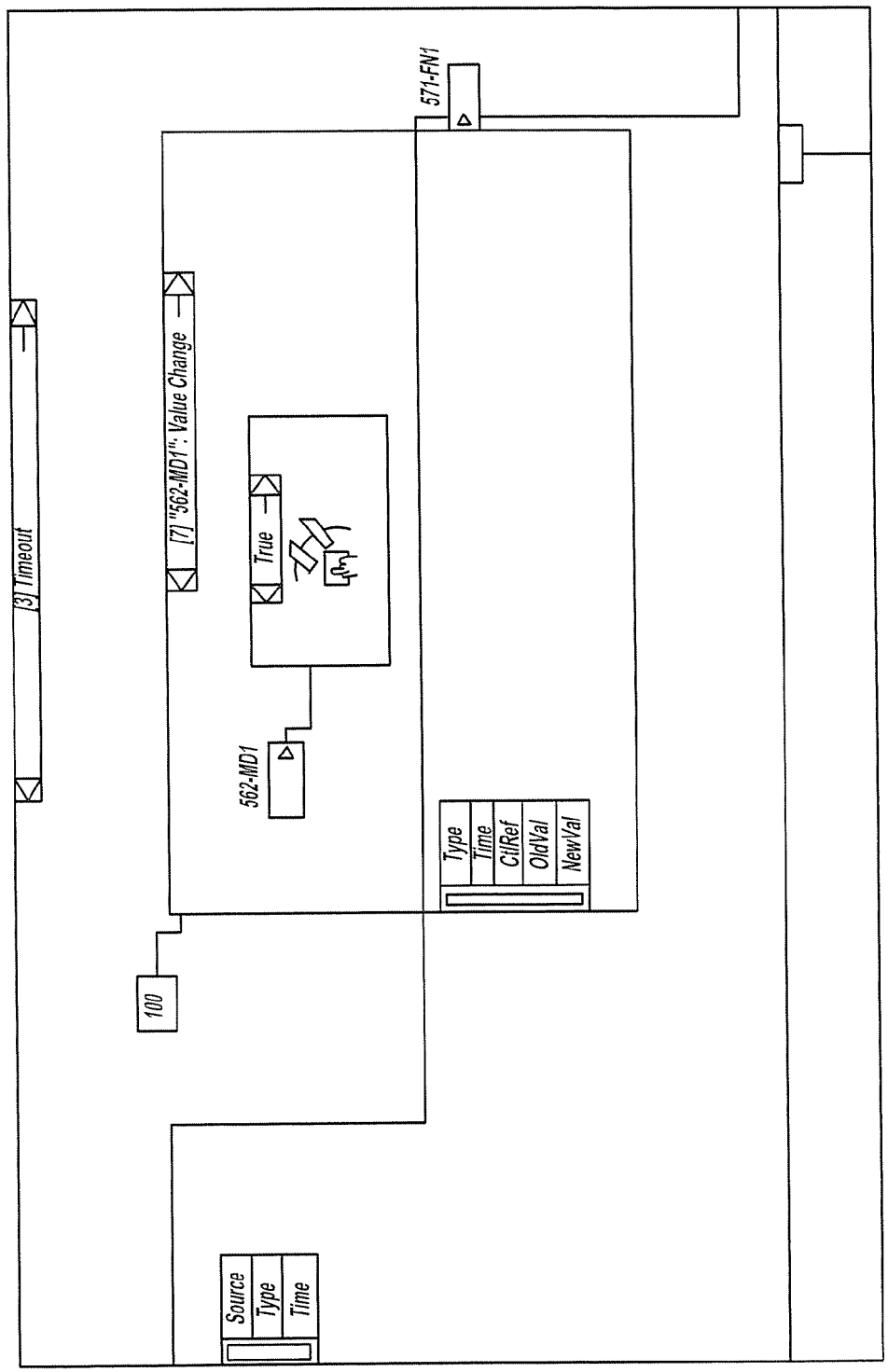
Figures 1, 30D:
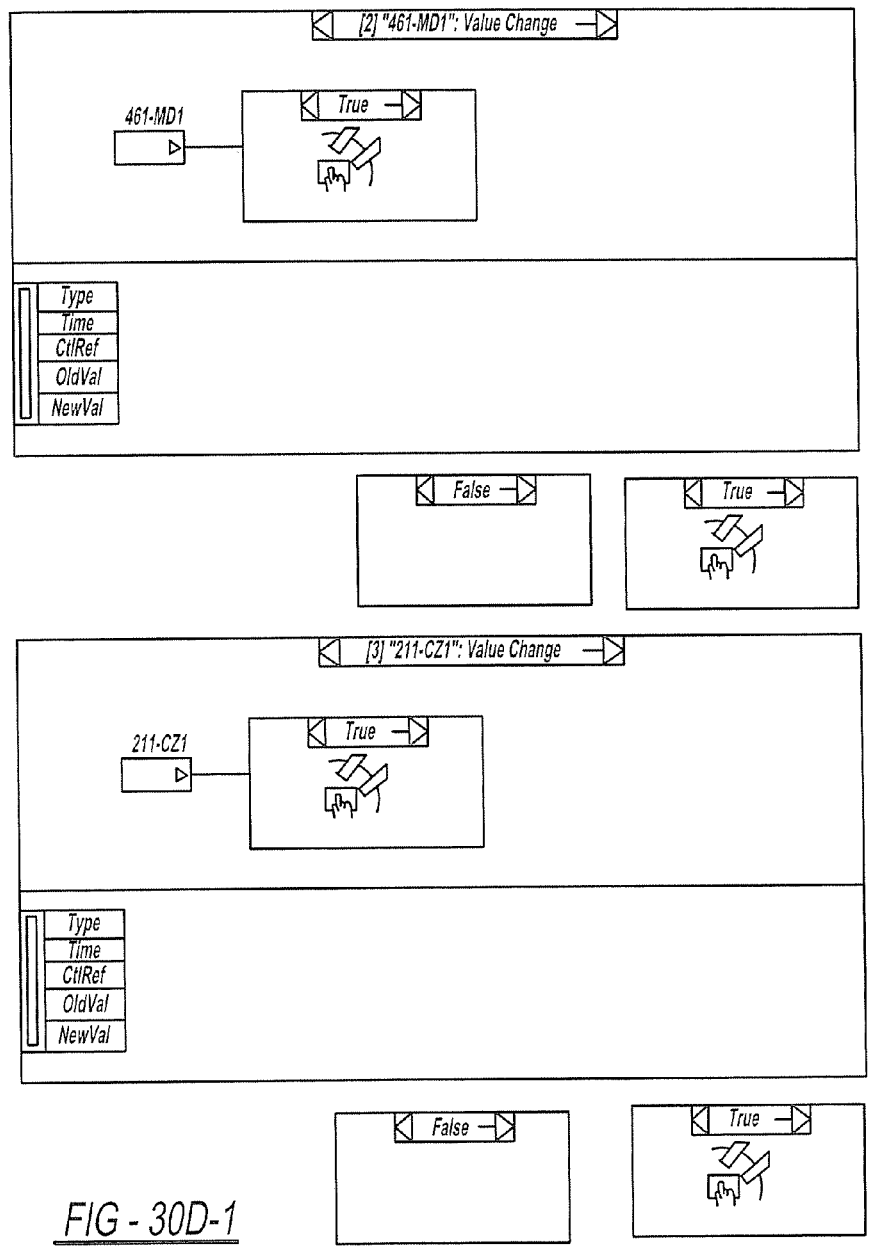
Figures 1, 30E:
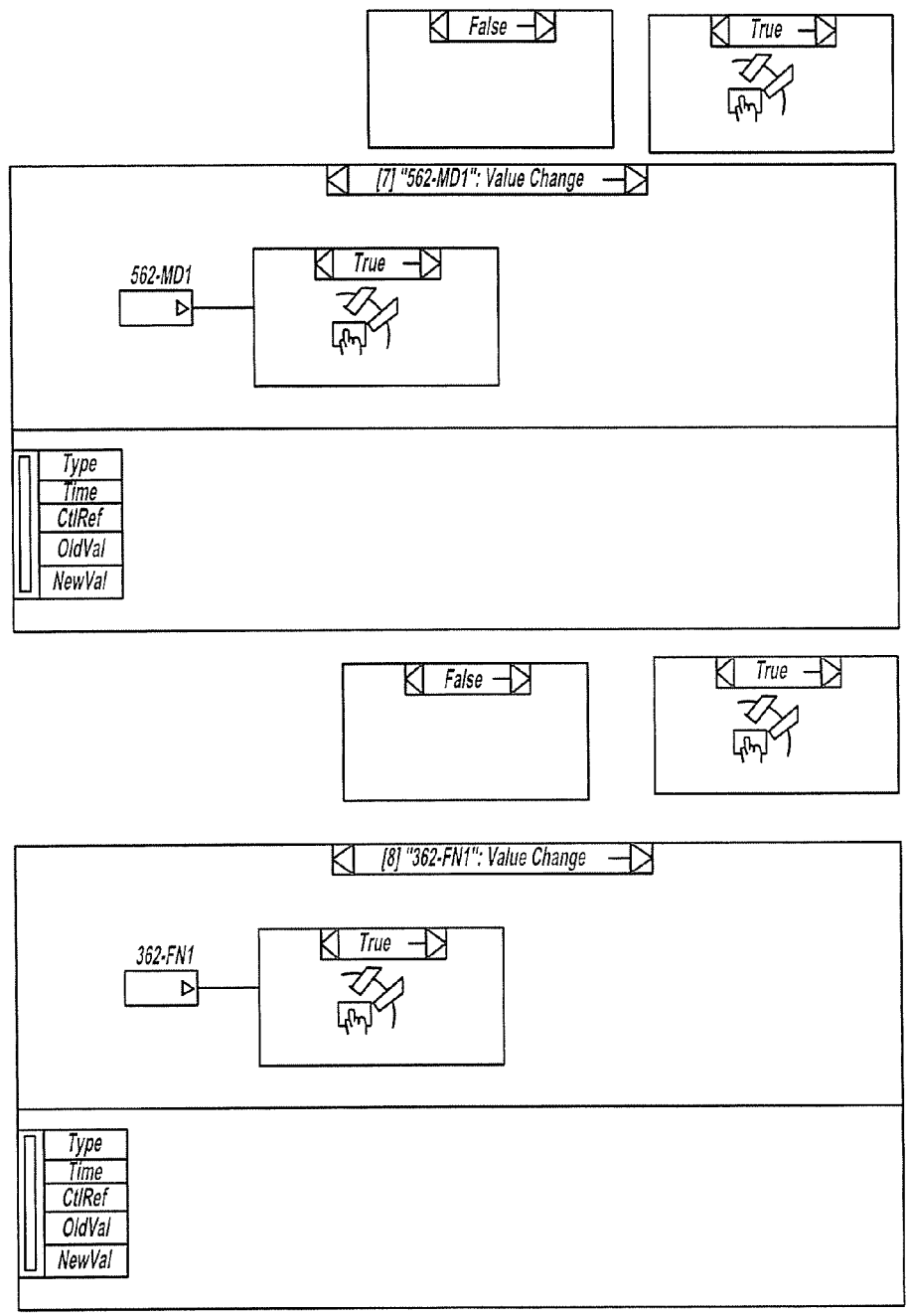
Figures 2, 30E:
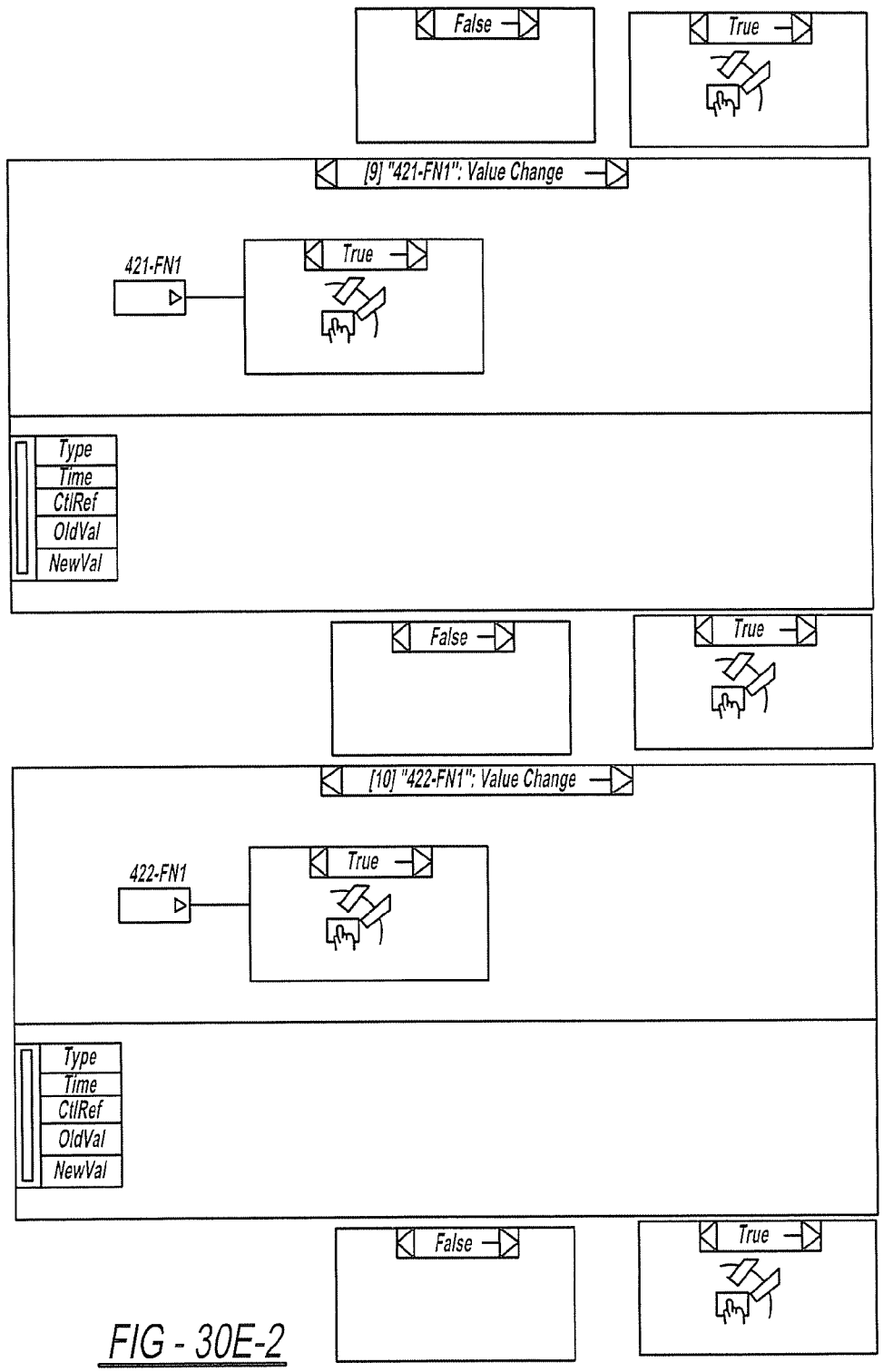
Figures 1, 30F:
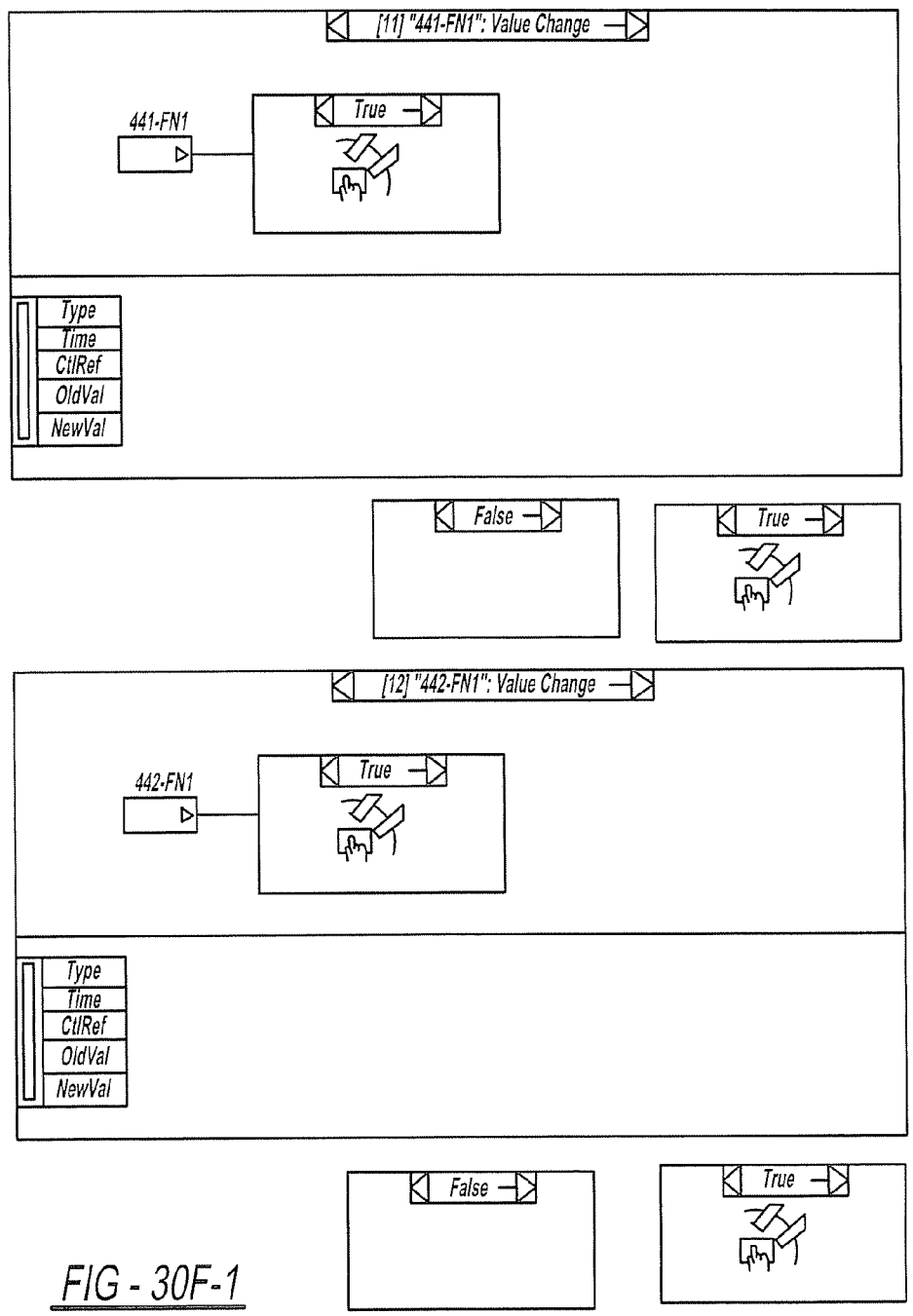
Figures 2, 30F:
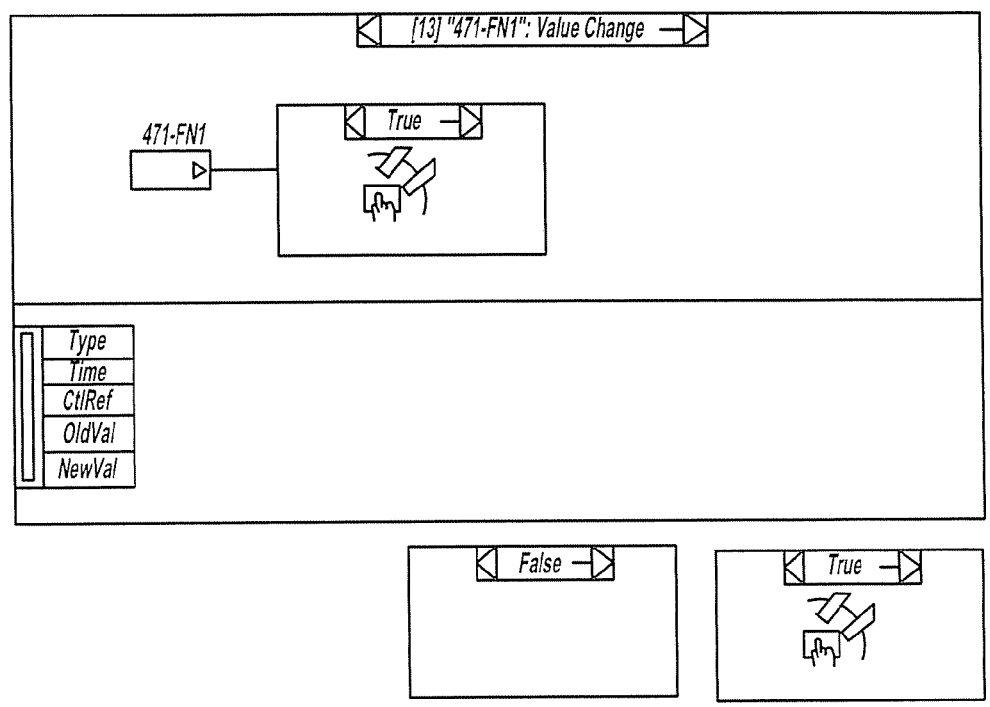
Figures 3, 30F:
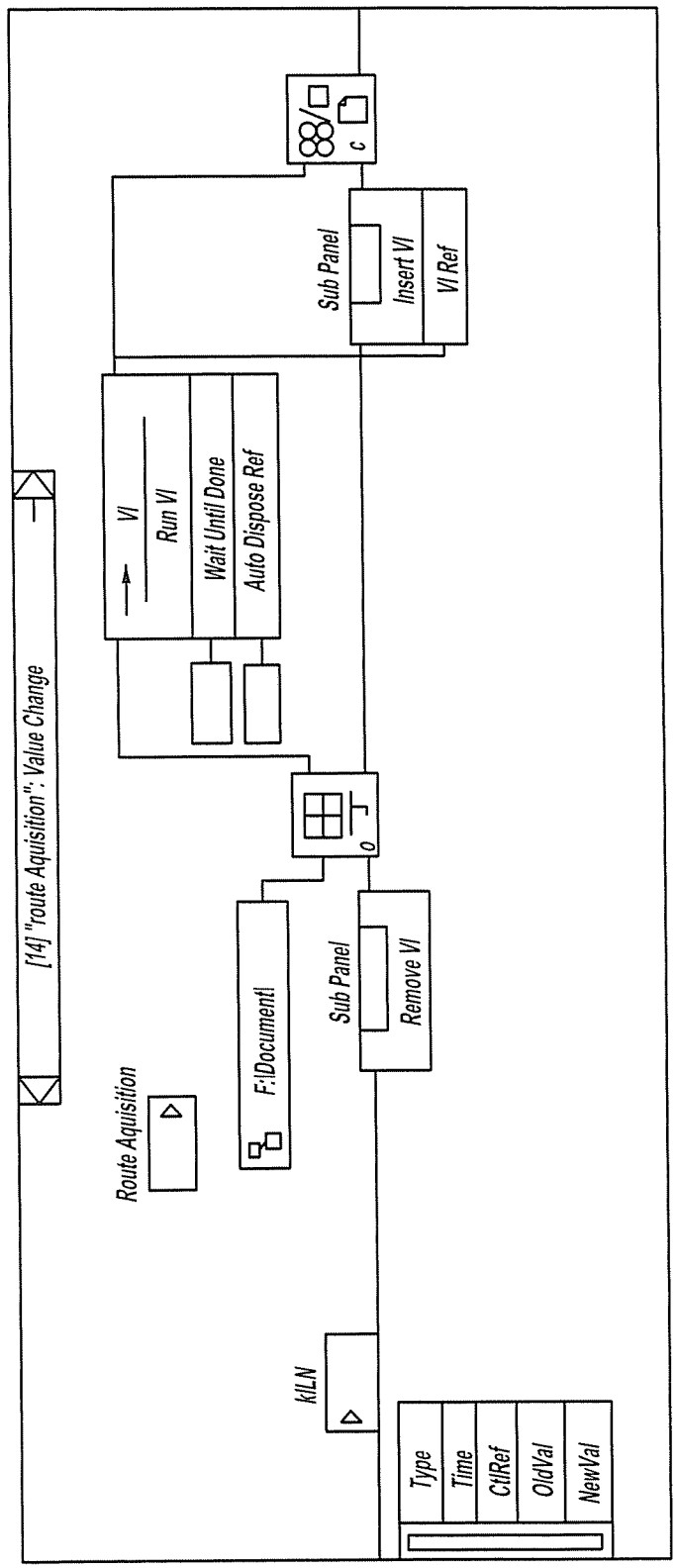
Figures 4, 30F:
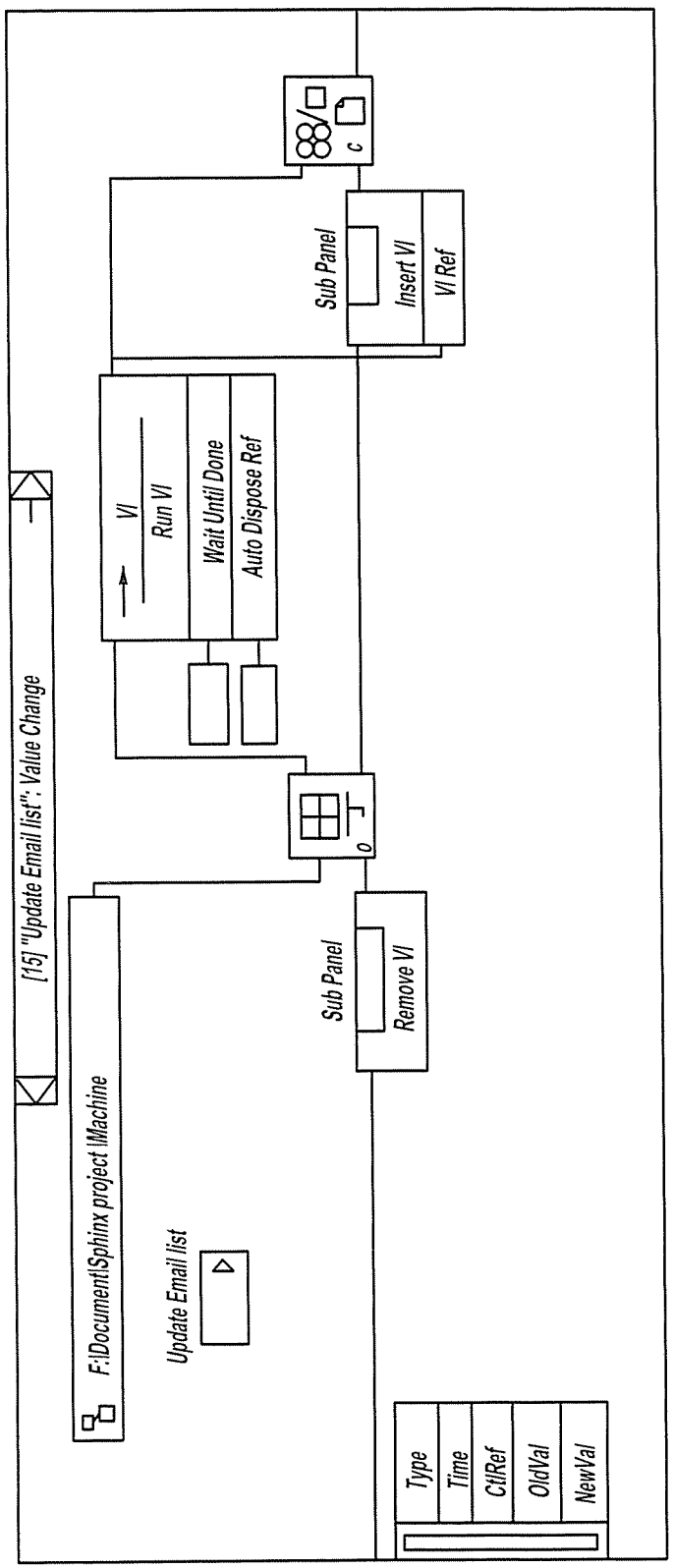
Figures 1, 30G:
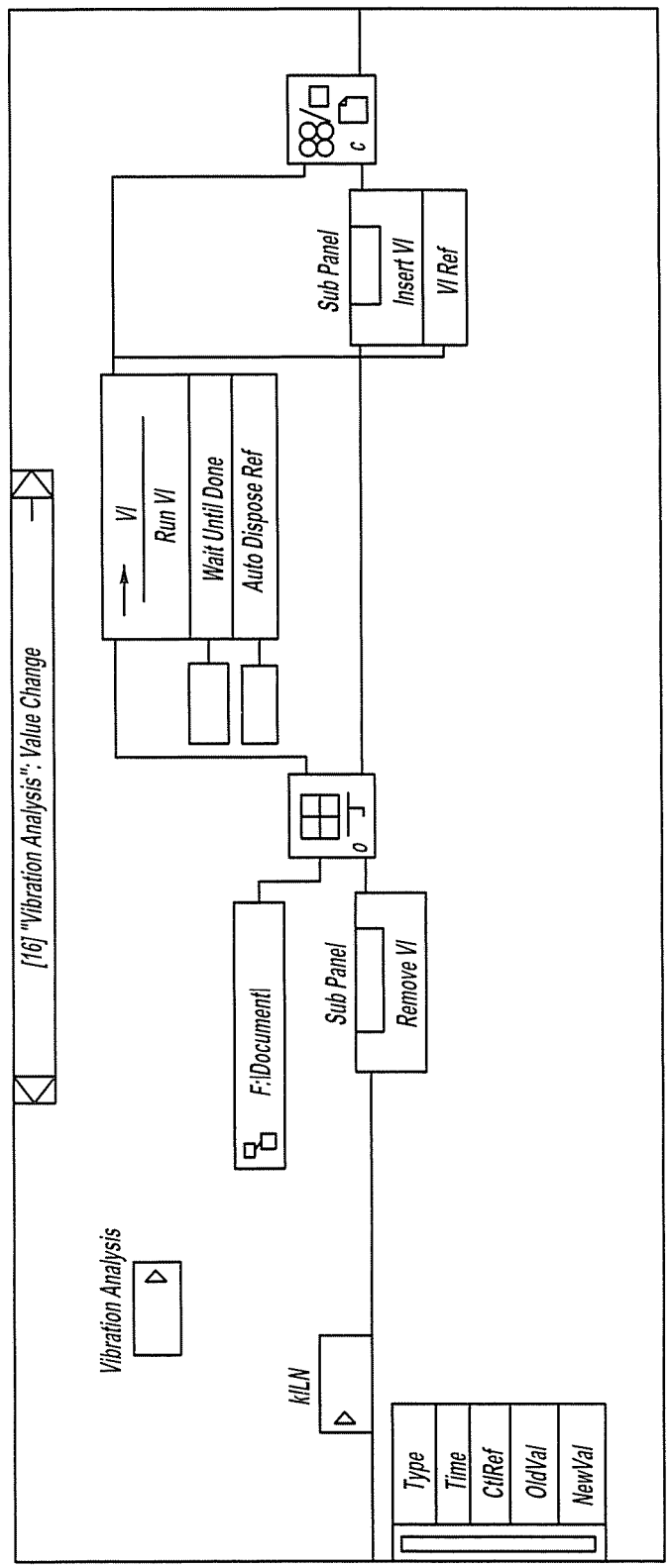
Figures 2, 30G:
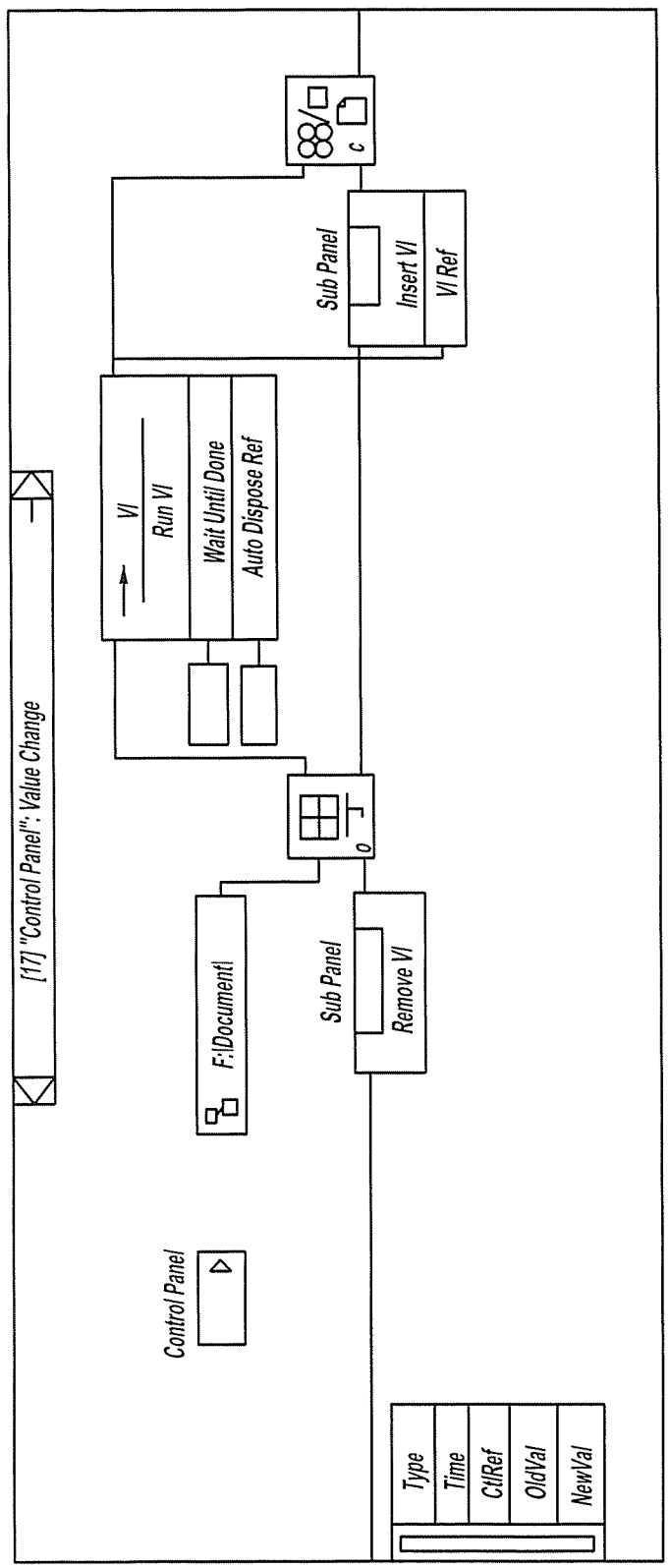
Figure 31A:
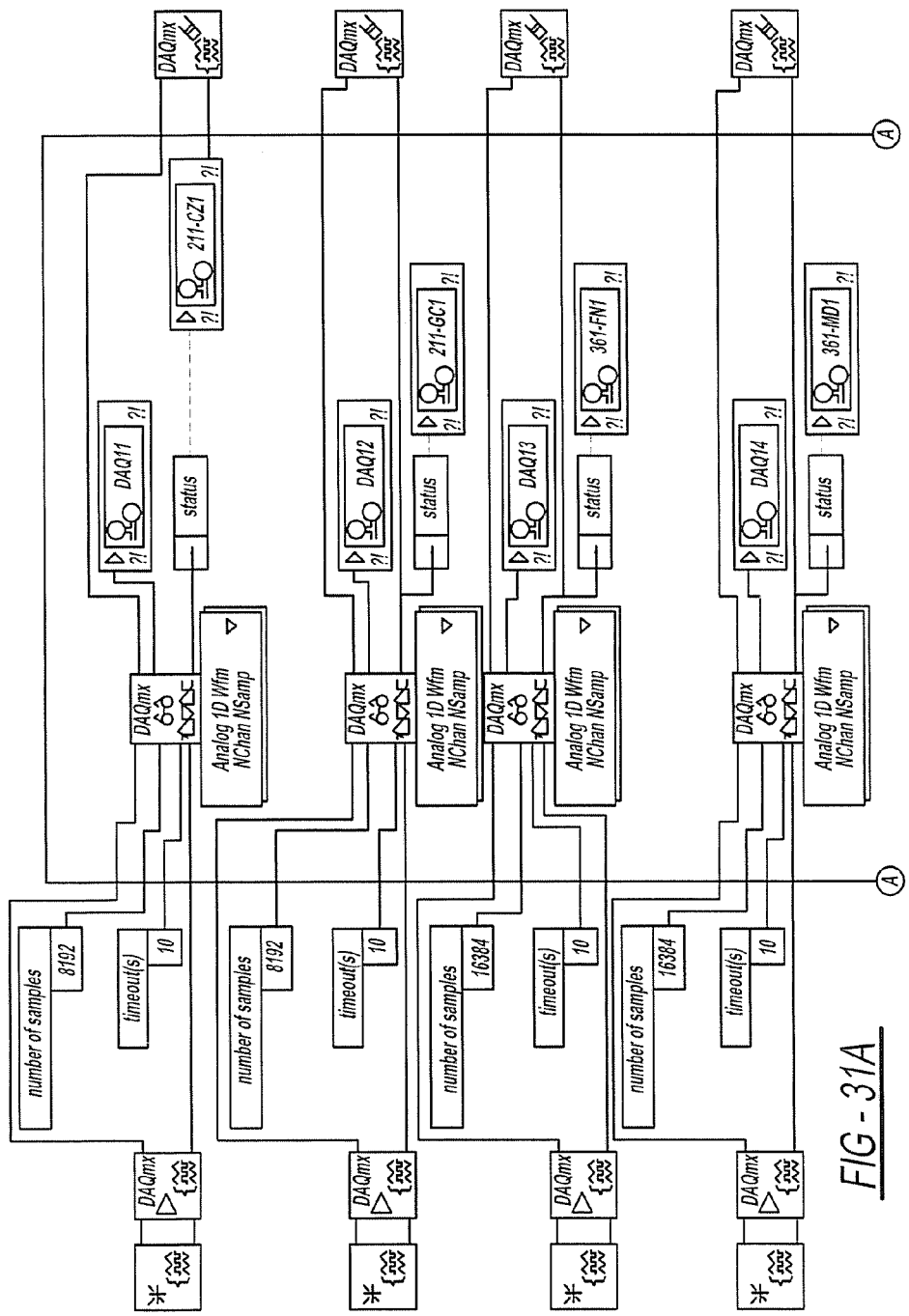
Figure 31B:
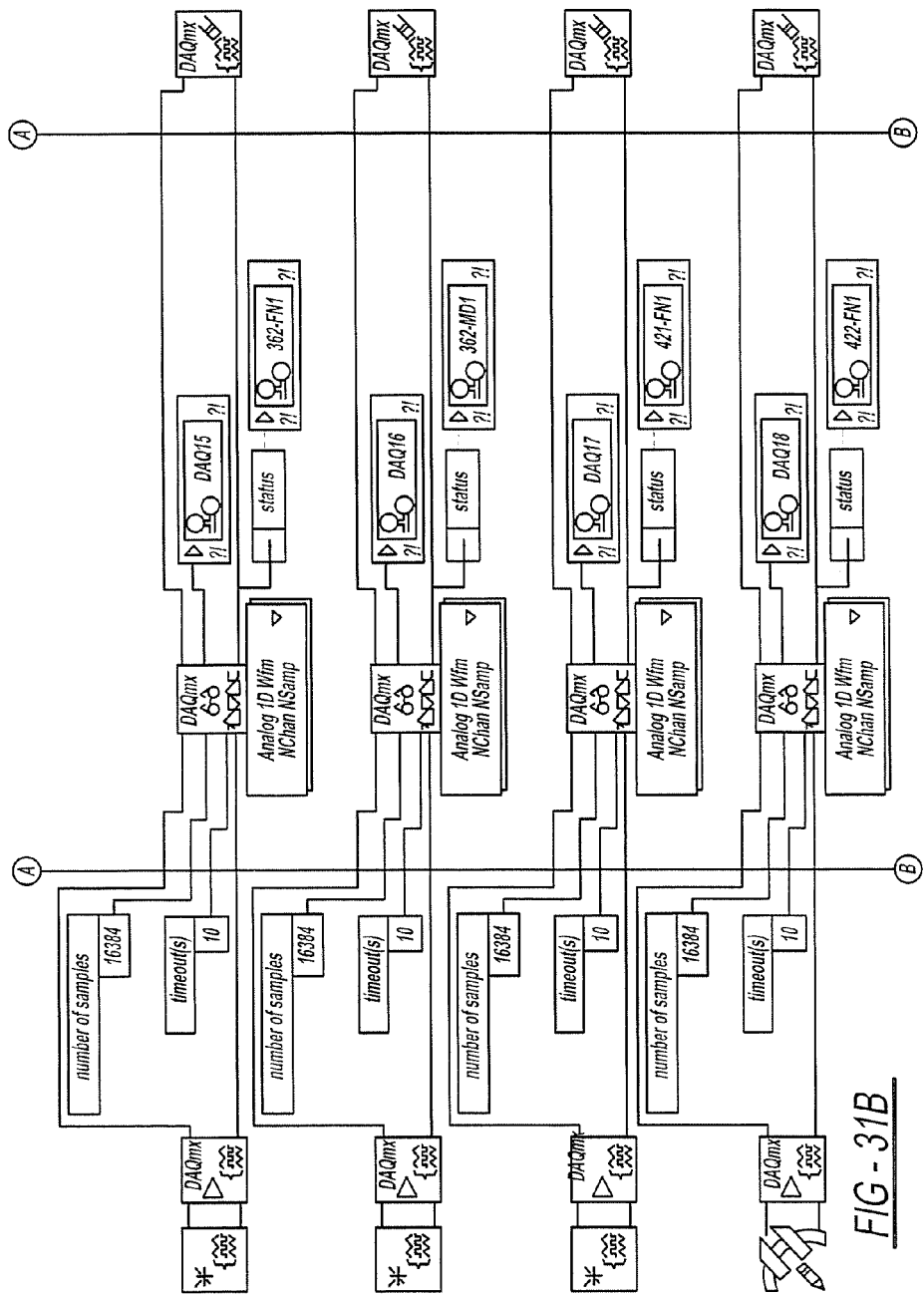
Figure 31C:
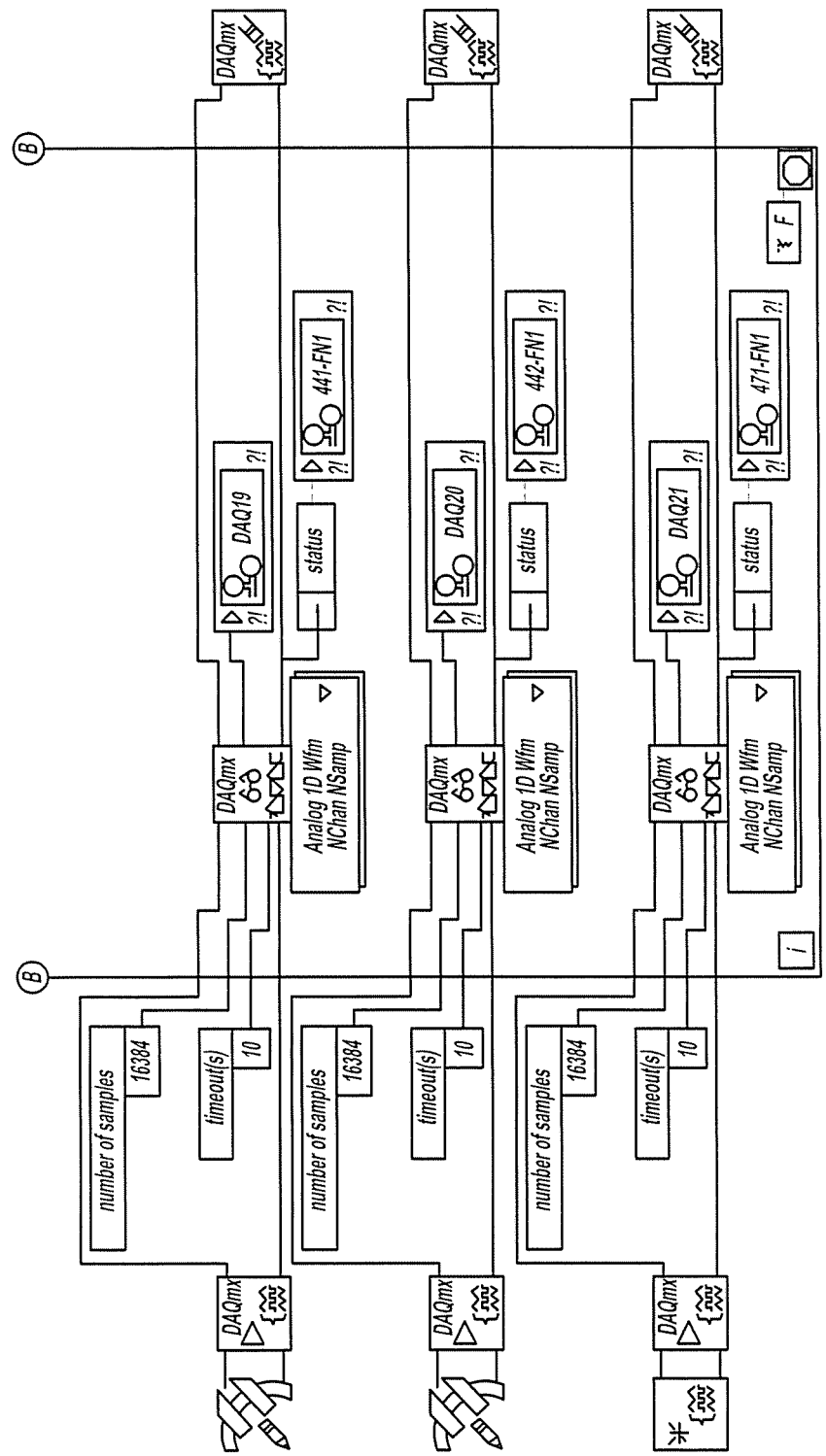
Figure 32A:
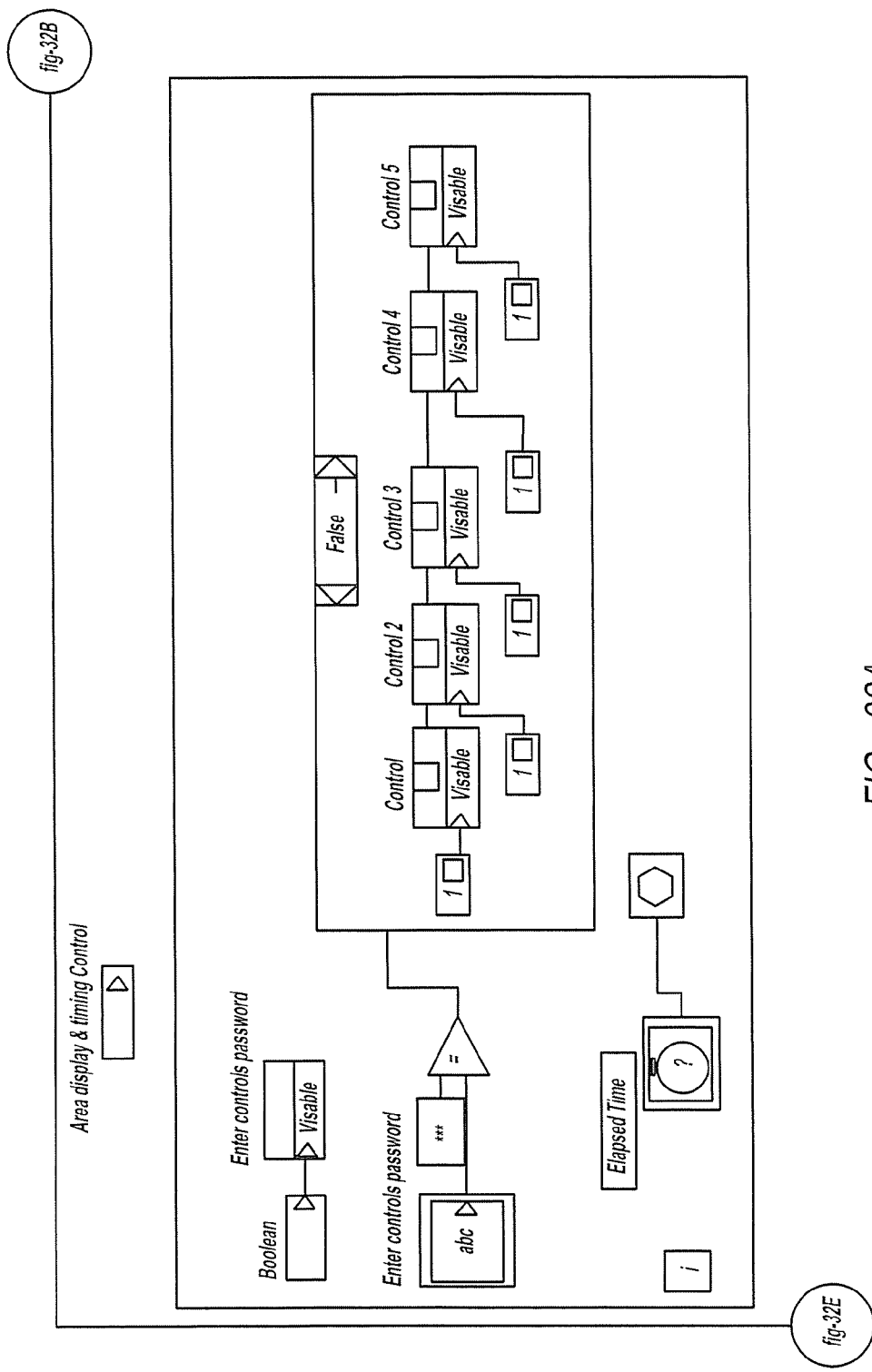
Figure 32B:
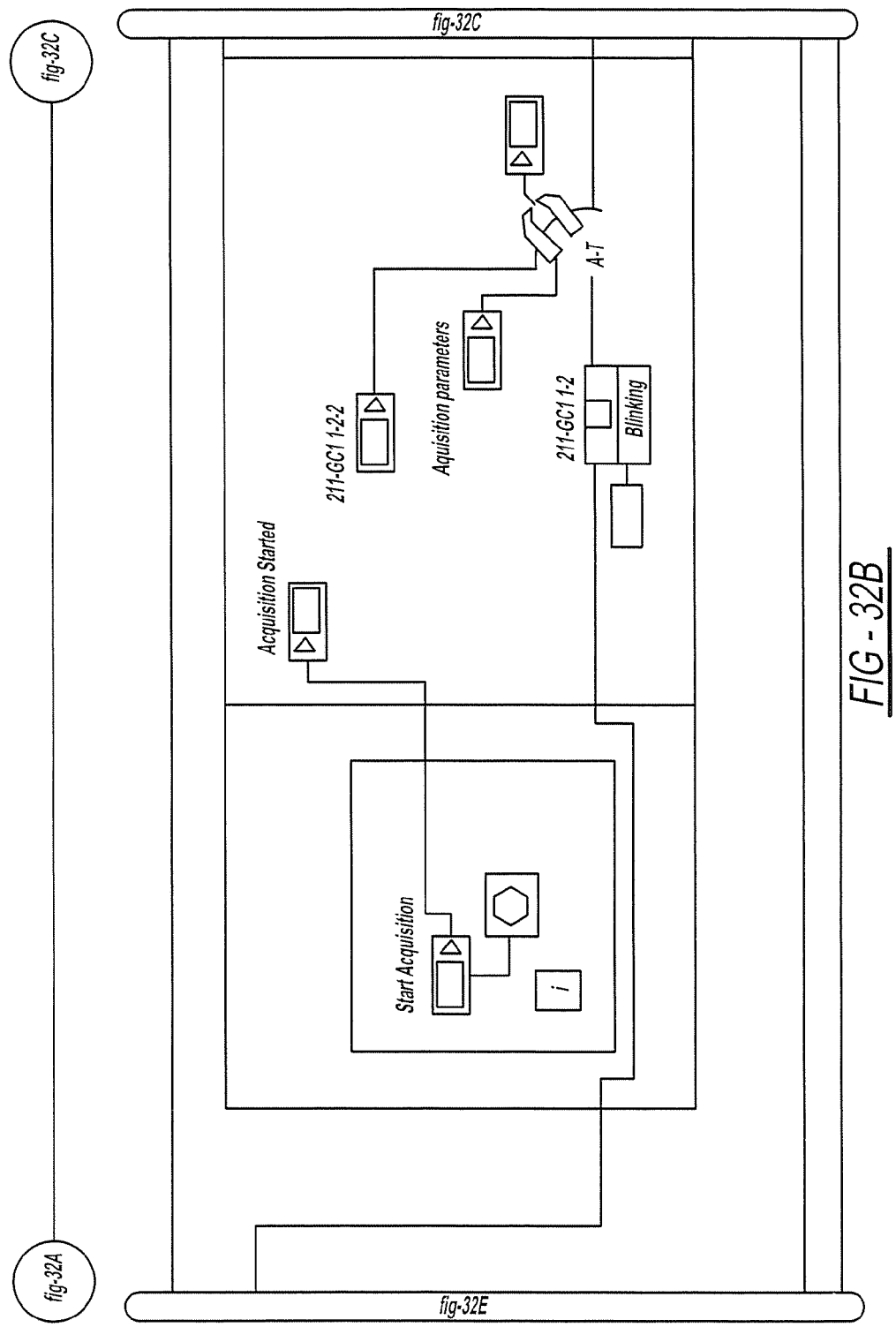
Figure 32C:
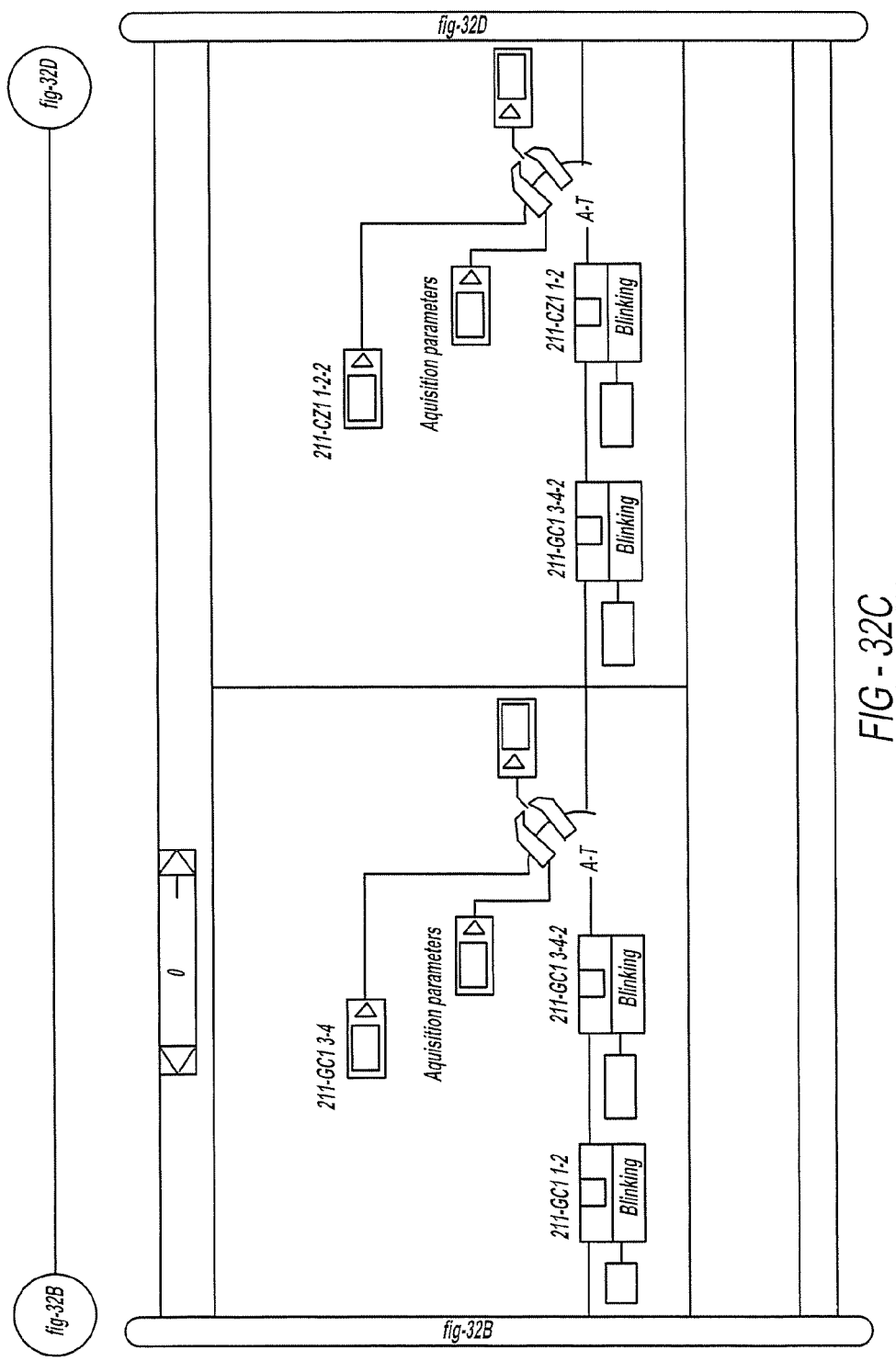
Figure 32D:
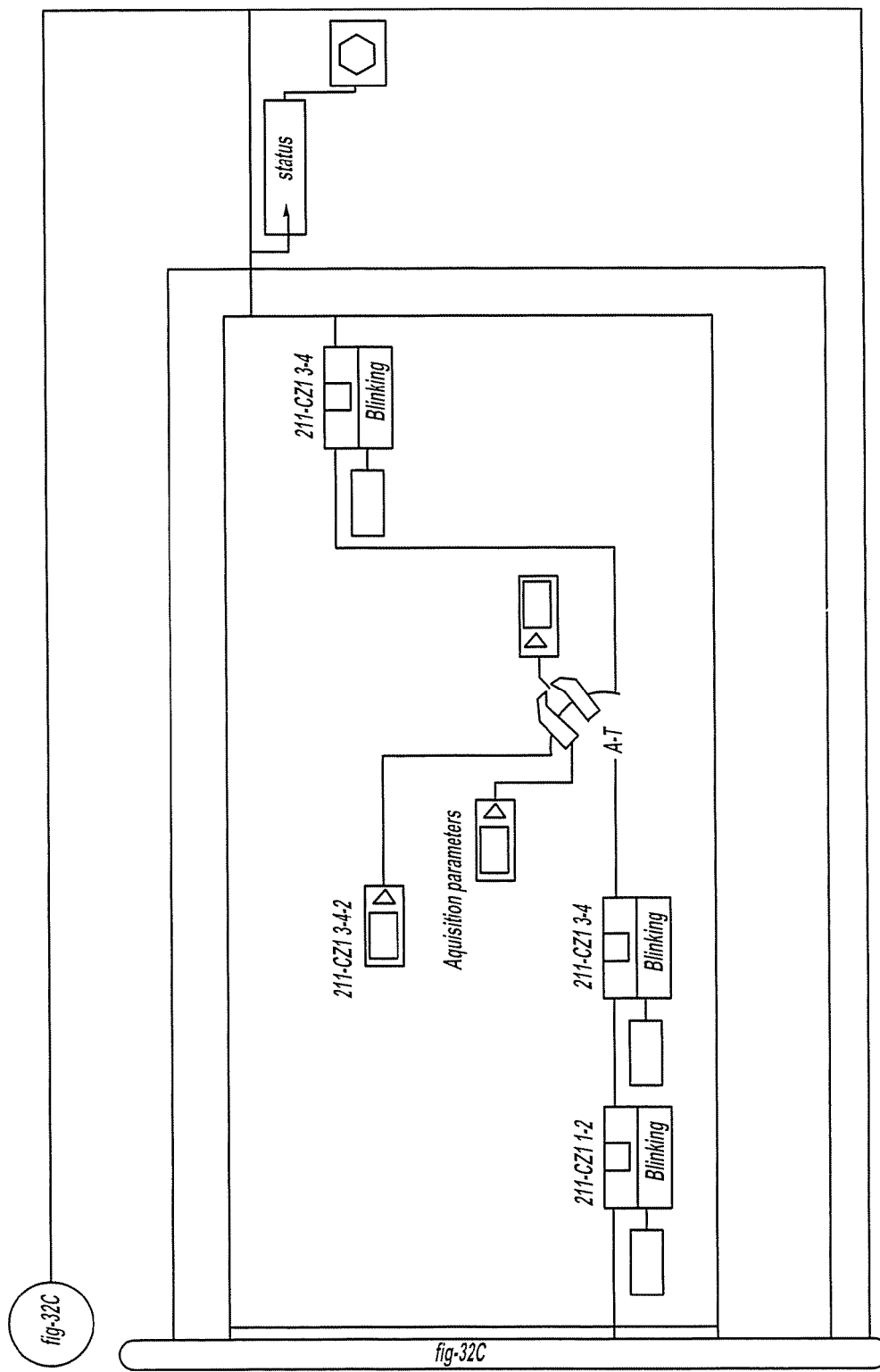
Figure 32E:
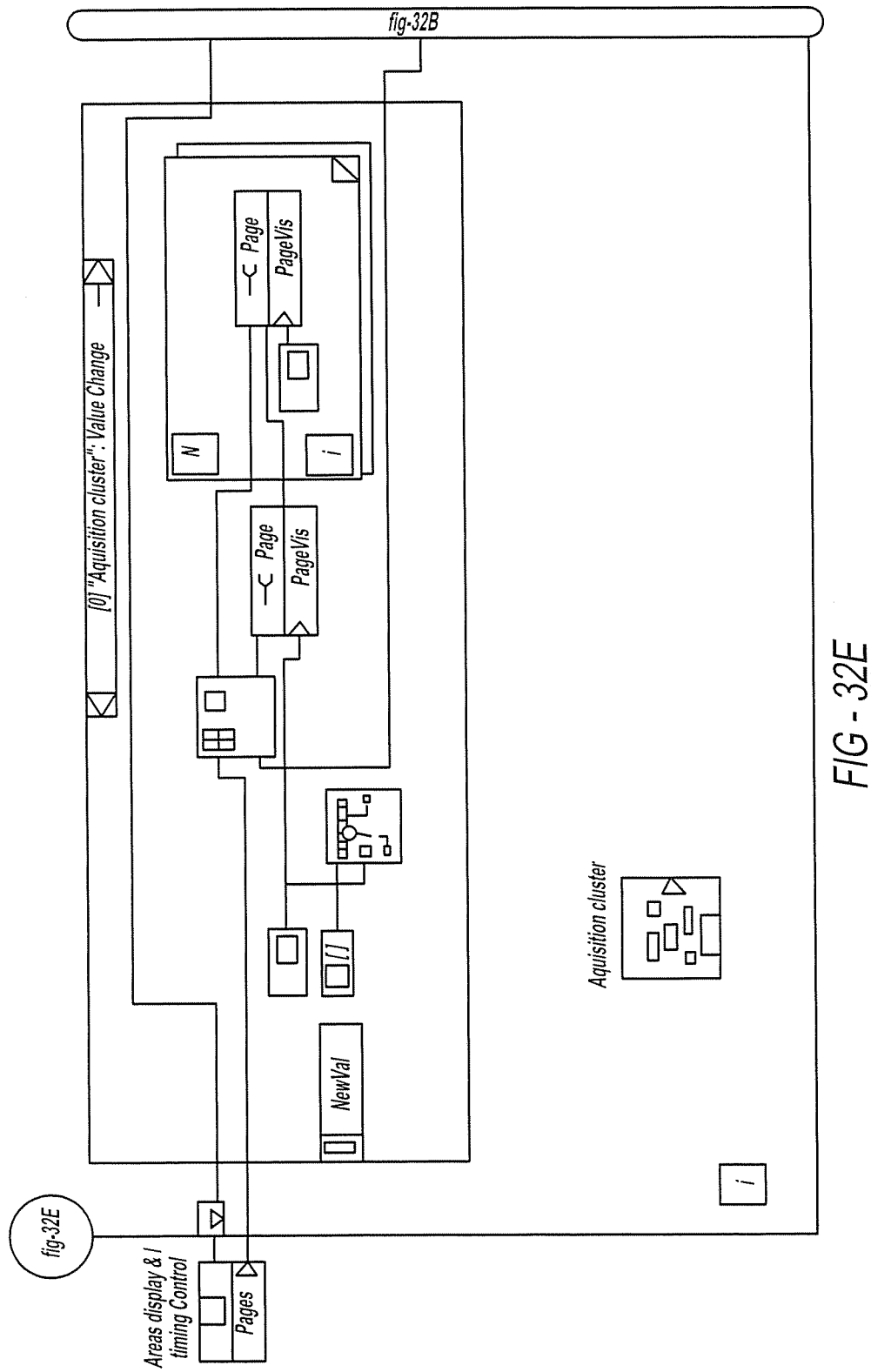
Figure 32F:
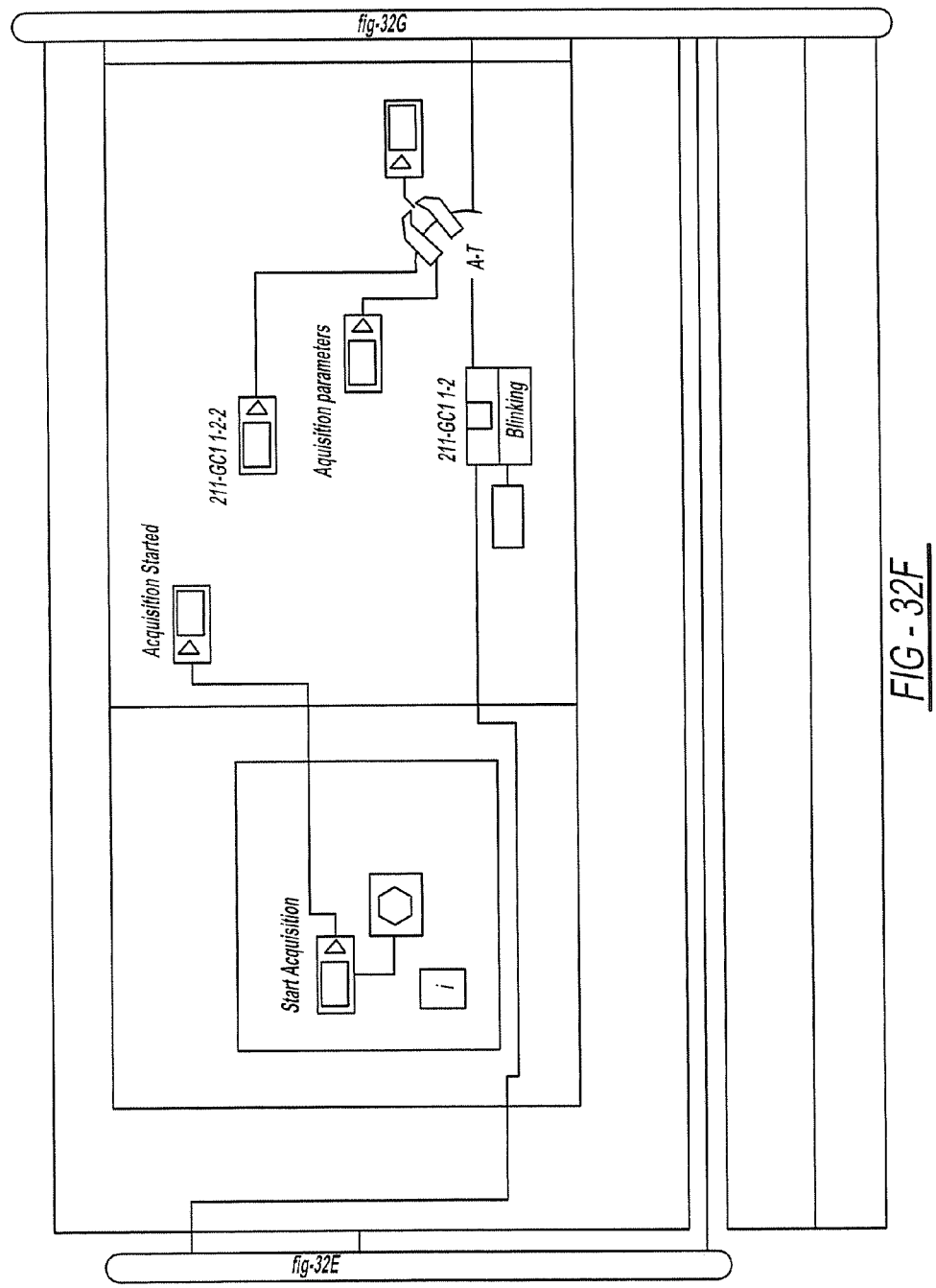
Figure 32G:
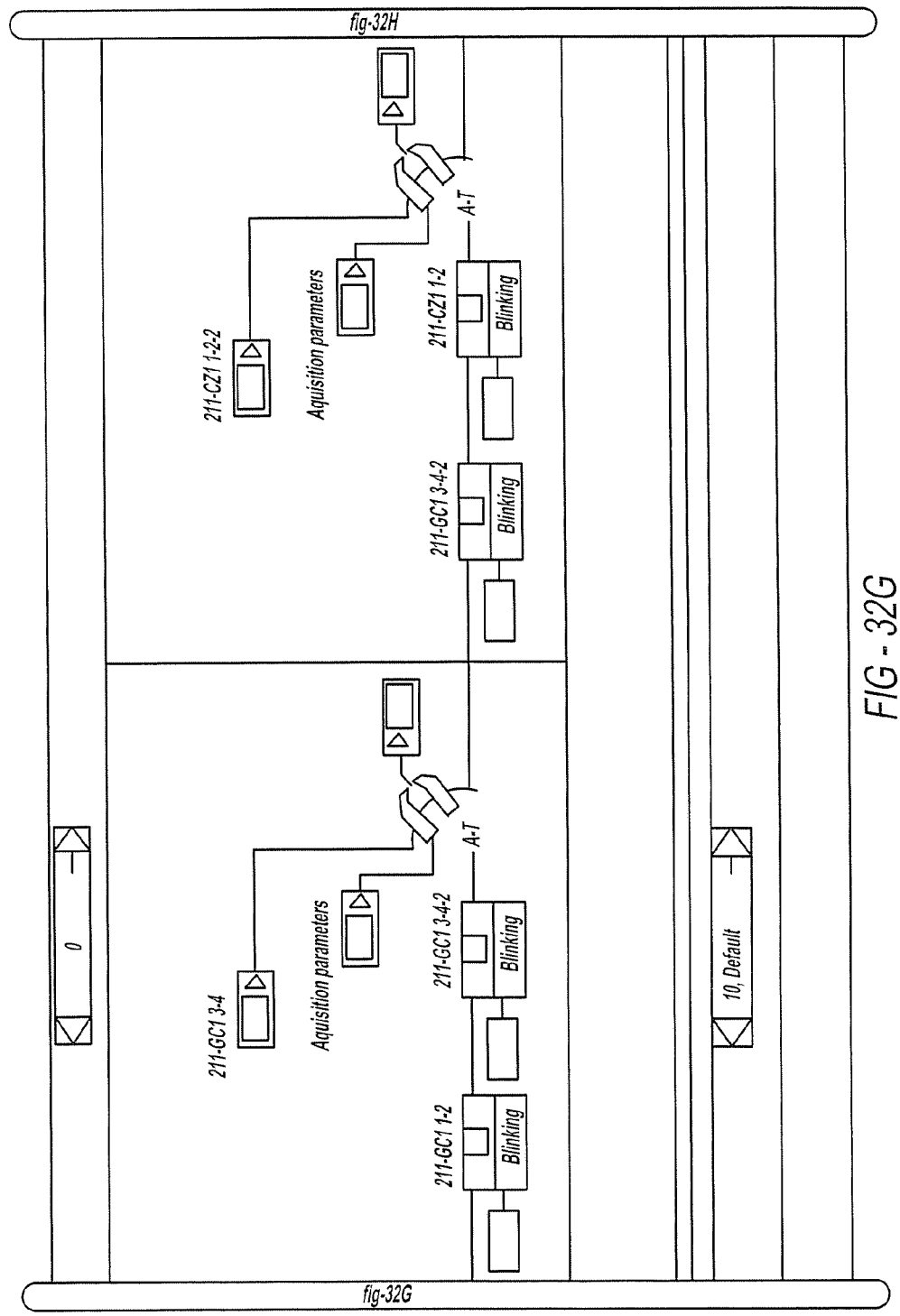
Figure 32H:
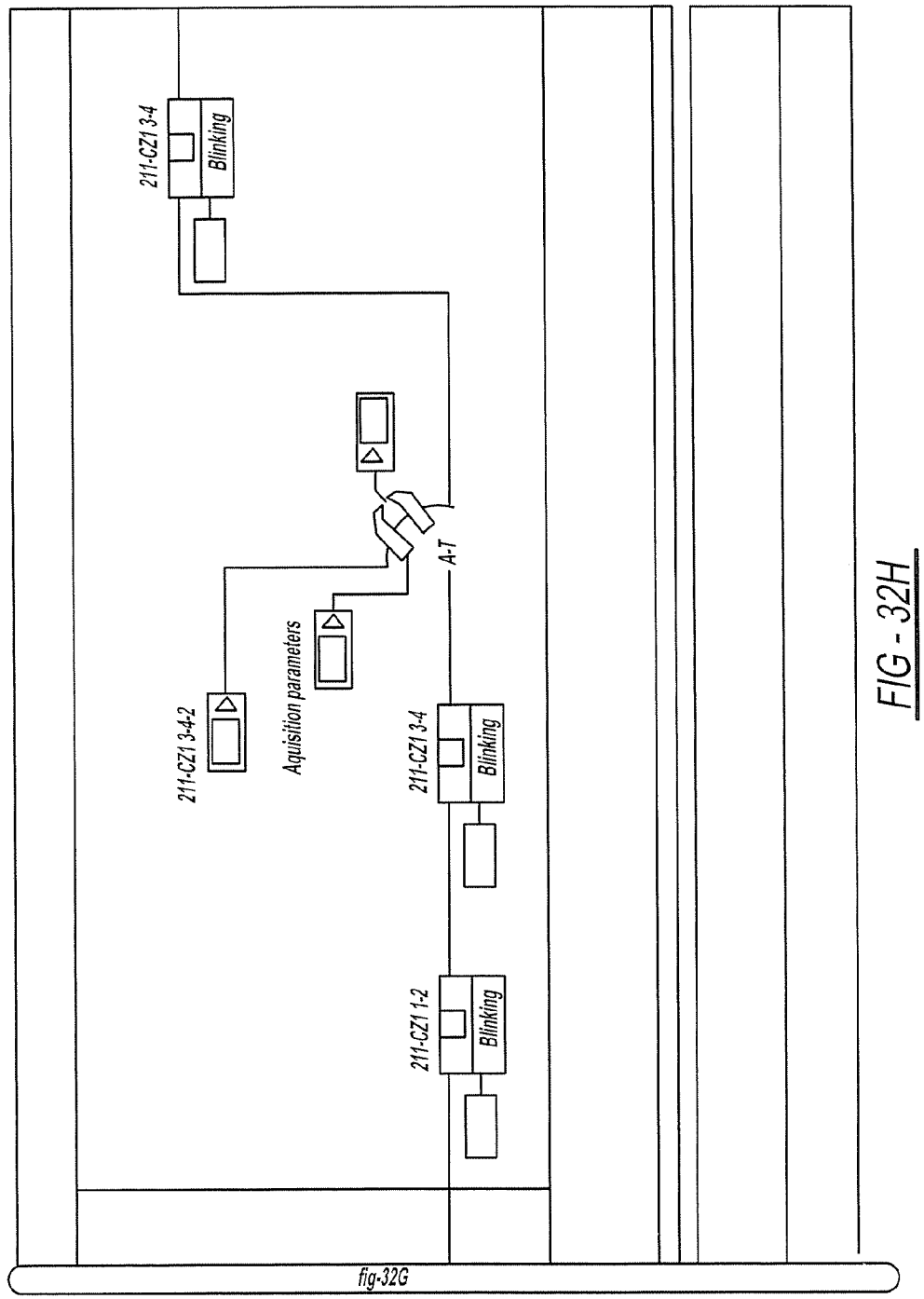
Figure 321:
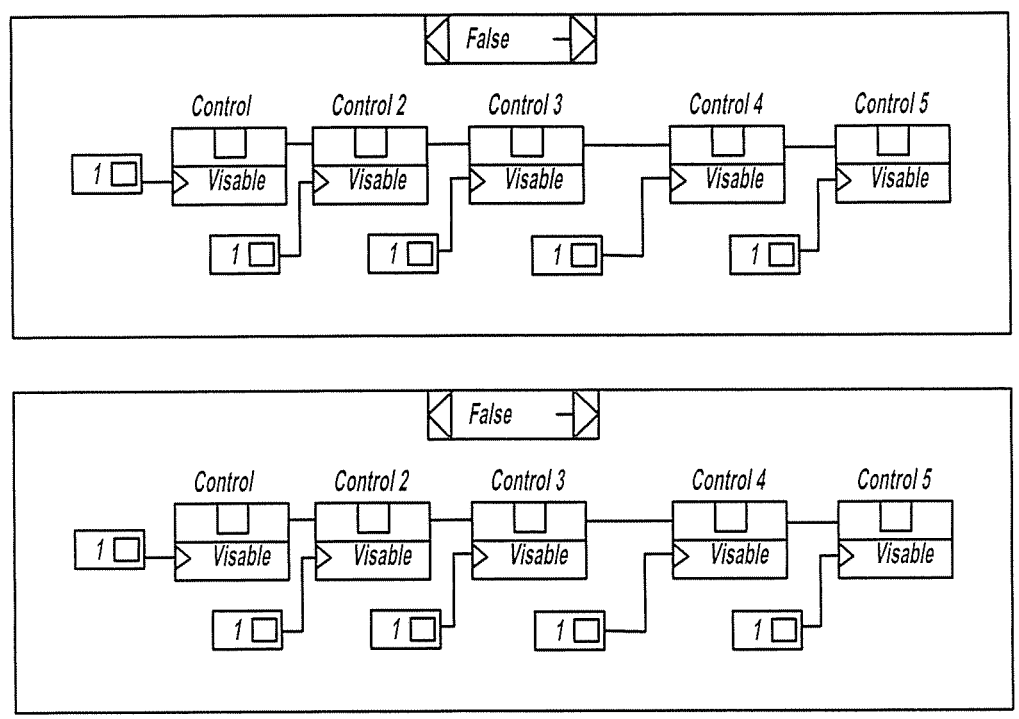
Figure 32J:
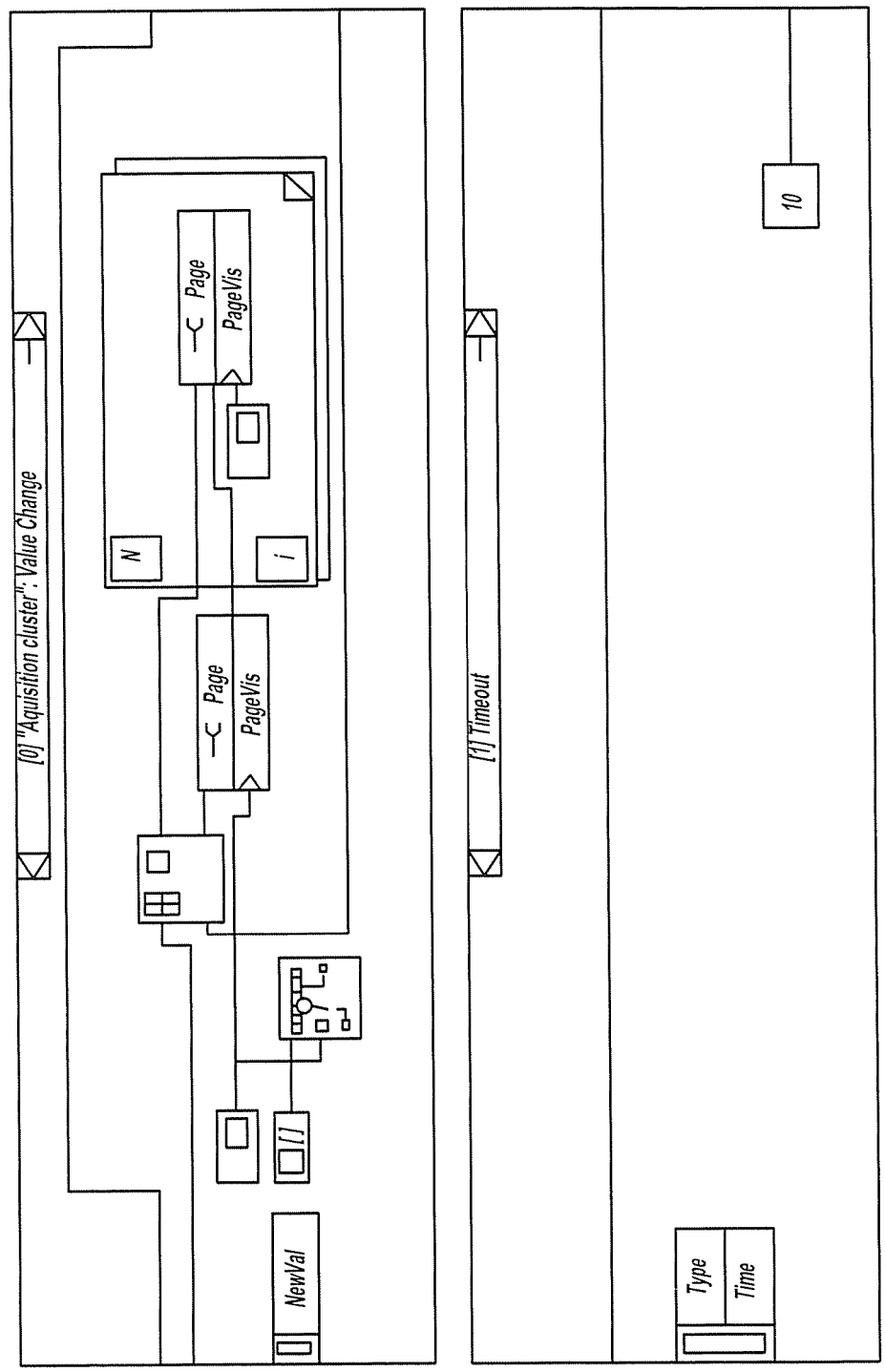
Figure 32K:
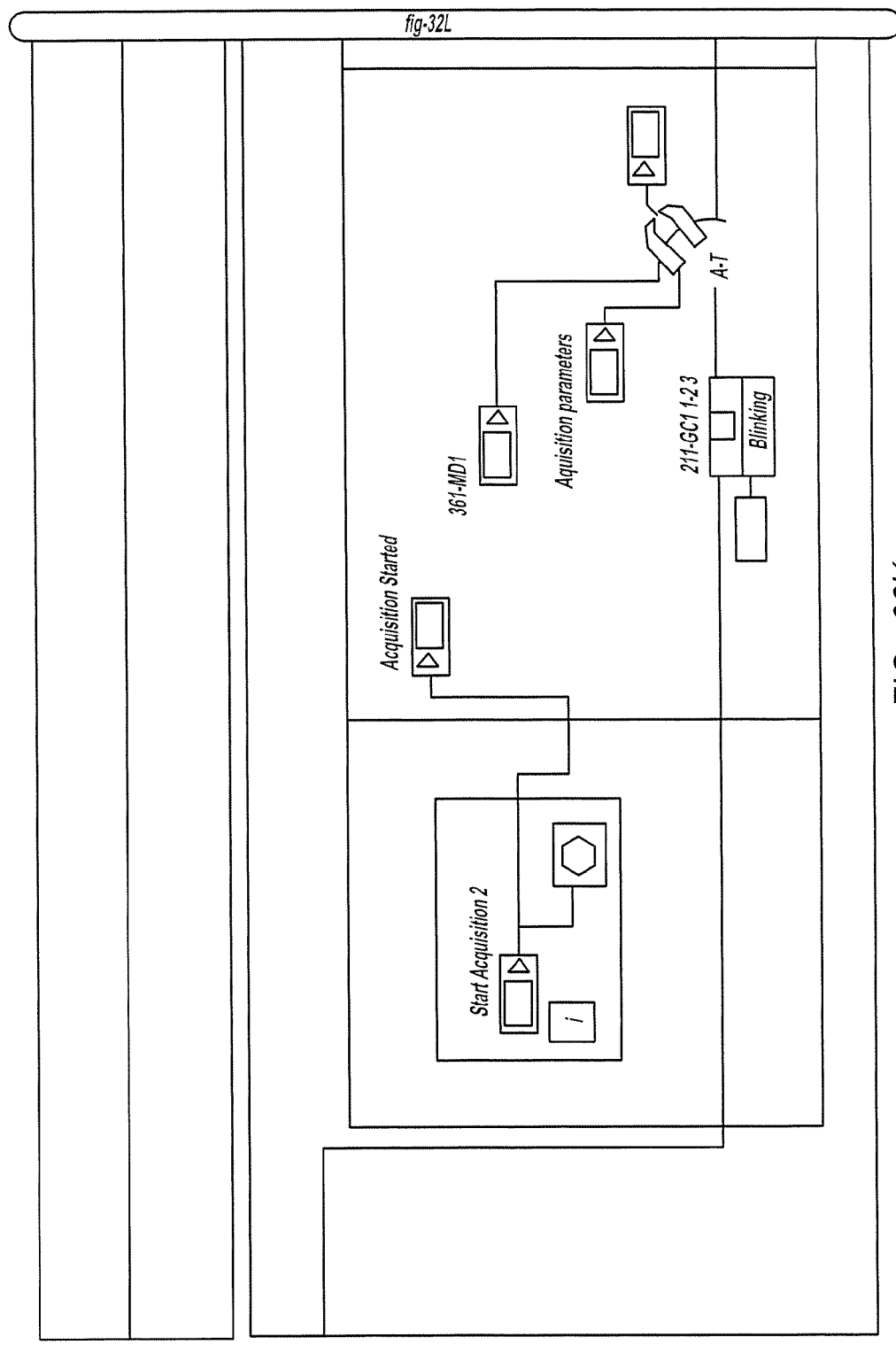

A route acquisition interface software flow diagram is shown in FIG. 29, which corresponds to FIG. 21. This is used by the analyst to route the automatically collected data to the hand-held data acquisition units 411 (see FIG. 19) which are used by the plant technicians for intermittent monitoring on a non-real time basis, and for manual analysis. The actual software coding algorithms are shown in FIGS. 30A through 32M. These software charts are shown in the Labview® coding language from National Instruments Corp.

While the preferred embodiment of the present system for monitoring plant equipment has been disclosed, it should be appreciated that other variations may be employed. For example, additional machinery components may be monitored on a real-time and continuous basis and other types of sensors, detectors and monitoring devices may be provided, although various advantages in the present system may not be realized. Furthermore, additional, less or different computer and communications hardware items may be used although certain functions and advantages of the present system may not be achieved. Alternate software logic and instructions may be used although certain benefits of the present system may not be fully achieved. Furthermore, certain aspects of the present system may be employed for machinery and equipment not associated with cement manufacturing, although various advantages may not be gained. For example, specific comparative, analysis and reporting features of the present software can be alternately utilized for movement sensing of other manufacturing plant machinery outside of the cement industry, however, the preferred embodiment disclosed hereinabove utilizes this software in an advantageous manner that may not otherwise be obtained. Similarly, the analog-to-digital-to-analog sensor signal conversion and transmission to the CPU through multiplexed channels may be employed for various other machine sensing and other industries, however, the cement manufacturing plant advantages may not be fully obtained. It should be appreciated that other modifications and variations may be made to the preferred system without departing from the spirit and scope of the present invention.

The invention claimed is:

1. A monitoring system for cement manufacturing, the system comprising:
    (a) a first cement manufacturing machine;
    (b) at least a first sensor coupled to the first machine operably sensing a movement condition associated with a portion of the first machine;
    (c) at least a second cement manufacturing machine located remotely from and performing a different manufacturing operation than the first machine;
    (d) at least a second sensor coupled to the second machine operably sensing a movement condition associated with a portion of the second machine;
    (e) a central computer operably receiving signals from the first and second sensors while being remotely located from the first and second machines;
    (f) software instructions used by the central computer to automatically perform substantially real-time calculations based at least in part on signals from the sensors to determine and report operating problems with sensed portions of the machines; and
    (g) a hand-held and portable electronic data collector operable to receive signals through the central computer from a third sensor coupled to a third remotely located cement manufacturing machine, the hand-held data collector operably interfacing with the central computer to transfer sensor data to an offline database.

2. The system of claim 1, further comprising at least a first switch matrix and a multiplexer connecting at least the first and second sensors to the central computer to provide at least a sixty-four channel data acquisition device with analog-to-digital sensor-to-multiplexer signal conversion, and the monitored sensors exceeding four signals.

3. The system of claim 1, wherein one of the machines includes a rotating cement kiln.

4. The system of claim 1, wherein one of the machines includes a rotating crusher.

5. The system of claim 1, wherein one of the machines includes a fan.

6. The system of claim 1, wherein one of the machines includes a separator.

7. A monitoring system for cement manufacturing, the system comprising:
    (a) a first cement manufacturing machine;
    (b) at least a first sensor coupled to the first machine operably sensing a movement condition associated with a portion of the first machine;
    (c) at least a second cement manufacturing machine located remotely from and performing a different manufacturing operation than the first machine;
    (d) at least a second sensor coupled to the second machine operably sensing a movement condition associated with a portion of the second machine;
    (e) a central computer operably receiving signals from the first and second sensors while being remotely located from the first and second machines;
    (f) software instructions used by the central computer to automatically perform substantially real-time calculations based at least in part on signals from the sensors to determine and report operating problems with sensed portions of the machines;
    wherein the first sensor operably senses vibration of a bearing assembly in the first machine, and the central computer automatically compares real-time sensed vibrational values to target values and automatically activates an alarm indicator if the compared value difference exceeds an alarm limit.

8. The system of claim 7, further comprising a hand-held and portable electronic data collector operable to receive signals through the central computer from a third sensor coupled to a third remotely located cement manufacturing machine, the hand-held data collector operably interfacing with the central computer to transfer sensor data to a database.

9. The system of claim 7, wherein one of the machines includes a rotating cement kiln.

10. The system of claim 7, wherein one of the machines includes a rotating crusher.

11. The system of claim 7, wherein one of the machines includes a fan.

12. The system of claim 7, wherein one of the machines includes a separator.

13. A monitoring system for cement manufacturing, the system comprising:
    (a) a kiln;
    (b) a crusher;
    (c) a separator;
    (d) a fan;
    (e) sensors detecting movement-related characteristics of the kiln, crusher, separator and fan;
    (f) a central processing unit receiving substantially real-time and continuous signals from the sensors and using the signals to determine if any undesirable conditions are present with regard to the kiln, crusher, separator and fan, and to identify one or more likely causes of the undesirable conditions; and
    (g) at least a first switch matrix and a multiplexer connecting the sensors to the central processing unit to provide at least a sixty-four channel data acquisition device.

14. The system of claim 13, wherein at least one of the sensors senses a characteristic of a rotating bearing assembly, and the central processing unit automatically compares real-time sensed vibrational values to target values and automatically activates an alarm indicator if the compared value difference exceeds an alarm limit.

15. The system of claim 13, wherein the sensors send at least 1,000 qualitative samples per second to the central processing unit.

13

16. The system of claim 13, further comprising:
a hand-held electronic data collector communicating with the central processing unit to download sensor data; and
a control room including a display visually showing a simulated representation of the kiln, crusher, separator and fan.

17. The system of claim 13, wherein at least one of the sensors senses vibration of a bearing assembly in one of the kiln, crusher, separator or fan, and the central processing unit automatically compares real-time sensed vibrational values from the at least one of the sensors to target values and automatically activates a warning signal if the compared value difference exceeds a limit.

18. A monitoring system for cement manufacturing, the system comprising:
(a) a kiln;
(b) a crusher;
(c) a separator;
(d) a fan;
(e) sensors detecting movement-related characteristics of the kiln, crusher, separator and fan;
(f) a central processing unit receiving substantially real-time and continuous signals from the sensors and using the signals to determine if any undesirable conditions are present with regard to the kiln, crusher, separator and fan, and to identify one or more likely causes of the undesirable conditions; and
(g) a display visually showing a simulated representation of the kiln, crusher, separator and fan, and an indication feature based on the sensor signals associated therewith.

19. The system of claim 18, further comprising at least a first switch matrix and a multiplexer connecting the sensors to the central processing unit to provide at least a sixty-four channel data acquisition device.

20. The system of claim 18, wherein at least one of the sensors senses vibration of a bearing assembly in one of the kiln, crusher, separator or fan, and the central processing unit automatically compares real-time sensed vibrational values from the at least one of the sensors to target values and automatically activates a warning signal if the compared value difference exceeds a limit.

21. The system of claim 18, further comprising a hand-held electronic data collector communicating with the central processing unit to download sensor data.

22. A monitoring system for cement manufacturing, the system comprising:
(a) a kiln;
(b) a crusher;
(c) a separator;
(d) a fan;
(e) sensors detecting movement-related characteristics of the kiln, crusher, separator and fan;
(f) a central processing unit receiving substantially real-time and continuous signals from the sensors and using the signals to determine if any undesirable conditions are present with regard to the kiln, crusher, separator and fan, and to identify one or more likely causes of the undesirable conditions; and
(g) a hand-held electronic data collector operable to communicate with the central processing unit to download sensor data from a remotely located cement manufacturing machine.

23. The system of claim 22, wherein at least one of the sensors senses vibration of a bearing assembly in one of the kiln, crusher, separator or fan, and the central processing unit automatically compares real-time sensed vibrational values from the at least one of the sensors to target values and automatically activates a warning signal if the compared value difference exceeds a limit.

24. The system of claim 22, further comprising:
software instructions operating within the central processing unit automatically determining if there is a problem and a severity of the problem in a real-time manner;
the software instructions providing historical trends; and
the software instructions providing maintenance notifications for at least the kiln and crusher.

25. A monitoring system for cement manufacturing, the system comprising:
(a) a kiln;
(b) a crusher;
(c) a separator;
(d) a fan;
(e) sensors detecting movement-related characteristics of the kiln, crusher, separator and fan; and
(f) a central processing unit receiving substantially real-time and continuous signals from the sensors and using the signals to determine if any undesirable conditions are present with regard to the kiln, crusher, separator and fan, and to identify one or more likely causes of the undesirable conditions;
wherein the sensors include at least three differently oriented vibration sensors located adjacent the kiln.

26. The system of claim 25, further comprising:
a hand-held electronic data collector communicating with the central processing unit to download sensor data; and
a control room including a display visually showing a simulated representation of the kiln, crusher, separator and fan.

27. The system of claim 25, further comprising:
software instructions operating within the central processing unit automatically determining if there is a problem and a severity of the problem in a real-time manner;
the software instructions providing historical trends; and
the software instructions providing maintenance notifications for at least the kiln and crusher.

28. A monitoring system for cement manufacturing, the system comprising:
(a) a kiln;
(b) a crusher;
(c) a separator;
(d) a fan;
(e) sensors detecting movement-related characteristics of the kiln, crusher, separator and fan;
(f) a central processing unit receiving substantially real-time and continuous signals from the sensors and using the signals to determine if any undesirable conditions are present with regard to the kiln, crusher, separator and fan, and to identify one or more likely causes of the undesirable conditions; and
(g) an evolutionary learning program being used by the central processing unit to automatically adapt its undesirable condition determination through repeated use over time.

29. The system of claim 28, further comprising:
a hand-held electronic data collector communicating with the central processing unit to download sensor data; and
a control room including a display visually showing a simulated representation of the kiln, crusher, separator and fan.

30. The system of claim 28, wherein at least one of the sensors senses vibration of a bearing assembly in one of the kiln, crusher, separator or fan, and the central processing unit automatically compares real-time sensed vibrational values from the at least one of the sensors to target values and automatically activates a warning signal if the compared value difference exceeds a limit.

31. The system of claim 28, further comprising:
software instructions operating within the central processing unit automatically determining if there is a problem and a severity of the problem in a real-time manner;
the software instructions providing historical trends; and
the software instructions providing maintenance notifications for at least the kiln and crusher.

32. A monitoring system for cement manufacturing, the system comprising:
(a) a kiln;
(b) a crusher;
(c) a separator;
(d) a fan;
(e) sensors detecting movement-related characteristics of the kiln, crusher, separator and fan;
(f) a central processing unit receiving substantially real-time and continuous signals from the sensors and using the signals to determine if any undesirable conditions are present with regard to the kiln, crusher, separator and fan, and to identify one or more likely causes of the undesirable conditions;
wherein the central processing unit uses at least one of the sensor signals to automatically determine if a mechanically unbalanced movement condition exists.

33. The system of claim 32, further comprising:
a hand-held electronic data collector communicating with the central processing unit to download sensor data; and
a control room including a display visually showing a simulated representation of the kiln, crusher, separator and fan.

34. The system of claim 32, wherein at least one of the sensors senses vibration of a bearing assembly in one of the kiln, crusher, separator or fan, and the central processing unit automatically compares real-time sensed vibrational values from the at least one of the sensors to target values and automatically activates a warning signal if the compared value difference exceeds a limit.

35. The system of claim 32, further comprising:
software instructions operating within the central processing unit automatically determining if there is a problem and a severity of the problem in a real-time manner;
the software instructions providing historical trends; and
the software instructions providing maintenance notifications for at least the kiln and crusher.

36. A computer program, stored in memory, comprising:
a set of instructions receiving substantially real-time vibration sensor data in cement making machinery;
a set of instructions comparing the real-time sensor data to target sensor data;
a set of instructions automatically determining if an undesirable condition exists in the cement making machinery, and automatically identifying and reporting a potential cause of the undesirable condition based at least in part on the data comparison and determination; and
a set of instructions automatically determining if an undesired rotational imbalance is occurring in the cement making machinery.

37. The computer program of claim 36, further comprising:
a set of instructions determining a severity of the undesirable condition;
a set of instructions displaying historical trends based on the sensed data; and
a set of instructions providing maintenance notifications for the cement making machinery.

38. A computer program, stored in memory, comprising:
a set of instructions receiving substantially real-time vibration sensor data in cement making machinery;
a set of instructions comparing the real-time sensor data to target sensor data;
a set of instructions automatically determining if an undesirable condition exists in the cement making machinery, and automatically identifying and reporting a potential cause of the undesirable condition based at least in part on the data comparison and determination; and
a set of instructions automatically determining if an undesired bearing condition is occurring in the cement making machinery.

39. The computer program of claim 38, further comprising:
a set of instructions determining a severity of the undesirable condition;
a set of instructions displaying historical trends based on the sensed data; and
a set of instructions providing maintenance notifications for the cement making machinery.

40. A computer program, stored in memory, comprising:
a set of instructions receiving substantially real-time vibration sensor data in cement making machinery;
a set of instructions comparing the real-time sensor data to target sensor data;
a set of instructions automatically determining if an undesirable condition exists in the cement making machinery, and automatically identifying and reporting a potential cause of the undesirable condition based at least in part on the data comparison and determination; and
a set of instructions analyzing analog data from at least fifty vibrational sensors associated with multiple cement making machines in a substantially real-time and continuous manner.

41. The computer program of claim 40, further comprising a set of instructions automatically determining if an undesired rotational imbalance is occurring in the cement making machinery.

42. The computer program of claim 40, further comprising:
a set of instructions determining a severity of the undesirable condition;
a set of instructions displaying historical trends based on the sensed data; and
a set of instructions providing maintenance notifications for the cement making machinery.

43. A computer program, stored in memory, comprising:
a set of instructions receiving substantially real-time vibration sensor data in cement making machinery;
a set of instructions comparing the real-time sensor data to target sensor data;
a set of instructions automatically determining if an undesirable condition exists in the cement making machinery, and automatically identifying and reporting a potential cause of the undesirable condition based at least in part on the data comparison and determination; and
a set of instructions visually displaying a simulated representation of the cement making machinery and an indication image of the sensor data.

44. The computer program of claim 43, further comprising:
a set of instructions determining a severity of the undesirable condition;
a set of instructions displaying historical trends based on the sensed data; and
a set of instructions providing maintenance notifications for the cement making machinery.

45. A method of using and monitoring machines to manufacture cement, the method comprising:
(a) moving a portion of a first machine;

(b) detecting a characteristic associated with the movement of step (a);
(c) moving a portion of a second machine remotely located relative to the first machine;
(d) detecting a characteristic associated with the movement of step (c);
(e) moving a portion of a third machine remotely located relative to the first and second machines;
(f) detecting a characteristic associated with the movement of step (e);
(g) making cement with the machines;
(h) substantially simultaneously using remotely located software instructions to automatically determine if an undesirable mechanical condition exists in the first, second and third machines based at least in part on the detected characteristics, and if so, automatically identifying a probable cause; and
(i) using an evolutionary learning calculation to assist in making the probable cause identification.

46. The method of claim 45, further comprising using the software instructions to compare historical detected data to real-time detected characteristic data.

47. The method of claim 45, further comprising transmitting sensed data from a central processing unit, associated with a central control room, to a hand-held electronic data collector, the central processing unit running the software instructions.

48. A method of using and monitoring machines to manufacture cement, the method comprising:
(a) moving a portion of a first machine;
(b) detecting a characteristic associated with the movement of step (a);
(c) moving a portion of a second machine remotely located relative to the first machine;
(d) detecting a characteristic associated with the movement of step (c);
(e) moving a portion of a third machine remotely located relative to the first and second machines;
(f) detecting a characteristic associated with the movement of step (e);
(g) making cement with the machines;
(h) substantially simultaneously using remotely located software instructions to automatically determine if an undesirable mechanical condition exists in the first, second and third machines based at least in part on the detected characteristics, and if so, automatically identifying a probable cause;
(i) rotating a hollow tube of a cement kiln machine;
(j) energizing a motor to rotate a transmission which rotates the tube;
(k) supporting the transmission with a stationary block and a bearing assembly located between the transmission and the block;
(l) heating crushed rock in the kiln to make clinker;
(m) receiving signals from a first set of sensors located adjacent the block and operably sensing vibrations of at least one of: (a) the tube, (b) the transmission, and (c) the bearing assembly;
(n) receiving signals from a second set of sensors located adjacent the motor and operably sensing vibrations of at least one of: (a) the motor and (b) the transmission;
(o) using the software instructions to determine if an undesired rotational imbalance is occurring within the kiln machine and if an undesired rotational bearing condition is occurring within the kiln machine; and
(p) visually displaying a simulated representation of the kiln machine and a sensor indication image.

49. The method of claim 48, further comprising using an evolutionary learning calculation to assist in making the probable cause identification.

50. The method of claim 48, further comprising transmitting sensed data from a central processing unit, associated with a central control room, to a hand-held electronic data collector, the central processing unit running the software instructions.

\* \* \* \* \*